(12) United States Patent
Dunphy et al.

(10) Patent No.: US 10,201,623 B2
(45) Date of Patent: Feb. 12, 2019

(54) HSP90-TARGETED CARDIAC IMAGING AND THERAPY

(71) Applicant: Memorial Sloan-Kettering Cancer Center, New York, NY (US)

(72) Inventors: Mark Dunphy, New York, NY (US); H. William Strauss, New York, NY (US); Gabriela Chiosis, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 176 days.

(21) Appl. No.: 14/776,143

(22) PCT Filed: Mar. 14, 2014

(86) PCT No.: PCT/US2014/029243
§ 371 (c)(1),
(2) Date: Sep. 14, 2015

(87) PCT Pub. No.: WO2014/144715
PCT Pub. Date: Sep. 18, 2014

(65) Prior Publication Data
US 2016/0015837 A1 Jan. 21, 2016

Related U.S. Application Data

(60) Provisional application No. 61/799,106, filed on Mar. 15, 2013.

(51) Int. Cl.
| | | |
|---|---|---|
| *A61K 51/04* | (2006.01) | |
| *A61B 5/00* | (2006.01) | |
| *A61K 45/06* | (2006.01) | |
| *G01N 33/60* | (2006.01) | |
| *G01N 33/68* | (2006.01) | |
| *A61K 31/52* | (2006.01) | |
| *A61B 5/0402* | (2006.01) | |
| *A61B 5/055* | (2006.01) | |
| *A61B 6/03* | (2006.01) | |
| *A61B 6/00* | (2006.01) | |

(52) U.S. Cl.
CPC ........ *A61K 51/0459* (2013.01); *A61B 5/0044* (2013.01); *A61B 5/0402* (2013.01); *A61B 5/055* (2013.01); *A61B 5/4884* (2013.01); *A61B 5/7275* (2013.01); *A61B 5/7278* (2013.01); *A61B 6/032* (2013.01); *A61B 6/037* (2013.01); *A61B 6/4417* (2013.01); *A61K 31/52* (2013.01); *A61K 45/06* (2013.01); *G01N 33/60* (2013.01); *G01N 33/6893* (2013.01); *G01N 2333/47* (2013.01); *G01N 2800/32* (2013.01); *G01N 2800/325* (2013.01); *G01N 2800/52* (2013.01)

(58) Field of Classification Search
CPC ........... A61K 51/00; A61K 45/06; A61B 5/00
See application file for complete search history.

(56) References Cited

U.S. PATENT DOCUMENTS

| | | |
|---|---|---|
| 4,940,726 A | 7/1990 | Pettit et al. |
| 4,996,237 A | 2/1991 | Pettit et al. |
| 5,409,953 A | 4/1995 | Pettit et al. |
| 5,423,753 A | 6/1995 | Fowles et al. |
| 5,430,062 A | 7/1995 | Cushman et al. |
| 5,504,074 A | 4/1996 | D'Amato et al. |
| 5,525,632 A | 6/1996 | Obsumi et al. |
| 5,561,122 A | 10/1996 | Pettit |
| 5,569,786 A | 10/1996 | Pettit et al. |
| 5,646,176 A | 7/1997 | Golik et al. |
| 5,661,143 A | 8/1997 | D'Amato et al. |
| 5,674,906 A | 10/1997 | Hatanaka et al. |

(Continued)

FOREIGN PATENT DOCUMENTS

| | | |
|---|---|---|
| WO | WO-1992/16486 A1 | 10/1992 |
| WO | WO-1994/14787 A1 | 7/1994 |

(Continued)

OTHER PUBLICATIONS

Aleksandrzak, K. et al., Antimitotic activity of diaryl compounds with structural features resembling combretastatin A-4, Anticancer Drugs, 9(6):545-50 (1998).
Andres, C.J. et al., "Combretatropones"—hybrids of combretastatin and colchicine, Synthesis and biochemical evaluation, Bioorganic & Medicinal Chemistry Letters, 3(4): 565-570 (1993).
Bacher, G. et al., D-24851, a novel synthetic microtubule inhibitor, exerts curative antitumoral activity in vivo, shows efficacy toward multidrug-resistant tumor cells, and lacks neurotoxicity, Cancer Res., 61(1):392-9 (2001).
Bai, R. et al., Interaction of dolastatin 10 with tubulin: induction of aggregation and binding and dissociation reactions, Mol. Pharmacol., 47(5):965-76 (1995).

(Continued)

*Primary Examiner* — Michael G. Hartley
*Assistant Examiner* — Jagadishwar R Samala
(74) *Attorney, Agent, or Firm* — Choate, Hall & Stewart LLP; Brenda Herschbach Jarrell; John Rearick

(57) ABSTRACT

The present invention provides new methods for cardiac imaging and related medical applications thereof. In some embodiments, the present invention provides a method for the diagnosis of cardiovascular diseases, conditions, or disorders. In some embodiments, the present invention provides a method for the treatment or prevention of cardiovascular diseases, conditions, or disorders. In some embodiments, the present invention provides methods for monitoring the effect of cancer treatment on the heart, and/or methods for monitoring a cancer treatment regimen. In some embodiments, the present invention provides a method for selecting subjects for a test or treatment. In some embodiments, the present invention provides a method for determining the dosage of a drug. In some embodiments, the present invention provides methods for determining the risk of a cardiovascular disease, for assessing risk of a cardiovascular disease, and/or for determining the risk of heart attack.

33 Claims, 6 Drawing Sheets

(56) References Cited

U.S. PATENT DOCUMENTS

| | | | |
|---|---|---|---|
| 5,731,353 A | 3/1998 | Ohsumi et al. | |
| 5,886,025 A | 3/1999 | Pinney | |
| 5,892,069 A | 4/1999 | D'Amato et al. | |
| 5,985,837 A | 11/1999 | Ritter et al. | |
| 6,150,407 A | 11/2000 | Tuse et al. | |
| 6,162,810 A | 12/2000 | Carson et al. | |
| 6,162,930 A | 12/2000 | Pinney et al. | |
| 6,169,104 B1 | 1/2001 | Tuse et al. | |
| 6,201,001 B1 | 3/2001 | Wang et al. | |
| 6,232,327 B1 | 5/2001 | Nickel et al. | |
| 6,262,094 B1 | 7/2001 | Hoefle et al. | |
| 6,271,220 B1 | 8/2001 | Garst et al. | |
| 6,329,420 B1 | 12/2001 | Uckun et al. | |
| 6,335,364 B1 | 1/2002 | Uckun et al. | |
| 6,350,777 B2 | 2/2002 | Pinney et al. | |
| 6,358,957 B1 | 3/2002 | Fukumoto et al. | |
| 6,423,753 B1 | 7/2002 | Dougherty | |
| 6,433,012 B1 | 8/2002 | Tuse et al. | |
| 6,528,676 B1 | 3/2003 | D'Amato et al. | |
| 7,160,885 B2* | 1/2007 | Currie | C07D 487/04 514/249 |
| 7,834,181 B2* | 11/2010 | Chiosis | C07D 473/34 544/276 |
| 8,178,687 B2 | 5/2012 | Alasia et al. | |
| 8,324,240 B2 | 12/2012 | Cai et al. | |
| 2003/0149003 A1 | 8/2003 | Chaplin et al. | |
| 2005/0107343 A1 | 5/2005 | Kasibhatla et al. | |
| 2005/0143429 A1 | 6/2005 | Danishefsky et al. | |
| 2008/0234314 A1 | 9/2008 | Cai et al. | |
| 2008/0311038 A1* | 12/2008 | Auberson | A61K 51/0412 424/1.89 |
| 2011/0085969 A1* | 4/2011 | Rollo | A61K 51/0491 424/1.41 |
| 2011/0201587 A1 | 8/2011 | Shapiro | |
| 2011/0218143 A1* | 9/2011 | Kaushal | A61K 31/165 514/6.9 |
| 2012/0032371 A1 | 2/2012 | King | |
| 2012/0035690 A1 | 2/2012 | Turtzo | |
| 2012/0045861 A1 | 2/2012 | Eguchi et al. | |
| 2012/0045864 A1 | 2/2012 | Wada | |
| 2012/0046266 A1 | 2/2012 | Brasca et al. | |
| 2012/0237508 A1 | 9/2012 | Cai et al. | |
| 2012/0264770 A1 | 10/2012 | Co et al. | |
| 2012/0277257 A1 | 11/2012 | Yu et al. | |
| 2013/0045983 A1 | 2/2013 | Echeverria et al. | |
| 2013/0109684 A1* | 5/2013 | Blagg | C07D 233/26 514/230.5 |
| 2014/0170068 A1* | 6/2014 | Thiele | G01N 33/564 424/9.1 |

FOREIGN PATENT DOCUMENTS

| | | |
|---|---|---|
| WO | WO-1995/04535 A1 | 2/1995 |
| WO | WO-1998/39323 A1 | 9/1998 |
| WO | WO-1999/02166 A1 | 1/1999 |
| WO | WO-1999/02514 A2 | 1/1999 |
| WO | WO-1999/34788 A1 | 7/1999 |
| WO | WO-1999/35150 A1 | 7/1999 |
| WO | WO-1999/35164 A1 | 7/1999 |
| WO | WO-1999/48495 A1 | 9/1999 |
| WO | WO-1999/51224 A1 | 10/1999 |
| WO | WO-1999/51246 A1 | 10/1999 |
| WO | WO-2000/00514 A2 | 1/2000 |
| WO | WO-2000/06556 A1 | 2/2000 |
| WO | WO-2000/26229 A1 | 5/2000 |
| WO | WO-2000/35865 A2 | 6/2000 |
| WO | WO-2000/40529 A1 | 7/2000 |
| WO | WO-2000/41669 A2 | 7/2000 |
| WO | WO-2000/48590 A1 | 8/2000 |
| WO | WO-2000/48591 A1 | 8/2000 |
| WO | WO-2000/73264 A1 | 12/2000 |
| WO | WO-2002/04434 A1 | 1/2001 |
| WO | WO-2001/09103 A2 | 2/2001 |
| WO | WO-2001/12579 A2 | 2/2001 |
| WO | WO-2001/19794 A2 | 3/2001 |
| WO | WO-2001/22954 A2 | 4/2001 |
| WO | WO-2001/30803 A1 | 5/2001 |
| WO | WO-2001/40268 A2 | 6/2001 |
| WO | WO-2001/68654 A2 | 9/2001 |
| WO | WO-2001/81288 A1 | 11/2001 |
| WO | WO-2001/81355 A1 | 11/2001 |
| WO | WO-2001/82909 A2 | 11/2001 |
| WO | WO-2001/84929 A1 | 11/2001 |
| WO | WO-2001/92224 A1 | 12/2001 |
| WO | WO-2002/06267 A2 | 1/2002 |
| WO | WO-2002/08213 A1 | 1/2002 |
| WO | WO-2002/12228 A1 | 2/2002 |
| WO | WO-2002/14329 A1 | 2/2002 |
| WO | WO-2002/22576 A2 | 3/2002 |
| WO | WO-2002/22626 A1 | 3/2002 |
| WO | WO-2002/42319 A2 | 5/2002 |
| WO | WO-2002/47604 A2 | 6/2002 |
| WO | WO-2002/050007 A2 | 6/2002 |
| WO | WO-2002/060872 A1 | 8/2002 |
| WO | WO-2004/097428 A1 | 11/2004 |
| WO | WO-2006/098761 A2 | 9/2006 |
| WO | WO-2006/117669 A1 | 11/2006 |
| WO | WO-2006/123165 A2 | 11/2006 |
| WO | WO-2007/104944 A1 | 9/2007 |
| WO | WO-2007/134298 A1 | 11/2007 |
| WO | WO-2007/134677 A1 | 11/2007 |
| WO | WO-2008/005937 A2 | 1/2008 |
| WO | WO-2008/093075 A2 | 8/2008 |
| WO | WO-2008/115719 A1 | 9/2008 |
| WO | WO-2008/118391 A2 | 10/2008 |
| WO | WO-2009/097578 A1 | 8/2009 |
| WO | WO-2010/025272 A1 | 3/2010 |
| WO | WO-2011/044394 A1 | 4/2011 |
| WO | WO-2012/138894 A1 | 10/2012 |
| WO | WO-2013/009655 A2 | 1/2013 |

OTHER PUBLICATIONS

Banwell, M.G. et al., cis-1,2-Dihydrocatechols in Chemical Synthesis: First Synthesis of L-Ascorbic Acid (Vitamin C) from a Non-Carbohydrate Source, Australian Journal of Chemistry, 52(2):137-142 (1999).

Bedford et al., Synthesis of water-soluble prodrugs of the cytotoxic agent combretastatin A4, Bioorganic and Medicinal Chemistry Lett., 6(2):157-160 (1996).

Blokhin, A.V. et al., Characterization of the interaction of the marine cyanobacterial natural product curacin a with the colchicine site of tubulin and initial structure-activity studies with analogues, Mol. Pharmacol., 48(3):523-31 (1995).

Boger, D.L. et al, An improved synthesis of 1,2,9,9a-tetrahydrocyclopropa[c]benz[e]indol-4-one (CBI): a simplified analog of the CC-1065 alkylation subunit, J. Org. Chem., 57(10):2873-2876 (1992).

Chou, T.C. et al., Therapeutic cure against human tumor xenografts in nude mice by a microtubule stabilization agent, fludelone, via parenteral or oral route, Cancer Res., 65(20):9445-54 (2005).

Chou, T.C. et al., Therapeutic effect against human xenograft tumors in nude mice by the third generation microtubule stabilizing epothilones, Proc. Natl. Acad. Sci. U S A. 105(35):13157-62 (2008).

Combeau, C., et al., RPR112378 and RPR115781: two representatives of a new family of microtubule assembly inhibitors. Mol. Pharmacal, 57(3): 553-563 (2000).

Cortese, F. et al., Podophyllotoxin as a probe for the colchicine binding site of tubulin, J. Biol. Chem., 252(4):1134-40 (1977).

Cushman, M. et al., Synthesis and evaluation of stilbene and dihydrostilbene derivatives as potential anticancer agents that inhibit tubulin polymerization, J. Med. Chem., 34(8):2579-88 (1991).

Cushman, M. et al., Synthesis of analogs of 2-methoxyestradiol with enhanced inhibitory effects on tubulin polymerization and cancer cell growth, J. Med. Chem., 40(15):2323-34 (1997).

Dorr, R.T. et al., Antitumor activity of combretastatin-A4 phosphate, a natural product tubulin inhibitor, Invest. New Drugs, 14(2):131-7 (1996).

(56) References Cited

OTHER PUBLICATIONS

Ducki, S. et al., Potent antimitotic and cell growth inhibitory properties of substituted chalcones, Bioorg. Med. Chem. Lett., 8(9):1051-6 (1998).

Flynn, B.L. et al., The synthesis and tubulin binding activity of thiophene-based analogues of combretastatin A-4, Bioorg. Med. Chem. Lett., 11(17):2341-3 (2001).

Fotsis, T. et al., The endogenous oestrogen metabolite 2-methoxyoestradiol inhibits angiogenesis and suppresses tumour growth, Nature, 368(6468):237-9 (1994).

Gastpar, R. et al.,. Methoxy-substituted 3-formyl-2-phenylindoles inhibit tubulin polymerization, J. Med. Chem., 41(25):4965-72 (1998).

Gerwick, W.H. et al, Structure of Curacin A, a Novel Antimitotic, Antiproliferative and Brine Shrimp Toxic Natural Product from the Marine Cyanobacterium Lyngbya majuscula, J. Org. Chem., 59(6):1243-1245 (1994).

Getahun, Z. et al., Synthesis of alkoxy-substituted diaryl compounds and correlation of ring separation with inhibition of tubulin polymerization: differential enhancement of inhibitory effects under suboptimal polymerization reaction conditions, J. Med. Chem., 35(6):1058-67 (1992).

Gwaltney, S.L. 2nd et al., Novel sulfonate analogues of combretastatin A-4: potent antimitotic agents, Bioorg. Med. Chem. Lett., 11(7):871-4 (2001).

Hadimani, M.B. et al., Synthesis, in vitro, and in vivo evaluation of phosphate ester derivatives of combretastatin A-4, Bioorg. Med. Chem. Lett., 13(9):1505-8 (2003).

Hammonds, T.R., et al., Studies to show that with podophyllotoxin the early replicative stages of herpes simplex virus type 1 depend upon functional cytoplasmic microtubules, J. Med. Microbial, 45(3): 167-172 (1996).

Hatanaka, T. et al., Novel B-ring modified combretastatin analogues: syntheses and antineoplastic activity, Bioorg. Med. Chem. Lett., 8(23):3371-4 (1998).

Holwell, S.E. et al., Anti-vascular effects of vinflunine in the MAC 15A transplantable adenocarcinoma model, Br. J. Cancer, 84(2):290-5 (2001).

Hsieh, H. P., et al., Structure-activity and crystallographic analysis of benzophenone derivatives—the potential anticancer agents. Bioorg. Med. Chem. Lett.,13(5): 977 (2003).

Janik, M.E. and Bane, S.L., Synthesis and antimicrotubule activity of combretatropone derivatives, Bioorganic & Medicinal Chemistry, 10(6): 1895-1903 (2002).

Jhaveri, K. and Modi, S., HSP90 inhibitors for cancer therapy and overcoming drug resistance, Adv. Pharmacol., 65:471-517 (2012).

Jiang, J.B. et al., Synthesis and biological evaluation of 2-styrylquinazolin-4(3H)-ones, a new class of antimitotic anticancer agents which inhibit tubulin polymerization, J. Med. Chem., 33(6):1721-8 (1990).

Kanoh, K. et al., (−)-Phenylahistin arrests cells in mitosis by inhibiting tubulin polymerization. J Antibiot (Tokyo), 52(2):134-41 (1999).

Kanoh, K. et al., Synthesis and biological activities of phenylahistin derivatives, Bioorg. Med. Chem., 7(7):1451-7 (1999).

Kapustian, L.L. et al., Hsp90 and its co-chaperone, Sgt1, as autoantigens in dilated cardiomyopathy, Heart Vessels, 28(1):114-9 (2013).

Kim, Y. et al., Synthesis and Cytotoxicity of 3,4-Diaryl-2(5H)-furanones, Bioorganic & Medicinal Chemistry Letters, 12(4): 719-722 (2002).

Kingston, D.G.I., and Samranayake, C.A., The Chemistry of Taxol, a Clinically Useful Anticancer Agent, J. Nat. Prod., 53(1): 1-12 (1990).

Lavielle, G. et al., New alpha-amino phosphonic acid derivatives of vinblastine: chemistry and antitumor activity, J. Med. Chem., 34(7):1998-2003 (1991).

Lawrence, N.J. et al., Antimitotic and cell growth inhibitory properties of combretastatin A-4-like ethers, Bioorg. Med. Chem. Lett., 11(1):51-4 (2001).

Lawrence, N.J. et al., The interaction of chalcones with tubulin, Anticancer Drug Des., 15(2):135-41 (2000).

Leoni, L.M., et al., Indanocine, a microtubule-binding indanone and a selective inducer of apoptosis in multidrug-resistant cancer cells, J. Natl. Cancer Inst., 92(3):217-24 (2000).

Lin, C. M., et al., Antimitotic natural products combretastatin A-4 and combretastatin A-2: studies on the mechanism of their inhibition of the binding of colchicine to tubulin, Biochemistry, 28 (17), 6984-6991 (1989).

Lu, P., Monitoring cardiac function in patients receiving doxorubicin, Semin. Nucl. Med., 35(3):197-201 (2005).

Mahboobi, S., et al., Synthetic 2-aroylindole derivatives as a new class of potent tubulin-inhibitory, antimitotic agents, J. Med. Chem., 44(26), 4535-53 (2001).

Medarde, M. et al., Synthesis and antineoplastic activity of combretastatin analogues: Heterocombretastatins, European Journal of Medicinal Chemistry, 33(1): 71-77 (1998).

Medarde, M. et al., Synthesis and pharmacological activity of combretastatin analogues. Naphthylcombretastatins and related compounds, Bioorganic & Medicinal Chemistry Letters, 5(3): 229-232 (1995).

Medarde, M., et al. Synthesis and Pharmacological Activity of Diarylindole Derivatives. Cytotoxic Agents Based on Combretastatins, Bioorg. Med. Chem. Lett., 9(16), pp. 2303-2308 (1999).

Medina, J. C., et al., Novel antineoplastic agents with efficacy against multidrug resistant tumor cells. Bioorg Med Chem Lett. 8(19):2653-6 (1998).

Mu, F., et al. Synthesis, anticancer activity, and inhibition of tubulin polymerization by conformationally restricted analogues of lavendustin A, J. Med. Chem., 46(9), pp. 1670-1682 (2003).

Nakada, M. et al., The first total synthesis of the antitumor macrolide, rhizoxin, Tetrahedron Letters, 34(6): 1039-1042 (1993).

Nam, N.H. et al., Combretastatin A-4 analogues as antimitotic antitumor agents, Curr. Med. Chem., 10(17):1697-722 (2003).

Nam, N.H. et al., Combretoxazolones: synthesis, cytotoxicity and antitumor activity, Bioorganic & Medicinal Chemistry Letters, 11(23): 3073-3076 (2001).

Nam, N.H. et al., Synthesis and anti-tumor activity of novel combretastatins: combretocyclopentenones and related analogues, Bioorg. Med. Chem. Lett., 12(15):1955-8 (2002).

Nicolaou, K.C., Synthesis of epothilones A and B in solid and solution phase, Nature, 387(6630):268-72 (1997).

Owellen, R.J. et al., Inhibition of tubulin-microtubule polymerization by drugs of the Vinca alkaloid class, Cancer Res., 36(4):1499-502 (1976).

Pettit, G. R., et al., Antineoplastic agents. 443. Synthesis of the cancer cell growth inhibitor hydroxyphenstatin and its sodium diphosphate prodrug., J. Med. Chem., 43(14): 2731-2737 (2000).

Pettit, G.R. et al., Antineoplastic agents. 113. Synthesis of natural (−)-combretastatin, J. Org. Chem., 50(18): 3404-3406 (1985).

Pettit, G.R. et al., Antineoplastic agents. 150. The structure and synthesis of dolastatin 3, J. Am. Chem. Soc., 109(24): 7581-7582 (1987).

Pettit, G.R. et al., Antineoplastic agents. 257. Isolation and structure of spongistatin 1, J. Org. Chem., 58(6): 1302-1304 (1993).

Pettit, G.R. et al., Antineoplastic agents. 291. Isolation and synthesis of combretastatins A-4, A-5, and A-6(1a), J. Med. Chem., 38(10):1666-72 (1995).

Pettit, G.R. et al., Antineoplastic agents. 360. Synthesis and cancer cell growth inhibitory studies of dolastatin 15 structural modifications, Anticancer Drug Des., 13(1):47-66 (1998).

Pettit, G.R. et al., Antineoplastic agents. 379. Synthesis of phenstatin phosphate, J. Med. Chem., 41(10):1688-95 (1998).

Pettit, G.R. et al., Antineoplastic agents. 429. Syntheses of the combretastatin A-1 and combretastatin B-1 prodrugs, Anticancer Drug Des., 15(3):203-16 (2000).

Pettit, G.R. et al., Antineoplastic agents. 487. Synthesis and biological evaluation of the antineoplastic agent 3,4-methylenedioxy-5,4'-dimethoxy-3'-amino-Z-stilbene and derived amino acid amides, J. Med. Chem., 46(4):525-31 (2003).

Pettit, G.R. et al., Isolation and structure of combretastatin, Canadian Journal of Chemistry, 60(11): 1374-1376 (1982).

(56) References Cited

OTHER PUBLICATIONS

Pettit, G.R. et al., Isolation, structure, and synthesis of combretastatins A-1 and B-1, potent new inhibitors of microtubule assembly, derived from Combretum caffrum, J Nat Prod., 50(1):119-31 (1987).
Pinney, K.G. et al., A new anti-tubulin agent containing the benzo[b]thiophene ring system, Bioorg. Med. Chem. Lett., 9(8):1081-6 (1999).
Pinney, K.G. et al., Synthesis and biological evaluation of aryl azide derivatives of combretastatin a-4 as molecular probes for tubulin, Bioorganic & Medicinal Chemistry, 8(10): 2417-2425 (2000).
Poncet, J., et al., The dolastatins, a family of promising antineoplastic agents, Curr. Pharm Des., 5(3):139-62 (1999).
Rao, A.V.R. et al., Radical mediated enantioselective construction of C-1 to C-9 segment of rhizoxin, Tetrahedron Letters, 33(27): 3907-3910 (1992).
Rao, A.V.R. et al., Studies directed towards the total synthesis of rhizoxin: Stereoselective synthesis of C-12 to C-18 segment, Tetrahedron Letters, 34(4): 707-710 (1993).
Schiff, P.B. et al., Promotion of microtubule assembly in vitro by taxol, Nature, 277(5698):665-667 (1979).
Schumacher, G. et al., Potent antitumor activity of 2-methoxyestradiol in human pancreatic cancer cell lines, Clin. Cancer Res., 5(3):493-9 (1999).
Shan, B. et al., Selective, covalent modification of beta-tubulin residue Cys-239 by T138067, an antitumor agent with in vivo efficacy against multidrug-resistant tumors. Proc Natl Acad Sci U S A. 11;96(10):5686-91 (1999).
Shirai, R. et al., Asymmetric synthesis of antimitotic combretadioxolane with potent antitumor activity against multi-drug resistant cells, Bioorg. Med. Chem. Lett., 8(15):1997-2000 (1998).
Shirai, R. et al., Synthesis and anti-tubulin activity of aza-combretastatins, Bioorganic & Medicinal Chemistry Letters, 4(5): 699-704 (1994).
Shirai, R. et al., Synthesis of Conformationary Restricted Combretastatins, Heterocycles, 46(1): 145-148 (1997).
Singh, S.B. et al., Antineoplastic agents. 166. Isolation, structure, and synthesis of combretastatin C-1, J. Org. Chem., 54(17): 4105-4114 (1989).
Tahir, S. K. et al., A-204197, a new tubulin-binding agent with antimitotic activity in tumor cell lines resistant to known microtubule inhibitors. Cancer Res. 61(14):5480-5 (2001).
Taldone, T. et al., Design, synthesis, and evaluation of small molecule Hsp90 probes, Bioorg. Med. Chem., 19(8):2603-14 (2011).
Uckun, F. M., et al. A rationally designed anticancer drug targeting a unique binding cavity of tubulin. Bioorg Med Chem Lett. 15;10(10):1015-8 (2000).
Verdier-Pinard, P. et al., A steroid derivative with paclitaxel-like effects on tubulin polymerization, Mol. Pharmacol., 57(3):568-75 (2000).
Verdier-Pinard, P. et al., Biosynthesis of radiolabeled curacin A and its rapid and apparently irreversible binding to the colchicine site of tubulin, Arch. Biochem. Biophys., 370(1):51-8 (1999).
Wagner, C. C., et al., Positron emission tomography for use in microdosing studies. Curr Opin Drug Discov Devel. 11(1):104-10 (2008).
Wang, T. and Wade, R.C., Comparative binding energy (COMBINE) analysis of OppA-peptide complexes to relate structure to binding thermodynamics, J. Med. Chem., 45(22):4828-37. (2002).
Wang, Z. et al., Synthesis of B-ring homologated estradiol analogues that modulate tubulin polymerization and microtubule stability, J. Med. Chem., 43(12):2419-29 (2000).
Weber, W. A., et al., Technology Insight: novel imaging of molecular targets is an emerging area crucial to the development of targeted drugs. Nat Clin Pract Oncol. 5(1):44-54 (2008).
Woods, J.A. et al., The interaction with tubulin of a series of stilbenes based on combretastatin A-4, British Journal of Cancer, 71: 705-711 (1995).
Workman, P. et al., Drugging the cancer chaperone HSP90: combinatorial therapeutic exploitation of oncogene addiction and tumor stress. Ann N Y Acad Sci. 1113:202-216 (2007).
Workman, P. et al., Minimally invasive pharmacokinetic and pharmacodynamics technologies in hypothesis-testing clinical trials of innovative therapies, J. Natl. Cancer Inst. 98(9):580-598 (2006).
Wu-Wong, J.R. et al., Identification and characterization of A-105972, an antineoplastic agent, Cancer Res., 61(4):1486-92 (2001).
Xia, Y. et al., Antitumor Agents. 211. Fluorinated 2-phenyl-4-quinolone derivatives as antimitotic antitumor agents. J. Med. Chem. 44(23):3932-6 (2001).
Zhang, X. and Smith, C.D., Microtubule effects of welwistatin, a cyanobacterial indolinone that circumvents multiple drug resistance. Mol Pharmacol. 49(2):288-94 (1996).
Extended European Search Report for EP 14764815.8, 12 pages, dated Sep. 22, 2016.
Husain, S. S., Myocardial Perfusion Imaging Protocols: Is There an Ideal Protocol?, Ideal Myocardial Perfusion Imaging, 35(1): 3-9 (2007).
Pillarsetty, N. et al., Radioiodination, biodistribution and PET imaging studies of Hsp90 inhibitor [$^{123}$I]-H71, Journal of Nuclear Medicine, 5(2): 556 (2010).
Thimister, P. W. L. et al., In Vivo Detection of Cell Death in the Area at Risk in Acute Myocardial Infarction, J. Nucl. Med. 44:391-396 (2003).
Wuest, F. et al., Fluorine- and rhenium-containing geldanamycin derivatives as leads for the development of molecular probes for imaging Hsp90, Org. Biomol. Chem, 10: 6724 (2012).
Xu, Q. et al., Molecular chaperones and heat shock proteins in atherosclerosis, Am. J. Physiol Heart Circ Physiol, 302:H506-H514 (2012).

\* cited by examiner

Fig. 3

| | DAY 1 | | DAY 2 | OPTIONAL DAY |
|---|---|---|---|---|
| [124]I-PUH71 Injection | Start (0 min). No other injections. | | | |
| PET-CT scans * | 0 min | 3-4 H | 20-24 H | 48-72 H (optional) |
| Blood draws | 30 min  1-2 H  3-4 H | 8-16 H | 20-24 H | |

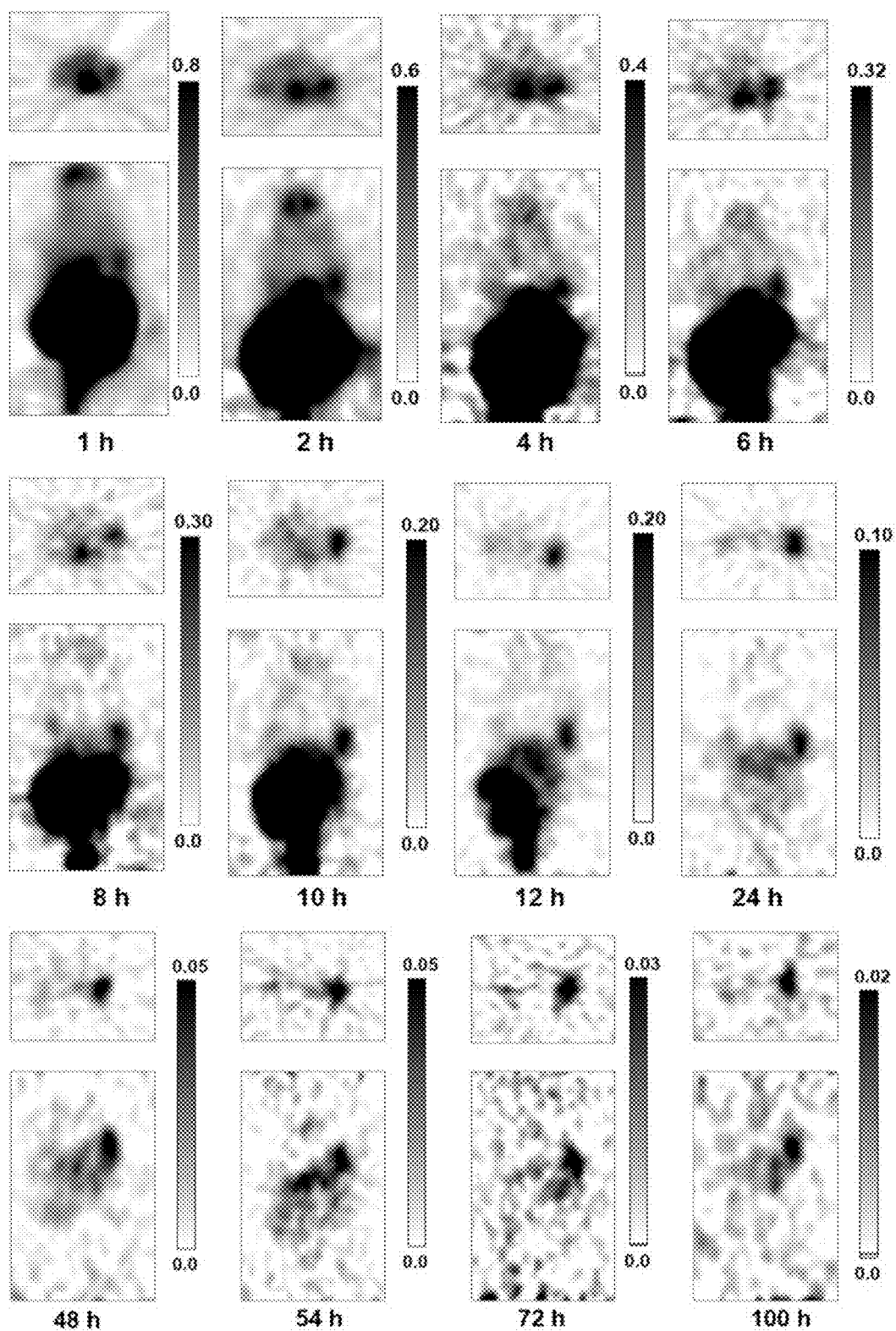

HSP90-TARGETED CARDIAC IMAGING AND THERAPY

CROSS REFERENCE TO RELATED APPLICATIONS

The present application claims priority to U.S. provisional patent application Ser. No. 61/799,106, filed Mar. 15, 2013, the entirety of which is hereby incorporated by reference herein.

BACKGROUND OF THE INVENTION

Cardiovascular disease, including diseases of the heart and its blood vessels, is the leading cause of death in the United States (www.cdc.gov/heartdisease/facts.htm). A variety of common diseases can impair blood flow to the heart and/or cardiac function (i.e., the ability of heart muscles to pump blood from the heart chambers). Notably, atherosclerosis is the most common disease of the blood vessels of the heart and a major cause of death in the U.S. Many types of cancer drugs are associated with cardiovascular toxicity involving inflammation of the heart and/or its blood vessels. Numerous other medical conditions are associated with impaired cardiac blood flow and/or cardiac function. Non-invasive medical imaging is the standard-of-care in the diagnosis and evaluation of impaired cardiac blood flow and/or cardiac function.

Standard clinical cardiac imaging modalities include nuclear imaging with specific labeled compounds for PET and SPECT (radiotracers); echocardiography; magnetic resonance imaging; and X-ray computed tomography with intravenous contrast material. For nuclear imaging, standard radiotracers include SPECT agents for evaluating cardiac blood flow (e.g., thallium-201; and technetium 99m-labeled sestamibi or tetrofosmin); PET agents for evaluation cardiac blood flow (e.g., nitrogen-13 ammonia; rubidium-82) and myocardial viability (e.g., fluorine-18 fluorodeoxyglucose); and SPECT and PET agents for evaluating cardiac function (e.g., technetium 99m-labeled red blood cells, as well as the aforementioned SPECT and PET tracers).

Targeted imaging for targeted therapy—using radiolabeled forms of targeted therapeutic agents for PET imaging—is much advocated for the future of medical imaging & drug development, by the National Cancer Institute and others. (National Cancer Institute, U.S. National Institutes of Health. A workshop regarding what in-vivo molecular imaging probes are needed to support future translational studies in cancer therapeutics. Paper presented at: Strategies for Imaging Priority Targets, 2002; Frankfurt, Germany; Weber W A, Czernin J, Phelps M E, Herschman H R. Technology Insight: novel imaging of molecular targets is an emerging area crucial to the development of targeted drugs. Nat Clin Pract Oncol. 2008; 5(1):44-54; Workman P, Aboagye E O, Chung Y L, Griffiths J R, Hart R, Leach M O, Maxwell R J, McSheehy P M, Price P M, Zweit J. Minimally invasive pharmacokinetic and pharmacodynamic technologies in hypothesis-testing clinical trials of innovative therapies. J Natl Cancer Inst. 2006; 98(9):580-598; Workman P, Burrows F, Neckers L, Rosen N. Drugging the cancer chaperone HSP90: combinatorial therapeutic exploitation of oncogene addiction and tumor stress Ann N Y Acad Sci. 2007; 1113:202-216). The unique potential of PET microdose studies in development of drugs as therapeutic and/or diagnostic imaging agents is recognized by the U.S. F.D.A and others. A review of published PET micro-dosing studies is provided by Wagner et al (Wagner C C, Müller M, Lappin G, Langer O. Positron emission tomography for use in microdosing studies. Curr Opin Drug Discov Devel. 2008 January; 11(1):104-10).

Each of the PET and SPECT tracers demonstrates specific limitations in their usefulness. Notably, SPECT imaging has inferior spatial resolution and sensitivity for detecting tracer in vivo, compared to PET imaging. As a result, PET imaging is better able to detect smaller areas of blood flow obstruction, in the heart; and PET imaging is better able to evaluate the wall motions (blood pumping/cardiac output function) of the heart, where the pumping function of the heart may be dysfunctional due to blood flow obstruction causing wall dysfunction or other causes. Exemplary limitations of standard cardiac PET include:

(A) PET technology is not yet accessible to all medical centers, particularly outside the U.S;

(B) certain PET tracers with short radioisotope half-lives (e.g., nitrogen-13 ammonia) are only available to medical centers with on-site cyclotrons (uncommon even inside the U.S.); and (C) because of their short half-lives, current PET cardiac blood-flow tracers can only be administered to patients receiving cardiac stress induced by a pharmacologic agent (e.g., adenosine), although physical exercise (e.g., treadmill) is the preferred method of inducing cardiac stress. Clinicians obtain important information from this physical exercise-induced stress, including cardiopulmonary performance data and electrocardiographic (EKG) data that are key in diagnosis of coronary artery disease and cardiac dysfunction and for determining patient prognosis. Because this cardiopulmonary and exercise-EKG information is so vital, cardiac imaging using SPECT tracers and physical exercise is often preferred to PET imaging (during pharmacological stress) for detection of cardiac disease, despite the superior imaging qualities of PET technology. These and other current clinical imaging modalities are limited in their abilities to evaluate cardiac blood flow and function, which may be impaired by a variety of medical conditions. In view of the extraordinary diagnostic value of cardiac imaging and the shortcomings of the technologies discussed above, there is a need for novel and improved methodologies for cardiac imaging.

BRIEF DESCRIPTION OF THE DRAWINGS

FIG. 3: Schema illustrating the study time-points for the $^{124}$I-PUH71 injection, PET-CT scans and blood draws. Shown are the minimum required time-points and additional time-points & repeat study that are optional for study participants. Time points refer to minutes (min) or hours (H) after injection of $^{124}$I-PUH71. The 0 minute PET-CT scan includes 1 CT scan that is applied to three consecutive rapidly-acquired PET scans, at 0 min, 10 min, and 20 minutes (30 minutes PET scanning total). PET scanning at each time-point last 30-45 minutes total.

SUMMARY OF THE INVENTION

Figure 1A:
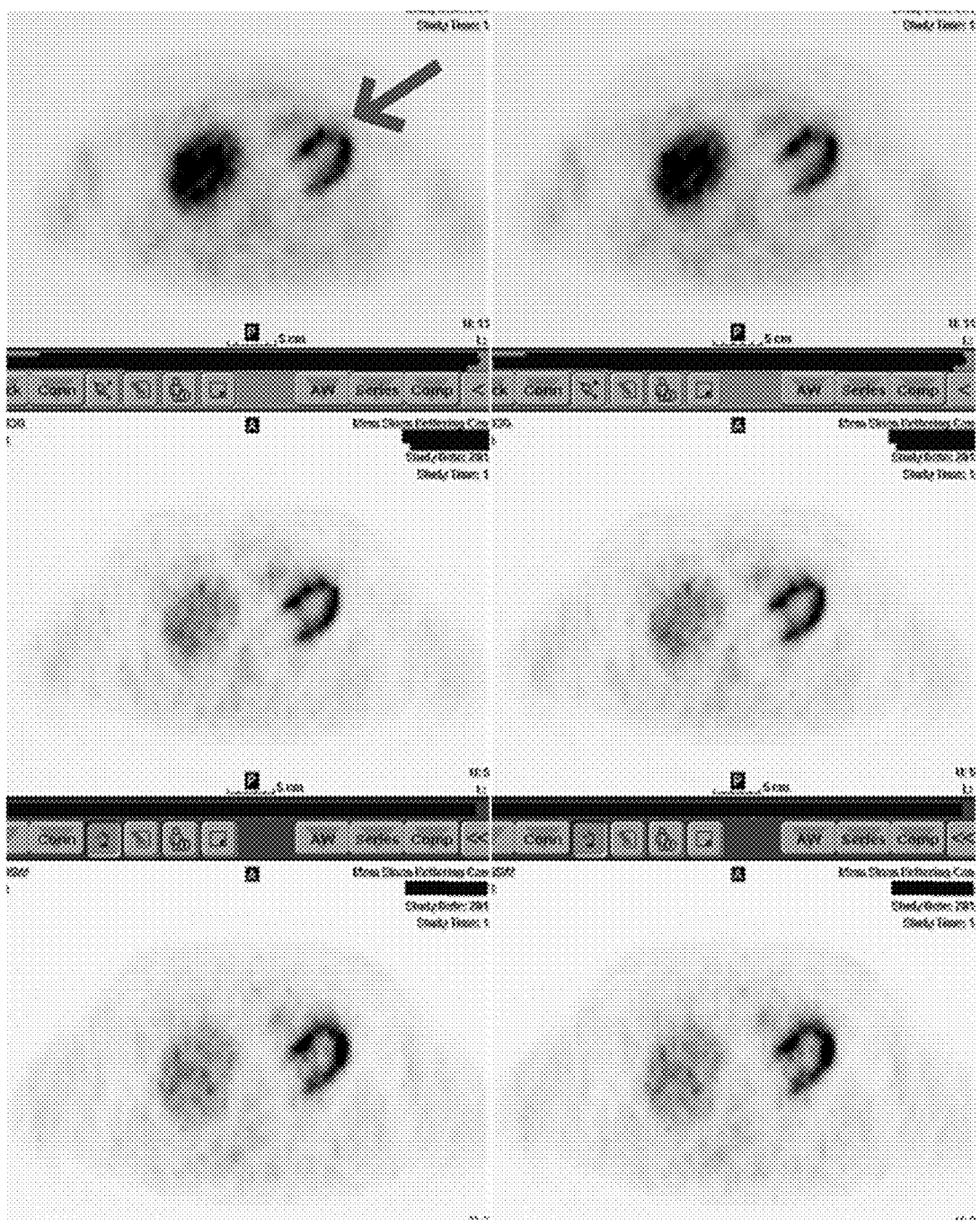
FIG. 1: a) PET images of a patient at multiple time points show distinct intake in the heart (arrow) at 3, 24, 48 hours after injection (top, middle, and bottom rows, respectively); b) Different patient showing the cardiac uptake (indicated by the dashmark) at different time points.

The present invention, among other things, encompasses the recognition that Hsp90 is implicated in mediating the pathophysiology of certain types of cardiac disease (e.g., dilated cardiomyopathy and ischemic heart disease; Kapustian, L. et al., Heart Vessels. 2013 January; 28(1):114-9), and that further understanding the role of Hsp90 in cardiac function can be valuable in the diagnosis and treatment of cardiac disease. In some embodiments, the present invention solves certain problems associated with conventional cardiac imaging as outlined above. For example, prior to the present invention, it was not feasible to perform non-invasive imaging of the human heart using an Hsp90-targeted imaging agent. In some embodiments, the present invention provides methods for non-invasive testing of cardiac blood flow, function, and viability. In certain embodiments, the present invention provides novel methods for monitoring, diagnosis and treatment of cardiovascular diseases, disorders and/or conditions. In some embodiments, provided methods comprise cardiac imaging using labeled compounds that bind to Hsp90, and/or labeled compounds having the structure of any of formula I to IX. In some embodiments, provided methods comprise cardiac imaging using labeled compounds that bind to Hsp90, and/or labeled compounds having the structure of formula I. In some embodiments, such methods provide non-invasive cardiac imaging that was previously not possible. In some embodiments, such methods provide for combinations of clinical techniques (e.g., PET scanning with physical exercise-induced cardiac stress) that were previously not compatible. In yet other embodiments the invention provides a method for detecting and treating cardiovascular disease, in that higher the uptake of the Hsp90-targeted imaging agent the more likely is the patient to benefit from Hsp90 therapy.

In some embodiments, the present invention provides a method for imaging cardiac tissue in a subject in need thereof, comprising steps of:
(a) administering to the subject a labeled compound that binds to Hsp90;
(b) imaging the cardiac tissue of the subject by detecting the labeled compound in the subject.

In some embodiments, the present invention provides a method for imaging cardiac tissue in a subject in need thereof, comprising steps of:
(a) administering to the subject an effective amount of a labeled compound of formula I:

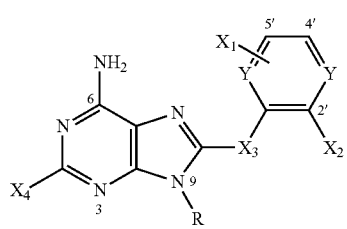

I or its pharmaceutically acceptable salt thereof, wherein:
Y is CH, N or O;
R is hydrogen, a $C_1$ to $C_{10}$ alkyl, alkenyl, alkynyl, or an alkoxyalkyl group, optionally comprising one or more heteroatoms, or a targeting moiety connected to N9 via a linker;
$X_4$ is hydrogen or halogen;
$X_3$ is $CH_2$, $CF_2$, S, SO, $SO_2$, O, NH, or $NR^2$, wherein $R^2$ is alkyl;
$X_2$ is halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$alkyl, COO-alkyl, $NH_2$, OH, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl or O-alkyl; and
$X_1$ represents two substituents, which may be the same or different, disposed in the 4' and 5' positions on the aryl group, wherein $X_1$ is selected from halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$-alkyl, COO-alkyl, $NH_2OH$, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl, or O-alkyl, $C_1$ to $C_6$ alkyl or alkoxy, or wherein $X_1$ has the formula —O—(CH$_2$)$_n$—O—, wherein n is an integer from 0 to 2, and one of the oxygens is bonded at the 5'-position and the other at the 4'-position of the aryl ring; and
wherein each hydrogen is optionally and independently substituted with a group that can be detected by a medical imaging technique, and/or at least one atom in the compound is optionally enriched in an isotope that can be detected by a medical imaging technique;
(b) imaging the cardiac tissue of the subject by detecting the labeled compound in the subject.

In some embodiments, the present invention provides a method for the diagnosis of cardiovascular diseases, conditions, or disorders comprising administering a labeled compound of any of formula I to IX to a subject in need thereof.

In some embodiments, the present invention provides a method for the treatment or prevention of cardiovascular diseases, conditions, or disorders comprising administering a compound of any of formula I to IX to a subject in need thereof.

In some embodiments, the present invention provides a method of monitoring the effect of cancer treatment on the heart comprising steps of:
(a) administering a labeled compound of any of formula I to IX to a subject who is scheduled for cancer treatment, currently undergoing cancer treatment, or has completed or discontinued cancer treatment; and
(b) imaging the cardiac tissue of the subject to detect the labeled compound; and
(c) recommending to the subject an appropriate avoidance, continuation, modification, or termination in cancer treatment.

In some embodiments, the present invention provides a method for monitoring a cancer treatment regimen, comprising steps of:
(a) administering a labeled compound of any of formula I to IX to a subject under a cancer treatment regimen;

(b) imaging the cardiac tissue of the subject by detecting the labeled compound in the subject;

(c) analyzing the images from step (b); and (d) maintaining, modifying or discontinuing the cancer treatment regimen.

In some embodiments, the present invention provides a method for selecting subjects for a test or treatment, comprising steps of:

(a) administering a labeled compound of any of formula I to IX to a subject;

(b) imaging the cardiac tissue of the subject by detecting the labeled compound in the subject;

(c) analyzing the images from step (b); and (d) including or excluding the subject for a test or a treatment.

In some embodiments, the present invention provides a method for determining the dosage of a drug, comprising steps of:

(a) administering a labeled compound of any of formula I to IX to a subject;

(b) imaging the cardiac tissue of the subject by detecting the labeled compound in the subject;

(c) analyzing the images from step (b); and (d) administering to the subject a suitable amount of a drug.

In some embodiments, the present invention provides a method for determining the risk of a cardiovascular disease, comprising steps of:

(a) administering a labeled compound of any of formula I to IX to a subject;

(b) imaging the cardiac tissue of the subject by detecting the labeled compound in the subject;

(c) analyzing the images from step (b); and (d) recommending to the subject additional diagnostic testing, a suitable treatment or preventive regimen.

In some embodiments, the present invention provides a method for assessing risk of a cardiovascular disease, comprising steps of:

(a) administering a labeled compound of any of formula I to IX to a subject;

(b) imaging the cardiac tissue of the subject by detecting the labeled compound in the subject;

(c) analyzing the images from step (b); and (d) recommending to the subject additional diagnostic testing, a suitable treatment or preventive regimen.

In some embodiments, the present invention provides a method for determining the risk of heart attack, comprising steps of:

(a) administering a labeled compound of any of formula I to IX to a subject;

(b) imaging the cardiac tissue of the subject by detecting the labeled compound in the subject;

(c) analyzing the images from step (b); and (d) recommending to the subject additional diagnostic testing, a suitable treatment or preventive regimen.

DEFINITIONS

Certain compounds of the present disclosure, and definitions of specific functional groups are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic, bicyclic or polycyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one double bond in which one or more hydrogen atoms are replaced with a substituent. Suitable substituents include those described below for a substituted aliphatic group.

The term "acyl," used alone or a part of a larger moiety, refers to groups formed by removing a hydroxy group from a carboxylic acid.

The term "halogen" means F, Cl, Br, or I.

The terms "aralkyl" and "arylalkyl" are used interchangeably and refer to alkyl groups in which a hydrogen atom has been replaced with an aryl group. Such groups include, without limitation, benzyl, cinnamyl, and dihydrocinnamyl.

The term "aryl" used alone or as part of a larger moiety as in "aralkyl," "aralkoxy," or "aryloxyalkyl," refers to monocyclic, bicyclic or polycyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic," as used herein, means aliphatic groups wherein one or more carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

As used herein, the terms "heterocycle," "heterocyclyl," "heterocyclic radical," and "heterocyclic ring" are used interchangeably and refer to a stable 3- to 14-membered monocyclic or 7-14-membered bicyclic or polycyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein and in the claims, the singular forms "a", "an", and "the" include the plural reference unless the context clearly indicates otherwise. Thus, for example, a reference to "a compound" includes a plurality of such compounds.

In another aspect, the present disclosure provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

Provided compounds may comprise one or more saccharide moieties. Unless otherwise specified, both D- and L-configurations, and mixtures thereof, are within the scope of the disclosure. Unless otherwise specified, both α- and β-linked embodiments, and mixtures thereof, are contemplated by the present disclosure.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the present disclosure.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present disclosure is not intended to be limited to these protecting groups; rather, a variety of additional equivalent protecting groups can be readily identified using the above criteria and utilized in the method of the present disclosure. Additionally, a variety of protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^{602}$; —(CH$_2$)$_{0-4}$OR°; —(CH$_2$)$_{0-4}$SR°; —(CH$_2$)$_{0-4}$S(O)R°; —(CH$_2$)$_{0-4}$S(O)$_2$R°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O—(CH$_2$)$_{0-1}$pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —PR°$_2$; —OPR°$_2$; —SiR°$_3$; —OSiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R°(or the ring formed by taking two independent occurrences of R°together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R°include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•$2, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O) R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

When used as a chemical bond, "⌇" shall be understood to depict a single carbon-carbon bond with undefined stereochemistry at a carbon center. Thus, a substituent attached to a carbon atom with a "⌇" bond refers to embodiments where the substituent is coming out of the plane of the paper, embodiments where the substituent is going behind the plane of the paper, and combinations (i.e., stereochemical mixtures) thereof.

As used herein, the term "labeled compound" refers to a compound that produces an enhanced signal compared to the compound prior to labeling when detected by a medical imaging technique. A labeled compound may have one or more "labels", which is an atom or moiety that leads to an enhanced signal. In some embodiments, a labeled compound is radiolabelled, wherein the labeled compound contains one or more enriched radioactive isotope of at least one element. Exemplary suitable isotopes include but are not limited to those used in positron emission tomography (PET), such as $^{124}$I, $^{11}$C, $^{15}$O, $^{13}$N, and $^{18}$F; and those used in single-photon emission computed tomography (SPECT). In some embodiments, a labeled compound is labeled with one or more non-radioactive labels. In some embodiments, a non-radioactive label can be detected by Magnetic Resonance Imaging (MRI). In some embodiments, the non-radioactive label is $^{19}$F. In some embodiments, a label is suited for MRI. In some embodiments, the label is a contrast agent. Many methods are known in the art for compound labeling. In some embodiments, a compound is labeled by substituting a hydrogen atom with a label. In some embodiments, a compound is labeled by substituting a hydrogen atom with a suitable fluorine or iodine label. In some embodiments, a suitable fluorine label is $^{18}$F. In some embodiments, a suitable fluorine label is $^{19}$F. In some embodiments, a suitable iodine label is $^{123}$I. In some embodiments, a suitable iodine label is $^{124}$I. In some embodiments, a suitable iodine label is $^{125}$I. In some embodiments, a suitable iodine label is $^{131}$I. In some embodiments, a label comprises more than one atom. In some other embodiments, a compound is labeled by altering the isotopic composition of one or more atoms, often by increasing the percentage of the isotope(s) that can be detected by the medical imaging technique to be used ("enriched"). In some embodiments, a labeled compound is isotopically enriched in one of $^{123}$I, $^{124}$I, $^{125}$I, $^{131}$I, $^{11}$C, $^{15}$O, $^{13}$N, and $^{18}$F or their combinations thereof. In some embodiments, a labeled compound is isotopically enriched in $^{123}$I. In some embodiments, a labeled compound is isotopically enriched in $^{124}$I. In some embodiments, a labeled compound is isotopically enriched in $^{125}$I. In some embodiments, a labeled compound is isotopically enriched in $^{131}$I. In some embodiments, a labeled compound is isotopically enriched in $^{11}$C. In some embodiments, a labeled compound is isotopically enriched in $^{15}$O. In some embodiments, a labeled compound is isotopically enriched in $^{13}$N. In some embodiments, a labeled compound is isotopically enriched in $^{18}$F. In some embodiments, a labeled compound comprises more than one label. In some embodiments, a labeled compound can be detected by one or more medical imaging techniques, for example but not limited to MRI, PET and SPECT. In some embodiments, a labeled compound comprises more than one radioactive label. In some embodiments, a labeled compound comprises more than one fluorine label. In some embodiments, a labeled compound comprises more than one $^{19}$F. In some embodiments, a label is a fluorophore moiety. In some embodiments, a label is a nanometer-sized agent. In some embodiments, a label is a nanoparticle. In some embodiments, a label is a nanotube. In some embodiments, a label is liposome. In some embodiments, a nanotube or liposome comprises a moiety that produces an enhanced signal. In some embodiments, one or more MRI agents are linked or packaged in a nanotube, nanoparticle or liposome. In some embodiments, one nanometer-sized agent or nanoparticle or liposomal micelle is used to label more than one molecule of a compound to be labeled; for example, more than one molecule of the compound to be labeled can be linked to a single nanoparticle. In some embodiments, a label is covalently linked to a compound. In some embodiments, a label is non-covalently linked to a compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "palliative" refers to treatment that is focused on the relief of symptoms of a disease and/or side effects of a therapeutic regimen, but is not curative.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition. Daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

The expression "unit dose" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/ or additional therapies used in combination or coincidental with specific compound(s) employed, and like factors well known in the medical arts. A particular unit dose may or may not contain a therapeutically effective amount of a therapeutic agent.

An individual who is "suffering from" a disease, disorder, and/or condition has been diagnosed with and/or displays one or more symptoms of the disease, disorder, and/or condition.

An individual who is "susceptible to" a disease, disorder, and/or condition has not been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

DETAILED DESCRIPTION OF CERTAIN EMBODIMENTS

The present invention encompasses the recognition of the importance to develop new methods for imaging cardiac tissue, for the diagnosis, treatment or prevention of cardiovascular diseases, conditions, or disorders, for monitoring the effect of cancer treatment, for selecting subjects for a test or treatment, for determining drug dosages, and for determining the risk of heart attack. The present invention provides, among other things, novel methods for the aforementioned purposes.

Existing methods employ compounds that (a) evaluate only cardiac function or viability, and/or (b) are available only as SPECT tracers. In some embodiments, provided methods employ compounds that (a) offer the first comprehensive evaluation of cardiac blood flow, function, and viability, and/or (b) are useful as PET tracers.

Hsp90 is associated with cardiovascular physiology and pathophysiology, but no non-invasive clinical biomarkers of cardiac Hsp90 are available. In some embodiments, the present invention provides the first non-invasive methods of assaying cardiac Hsp90. In some embodiments, the present invention provides non-invasive methods of assaying cardiac functions related to Hsp90. In some embodiments, the present invention provides non-invasive methods of assaying cardiac functions that are unrelated to Hsp90. In some embodiments, the present invention provides non-invasive cardiac assays of cardiac blood flow and cardiac function, including cardiovascular conditions in which Hsp90 does or does not have a primary role.

As previously described by Applicant in WO/2013/009655, the entire contents of which are incorporated herein by reference, oncogenic Hsp90 is a cell stress specific form of Hsp90 that is expanded and constitutively maintained in the tumor cell context, and that may execute functions necessary to maintain the malignant phenotype. Without wishing to be bound by any particular theory, it is believed that the same cell stress specific form of Hsp90 observed in the tumor context can also be observed in stressed cardiac tissue (i.e., stress-specific Hsp90) using methods provided herein. In such a case, it is believed that cardiac tissue comprising stress-specific Hsp90 has a greater likelihood of benefiting from treatment with Hsp90 inhibitors. In some embodiments, provided methods are useful for detecting and treating cardiovascular conditions, disorders, or diseases, wherein a higher uptake of an Hsp90-targeting imaging agent indicates a higher likelihood a patient will benefit from Hsp90 inhibitor therapy. "Stress-specific Hsp90" as used herein means a form of Hsp90 expressed in response to cardiac tissue stress. In some embodiments, cardiac tissue stress may be environmental or caused by a cardiovascular disease, disorder, or condition, chemotherapy-induced toxicity or inflammation, or infectious disease.

In some embodiments, the present invention provides a method for imaging cardiac tissue in a subject in need thereof, comprising steps of:
(a) administering to the subject a labeled compound that binds to Hsp90;
(b) imaging the cardiac tissue of the subject by detecting the labeled compound in the subject.

In some embodiments, the present invention provide a method for imaging cardiac tissue in a subject in need thereof, comprising steps of:
(a) administering to the subject an effective amount of a labeled compound of formula I, wherein the compound of formula I has the structure of:

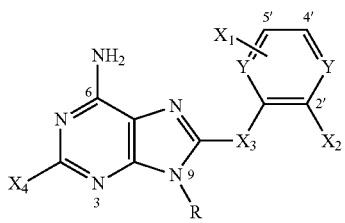

I or its pharmaceutically acceptable salt thereof, wherein:
Y is CH, N or O;
R is hydrogen, a $C_1$ to $C_{10}$ alkyl, alkenyl, alkynyl, or an alkoxyalkyl group, optionally comprising one or more heteroatoms, or a targeting moiety connected to N9 via a linker;
$X_4$ is hydrogen or halogen;
$X_3$ is $CH_2$, $CF_2$, S, SO, $SO_2$, O, NH, or $NR^2$, wherein $R^2$ is alkyl;
$X_2$ is halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$alkyl, COO-alkyl, $NH_2$, OH, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl or O-alkyl; and
$X_1$ represents two substituents, which may be the same or different, disposed in the 4' and 5' positions on the aryl group, wherein $X_1$ is selected from halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$-alkyl, COO-alkyl, $NH_2OH$, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl, or O-alkyl, $C_1$ to $C_6$ alkyl or alkoxy, or wherein $X_1$ has the formula —O—$(CH_2)_n$—O—, wherein n is an integer from 0 to 2, and one of the oxygens is bonded at the 5'-position and the other at the 4'-position of the aryl ring; and (b) imaging the cardiac tissue of the subject by detecting the labeled compound in the subject.

In some embodiments, the present invention provide a method for imaging cardiac tissue in a subject in need thereof, comprising steps of:
(a) administering to the subject an effective amount of a labeled compound of formula I:

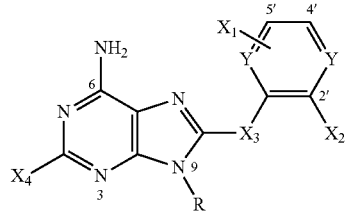

I or its pharmaceutically acceptable salt thereof, wherein:
Y is CH, N or O;
R is hydrogen, a $C_1$ to $C_{10}$ alkyl, alkenyl, alkynyl, or an alkoxyalkyl group, optionally comprising one or more heteroatoms, or a targeting moiety connected to N9 via a linker;
$X_4$ is hydrogen or halogen;
$X_3$ is $CH_2$, $CF_2$, S, SO, $SO_2$, O, NH, or $NR^2$, wherein $R^2$ is alkyl;
$X_2$ is halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$alkyl, COO-alkyl, $NH_2$, OH, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl or O-alkyl; and
$X_1$ represents two substituents, which may be the same or different, disposed in the 4' and 5' positions on the aryl group, wherein $X_1$ is selected from halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$-alkyl, COO-alkyl, $NH_2OH$, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl, or O-alkyl, $C_1$ to $C_6$ alkyl or alkoxy, or wherein $X_1$ has the formula —O—$(CH_2)_n$—O—, wherein n is an integer from 0 to 2, and one of the oxygens is bonded at the 5'-position and the other at the 4'-position of the aryl ring; and
wherein each hydrogen is optionally and independently substituted with a group that can be detected by a medical imaging technique, and/or at least one atom is optionally enriched in an isotope that can be detected by a medical imaging technique;
(b) imaging the cardiac tissue of the subject by detecting the labeled compound in the subject.

In some embodiments, a compound of formula I binds to Hsp90. In some embodiments, a compound of formula I is an Hsp90 inhibitor.

In some embodiments, a labeled compound of formula I is a labeled compound having the structure of formula II,

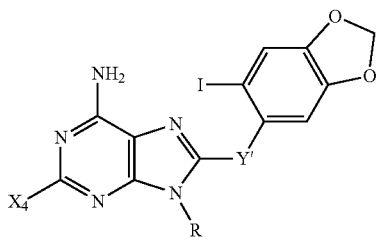

(II)

wherein Y' is —CH$_2$— or S;

X$_4$ is hydrogen or halogen; and R is an amino alkyl moiety, optionally substituted on the amino nitrogen with one or two carbon-containing substituents selected independently from the group consisting of alkyl, alkenyl and alkynyl substituents, wherein the total number of carbons in the amino alkyl moiety is from 1 to 9.

In some embodiments, the present invention provides a method for imaging cardiac tissue in a subject in need thereof, comprising steps of:

(a) administering to the subject an effective amount of a labeled compound of formula III or IV:

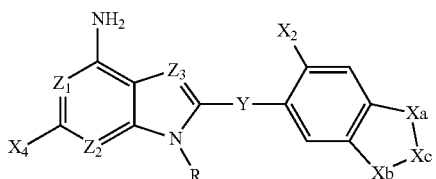

(III)

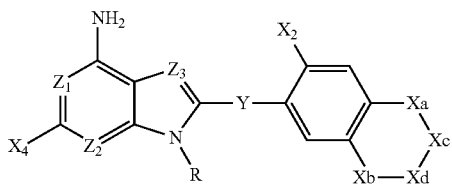

(IV)

or a pharmaceutically acceptable salt thereof, wherein:
(a) each of Z$_1$, Z$_2$ and Z$_3$ is independently CH or N;
(b) Y is CH$_2$, O, or S;
(c) Xa, Xb, Xc and Xd are independently selected from CH, CH$_2$, O, N, NH, S, carbonyl, fluoromethylene, and difluoromethylene selected so as to satisfy valence, wherein each bond to an X group is either a single bond or a double bond;
(d) X$_2$ is $^{123}$I, $^{124}$I, $^{125}$I or $^{131}$I;
(e) X$_4$ is hydrogen or halogen; and
(f) R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl, wherein the R group is optionally interrupted by —S(O)N(R$_A$)—, —NR$_A$S(O)—, —SO$_2$N(R$_A$)—, —NR$_A$SO$_2$—, —C(O)N(R$_A$)—, or —NR$_A$C(O)—, and/or the R group is optionally terminated by —S(O)NR$_A$R$_B$, —NR$_A$S(O)R$_B$, —SO$_2$NR$_A$R$_B$, —NR$_A$SO$_2$R$_B$, —C(O)NR$_A$R$_B$, or —NR$_A$C(O)R$_B$, wherein each R$_A$ and R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and (b) imaging the cardiac tissue of the subject by detecting the labeled compound in the subject.

In some embodiments, the present invention provides a method for imaging cardiac tissue in a subject in need thereof, comprising steps of:

(a) administering to the subject an effective amount of a labeled compound of formula III or IV:

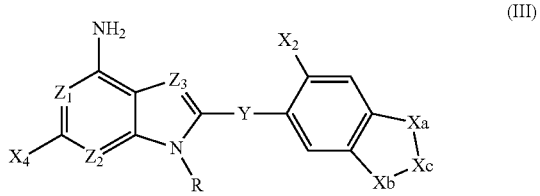

(III)

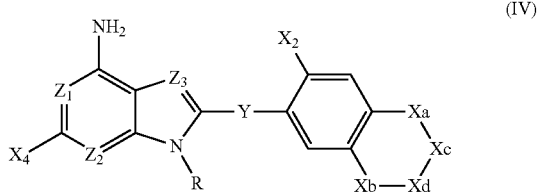

(IV)

or a pharmaceutically acceptable salt thereof, wherein:
(a) each of Z$_1$, Z$_2$ and Z$_3$ is independently CH or N;
(b) Y is CH$_2$, O, or S;
(c) Xa, Xb, Xc and Xd are independently selected from CH, CH$_2$, O, N, NH, S, carbonyl, fluoromethylene, and difluoromethylene selected so as to satisfy valence, wherein each bond to an X group is either a single bond or a double bond;
(d) X$_2$ is $^{123}$I, $^{124}$I, $^{125}$I or $^{131}$I;
(e) X$_4$ is hydrogen or halogen; and
(f) R is —(CH$_2$)$_m$—N—R$_{10}$R$_{11}$R$_{12}$ or —(CH$_2$)$_m$—N—R$_{10}$R$_{11}$, where m is 2 or 3 and where R$_{10}$-R$_{12}$ are independently selected from hydrogen, methyl, ethyl, ethenyl, ethynyl, propyl, hydroxyalkyl, isopropyl, t-butyl, isobutyl, cyclopentyl, a 3-membered ring including the nitrogen or a 6-membered ring including the N and optionally an additional heteroatom with substituents to satisfy valence, with the proviso that when all of R$_{10}$-R$_{12}$ are present the compound further comprises a pharmaceutically acceptable counter ion; and (b) imaging the cardiac tissue of the subject by detecting the labeled compound in the subject.

In some embodiments, the present invention provides a method for imaging cardiac tissue in a subject in need thereof, comprising steps of:

(a) administering to the subject an effective amount of a labeled compound of formula V:

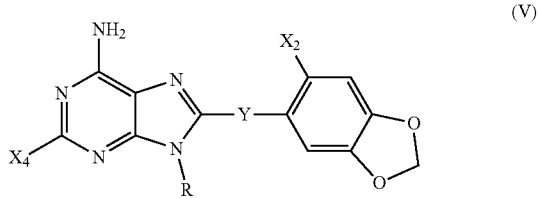

(V)

or a pharmaceutically acceptable salt thereof, wherein:
Y is $CH_2$ or S;
$X_4$ is H or halogen
$X_2$ is $^{123}I$, $^{124}I$, $^{125}I$ or $^{131}I$; and
R is —$(CH_2)_m$—N—$R_{10}R_{11}R_{12}$ or —$(CH_2)_m$—N—$R_{10}R_{11}$, where m is 2 or 3 and where $R_{10}$—$R_{12}$ are independently selected from hydrogen, methyl, ethyl, ethenyl, ethynyl, propyl, hydroxyalkyl, isopropyl, t-butyl, isobutyl, cyclopentyl, a 3-membered ring including the nitrogen or a 6-membered ring including the N and optionally an additional heteroatom with substituents to satisfy valence, with the proviso that when all of $R_{10}$-$R_{12}$ are present the compound further comprises a pharmaceutically acceptable counter ion; and
(b) imaging the cardiac tissue of the subject by detecting the labeled compound in the subject.

In some embodiments, the present invention provides a method for imaging cardiac tissue in a subject in need thereof, comprising steps of:
(a) administering to the subject an effective amount of a labeled compound of formula VI:

(VI)

<chemical structure> or a pharmaceutically acceptable salt thereof, wherein:
Y is $CH_2$ or S;
$X_4$ is H or halogen;
$X_2$ is $^{123}I$, $^{124}I$, $^{125}I$ or $^{131}I$; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide; and (b) imaging the cardiac tissue of the subject by detecting the labeled compound in the subject.

In some embodiments, the present invention provide a method for imaging cardiac tissue in a subject in need thereof, comprising steps of:
(a) administering to the subject an effective amount of a labeled compound of formula VII:

(VII)

<chemical structure> or a pharmaceutically acceptable salt thereof, wherein:
one of Xa and Xb is O and the other is $CH_2$;
Y is $CH_2$ or S;
$X_4$ is hydrogen or halogen; and
$X_2$ is $^{123}I$, $^{124}I$, $^{125}I$ or $^{131}I$; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide; and (b) imaging the cardiac tissue of the subject by detecting the labeled compound in the subject.

In some embodiments, the present invention provides a method for imaging cardiac tissue in a subject in need thereof, comprising steps of:
(a) administering to the subject an effective amount of a labeled compound of formula VIII:

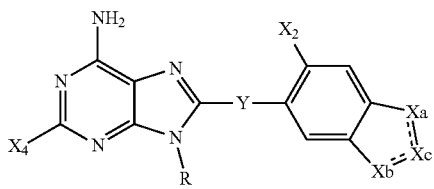

(VIII)

or a pharmaceutically acceptable salt thereof, wherein:
Xa-Xc-Xb is $CH_2$—$CH_2$—$CH_2$, CH=CH—$CH_2$, or $CH_2$—CH=CH;
Y is $CH_2$ or S;
$X_2$ is $^{123}$I, $^{124}$I, $^{125}$I or $^{131}$I; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide; and
(b) imaging the cardiac tissue of the subject by detecting the labeled compound in the subject.

In some embodiments, the present invention provides a method for imaging cardiac tissue in a subject in need thereof, comprising steps of:
(a) administering to the subject an effective amount of a labeled compound of formula IX:

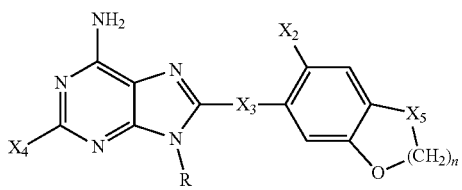

(IX)

or a pharmaceutically acceptable salt thereof, wherein:
$X_3$ is $CH_2$, $CF_2$, S, SO, $SO_2$, O, NH, or $NR^2$, wherein $R^2$ is alkyl;
$X_2$ is $^{123}$I, $^{124}$I, $^{125}$I or $^{131}$I;
$X_4$ is hydrogen or halogen;
$X_5$ is O or $CH_2$;
R is 3-isopropylaminopropyl, 3-(isopropyl(methyl)amino)propyl, 3-(isopropyl(ethyl)amino)propyl, 3-((2-hydroxyethyl)(isopropyl)amino)propyl, 3-(methyl(prop-2-ynyl)amino)propyl, 3-(allyl(methyl)amino)propyl, 3-(ethyl(methyl)amino)propyl, 3-(cyclopropyl(propyl)amino)propyl, 3-(cyclohexyl(2-hydroxyethyl)amino)propyl, 3-(2-methylaziridin-1-yl)propyl, 3-(piperidin-1-yl)propyl, 3-(4-(2-hydroxyethyl)piperazin-1-yl)propyl, 3-morpholinopropyl, 3-(trimethylammonio)propyl, 2-(isopropylamino)ethyl, 2-(isobutylamino)ethyl, 2-(neopentylamino)ethyl, 2-(cyclopropylmethylamino)ethyl, 2-(ethyl(methyl)amino)ethyl, 2-(isobutyl(methyl)amino)ethyl, or 2-(methyl(prop-2-ynyl)amino)ethyl; and
n is 1 or 2;
(b) imaging the cardiac tissue of the subject by detecting the labeled compound in the subject.

In some embodiments, a compound of formula I binds to Hsp90. In some embodiments, a compound of formula I is an Hsp90 inhibitor. In some embodiments, a compound of formula II binds to Hsp90. In some embodiments, a compound of formula II is an Hsp90 inhibitor. In some embodiments, a compound of formula III binds to Hsp90. In some embodiments, a compound of formula III is an Hsp90 inhibitor. In some embodiments, a compound of formula IV binds to Hsp90. In some embodiments, a compound of formula IV is an Hsp90 inhibitor. In some embodiments, a compound of formula V binds to Hsp90. In some embodiments, a compound of formula V is an Hsp90 inhibitor. In some embodiments, a compound of formula VI binds to Hsp90. In some embodiments, a compound of formula VI is an Hsp90 inhibitor. In some embodiments, a compound of formula VII binds to Hsp90. In some embodiments, a compound of formula VII is an Hsp90 inhibitor. In some embodiments, a compound of formula VIII binds to Hsp90. In some embodiments, a compound of formula VIII is an Hsp90 inhibitor. In some embodiments, a compound of formula IX binds to Hsp90. In some embodiments, a compound of formula IX is an Hsp90 inhibitor.

Hsp90 may have multiple isoforms. In some embodiments, the labeled compound binds to one or more isoforms of Hsp90. In some embodiments, the labeled compound binds to one or more isoforms of Hsp90 expressed in cardiac tissue. In some embodiments, the labeled compound binds to one form of Hsp90. In some embodiments, the labeled compound binds to more than one form of Hsp90. In some embodiments, the labeled compound binds to more than one form of Hsp90 with comparable affinity. In some embodiments, the labeled compound binds to more than one form of Hsp90 with different affinity.

In some embodiments, Hsp90 is stress-specific Hsp90.

In some embodiments, a labeled compound binds to Hsp90 with a $K_D$ of less than about 1 mM, about 100 μM, about 10 μM or about 1 μM. In some embodiments, a labeled compound binds to Hsp90 with a $K_D$ of less than about 1 mM. In some embodiments, a labeled compound binds to Hsp90 with a $K_D$ of less than about 100 μM. In some embodiments, a labeled compound binds to Hsp90 with a $K_D$ of less than about 10 μM. In some embodiments, a labeled compound binds to Hsp90 with a $K_D$ of less than about 1 μM.

In some embodiments, a labeled compound inhibits Hsp90. In some embodiments, a labeled compound has an $IC_{50}$ of less than about 1 mM, about 100 μM, about 10 μM or about 1 µM. In some embodiments, a labeled compound has an $IC_{50}$ of less than about 1 mM. In some embodiments, a labeled compound has an $IC_{50}$ of less than about 100 µM. In some embodiments, a labeled compound has an $IC_{50}$ of less than about 10 µM. In some embodiments, a labeled compound has an $IC_{50}$ of less than about 1 µM.

In some embodiments, a labeled compound binds to stress-specific Hsp90. In some embodiments, a labeled compound specifically binds to stree-specific Hsp90. In some embodiments, a labeled compound inhibits stress-specific Hsp90. In some embodiments, a labeled compound specifically inhibits stree-specific Hsp90.

In some embodiments, a labeled compound that binds to Hsp90 has the structure of formula I. In some embodiments, a labeled compound that binds to Hsp90 has the structure of formula II. In some embodiments, a labeled compound that binds to Hsp90 has the structure of formula III. In some embodiments, a labeled compound that binds to Hsp90 has the structure of formula IV. In some embodiments, a labeled compound that binds to Hsp90 has the structure of formula V. In some embodiments, a labeled compound that binds to Hsp90 has the structure of formula VI. In some embodiments, a labeled compound that binds to Hsp90 has the structure of formula VII. In some embodiments, a labeled compound that binds to Hsp90 has the structure of formula VIII. In some embodiments, a labeled compound that binds to Hsp90 has the structure of formula IX.

Exemplary assays for measuring binding and/or inhibition of Hsp90 are widely known in the art, for example but not limited to those described in U.S. Pat. No. 7,834,181 and its cited references thereof, the entirety of each of which is hereby incorporated by reference.

Suitable imaging technologies are widely known and practiced in the art. In some embodiments, the imaging process in step (b) comprises tomography. In some embodiments, the imaging process comprises positron emission tomography (PET). In some embodiments, the imaging process comprises single-photon emission computed tomography (SPECT). In some embodiments, the imaging process comprises more than one technique. In some embodiments, the imaging process comprises PET combined with another imaging technique. In some embodiments, PET is combined with X-ray Computed Tomography (CT), Magnetic Resonance Imaging (MRI) or single-photon emission computed tomography (SPECT). In some embodiments, the imaging process comprises PET-CT. In some embodiments, the imaging process comprises PET-MRI. In some embodiments, the imaging process comprises PET-SPECT.

In some embodiments, a provided method further comprises collecting electrocardiography (ECG) data. ECG data can be collected prior to, concurrent with, and/or subsequent to the imaging process. In some embodiments, ECG data, among other purposes, are used to solve imaging problems caused by heart motion. ECG-gated imaging is widely known and practiced in the art to improve imaging results including resolution.

In some embodiments, detecting the labeled compound in the subject comprises measuring signal intensity from the heart of the subject. In some embodiments, the intensity is measured through radioactivity, when the labeled compound comprises one or more radioactive label. In some embodiments, the labeled compound has better retention in cardiac tissues so that the cardiac tissues have relatively higher signal intensity compared to surrounding tissues or organs.

In some embodiments, a subject is a cancer patient. In some embodiments, a subject is not a cancer patient.

In some embodiments, the imaging is performed at one time point. In some embodiments, the imaging is performed at more than one time point. In some embodiments, the imaging is performed at about 0 min, 5 min, 10 min, 15 min, 20 min, 25 min, 30 min, 45 min, 1 hour, 2 hours, 3 hours, 6 hours, 12 hours, 24 hours, 36 hours, 48 hours, 60 hours, 72 hours, 5 days, 6 days, 1 week post-administration of the labeled compound. In some embodiments, the imaging is performed at about 0-30 minutes post-administration of the labeled compound. In some embodiments, the imaging is performed at about 10-60 minutes post-administration of the labeled compound. In some embodiments, the imaging is performed at about 10 min-3 hours post-administration of the labeled compound. In some embodiments, the imaging is performed at about 10 min-6 hours post-administration of the labeled compound. In some embodiments, the imaging is performed at about 10 min-12 hours post-administration of the labeled compound. In some embodiments, the imaging is performed at about 10 min-24 hours post-administration of the labeled compound. In some embodiments, the imaging is performed at about 10 min-36 hours post-administration of the labeled compound. In some embodiments, the imaging is performed at about 10 min-48 hours post-administration of the labeled compound. In some embodiments, the imaging is performed at about 10 min-72 hours post-administration of the labeled compound. In some embodiments, the imaging is performed after about 72 hours post-administration of the labeled compound.

The imaging process provides valuable medical information useful for many purposes, including but not limited to diagnosis, treatment, prevention and stratification. The imaging process provides valuable medical information useful for many purposes, including but not limited to diagnosis, treatment, prevention and stratification of patient risk of cardiovascular morbidity and mortality. In some embodiments, the imaging detects cardiac blood flow. In some embodiments, the imaging detects cardiac blood flow, wherein tissues exposed to more blood flow produce higher signal intensity. In some embodiments, the imaging detects cardiac function.

In some embodiments, a provided method further comprises a step comprising comparing an image from step b to a reference. In some embodiments, a reference is the image of the healthy cardiac tissue within the image. In some embodiments, a reference is an image taken at a different time point. In some embodiments, a reference is an image taken without cardiac stress. In some embodiments, a reference is the "average" image of a population. In some embodiments, a reference is the average image of a healthy population. In some embodiments, a reference is the average image of a population with a cardiovascular disease, condition or disorder.

In some embodiments, a provided method further comprises a step that includes comparing an image from step b to a reference. In some embodiments, a reference is a portion of the healthy cardiac tissue within the image. In some embodiments, a reference is an image taken at a different time point. In some embodiments, a reference is an image taken without cardiac stress. In some embodiments, a reference is an average image, wherein the data for each point of the image are the average of the data for that point in two or more images that are averaged. In some embodiments, a reference is an average image of a population. In some embodiments, a reference is an average image of a healthy population. In some embodiments, a reference is an average image of a population with a cardiovascular disease, condition, or disorder. In some embodiments, an average image is constructed by averaging the signal intensity of each subject in a population for every position of the image.

In some embodiments, a provided method further comprises a step that includes comparing the data of a first cardiac position of an image obtained in step b) to those of a second cardiac position, wherein the second cardiac position is from another cardiac image or a different position of the same cardiac image. In some embodiments, a provided method further comprises a step that includes comparing the data of a first cardiac position of an image obtained in step b) to those of a second cardiac position, wherein the second cardiac position is from another cardiac image. In some embodiments, a provided method further comprises a step that includes comparing the data of a first cardiac position of an image obtained in step b) to those of a second cardiac position, wherein the second cardiac position is a different position of the same cardiac image. In some embodiments, the comparison is a direct comparison. In some embodiments, the comparison is an indirect comparison. In some embodiments, the comparison is an indirect comparison, wherein at least one of the first and second positions is compared to a reference. In some embodiments, a reference is from an average cardiac image.

Unless otherwise specified, "imaging" refers to a process of collecting data using a medical imaging device, and an "image" refers to a set of collected data. The set of collected data can be collected, transmitted, stored, processed, analyzed or presented in various formats, including but not limited to visual pictures.

As understood by a person of ordinary skill in the art, in some embodiments, a stronger cardiac image signal indicates relatively more blood flow in that region. Measuring of signal intensity in images produced from various medical techniques is a standard practice known by a person of ordinary skill in the art. In some embodiments, computer software, sometimes commercially available and/or installed with an imaging instrumentation system, is used to analyze signals collected by an imaging system, including quantitative and qualitative comparison with a reference point and/or a reference image. In some embodiments, a lack of signal, or decreased intensity of signal, when compared to one or more reference points and/or one or more reference images, indicates relatively less blood flow in the location that lacks the signal or has decreased intensity of signal.

It will be appreciated that as a general matter, as with conventional tracers, cardiac imaging as described herein shows where blood has flowed in the heart tissue. For example, it is expected that more tracer will be present in normal, healthy tissue, relative to tissue where some sort of vessel constriction or injury limits the delivery of tracer. Therefore, in general, images collected in accordance with the provided methods are interpreted in the conventional fashion in the field of nuclear medicine, e.g., less tracer is indicative of constriction or damage. A physician, upon analyzing and interpreting these results, can then make the medically relevant descisions and recommendations on proper treatment.

In some embodiments, Hsp90 is upregulated in areas of cardiac damage. Therefore, without wishing to be bound by any particular theory, it is believed that an increase in signal could be realized in such instances where a labeled Hsp90 inhibitor is used, particularly one that selectively binds cardiac-stress specific Hsp90. In such cases, increased uptake of tracer might indicate a damaged area.

One skilled in the art of nuclear medicine will also be able to differentiate, upon analysis of images, whether lower relative signal is due to scar tissue or poor blood flow. For example, upon comparing images before and after a stress test, if a cardiac region has relatively less gain of signal in an area compared to healthy tissue, it suggests that area suffers from "stress ischemia" due to a constriction. On the other hand, if upon comparison an area is shown to have relatively low or no signal both before and after a stress test, it suggests scar tissue is present.

In some embodiments, the imaging can be used to diagnose, evaluate, or predict risk of patient morbidity or mortality due to cardiovascular diseases, disorders, or conditions affecting: myocardial blood flow (e.g., coronary atherosclerosis); myocardial viability (e.g., prior myocardial infarction); myocardial function (e.g., cardiomyopathy caused by cancer chemotherapy toxicity, coronary atherosclerosis, or other causes); ejection of blood from the heart or from one of its anatomic chambers (e.g., poor cardiac output due to cardiomyopathy); and/or cardiovascular disease associated expression of Hsp90, or combinations thereof. In some embodiments, the cardiovascular disease, disorder, or condition is selected from the group consisting of coronary artery disease (including but not limited to atherosclerosis), prior myocardial infarction, cardiomyopathy, and poor cardiac output.

In some embodiments, a cardiovascular disease, disorder, or condition is caused by another disease, or the treatment of another disease, such as cancer therapy.

In some embodiments, the cardiovascular disease, disorder or condition is associated with Hsp90. In some other embodiments, the cardiovascular disease, disorder or condition is not associated with Hsp90. In some embodiments, a provided cardiac imaging method is performed for the diagnosis, treatment, prevention or monitoring of a disease, disorder or condition on a subject irrespective of the role of Hsp90 in the said disease, disorder or condition.

In some embodiments, the labeled compound is co-administered with a non-radioactive therapeutic compound. In some embodiments, the labeled compound has the same structure as the non-radioactive therapeutic compound but is labeled by the enrichment of one or more radioactive isotopes of one or more elements. In some embodiments, the labeled compound is administered concurrently with the non-labeled compound. In some embodiments, the labeled compound is administered prior to the non-labeled compound. In some embodiments, the labeled compound is administered subsequent to the non-labeled compound. In some embodiments, concurrent administration uses a formulation comprising a mixture of labeled compound and non-radioactive compound. In some embodiments, the labeled and non-radioactive therapeutic compound are co-administered but via different routes and/or sites of administration. In some embodiments the non-labeled compound is an hsp90 inhibitor.

In some embodiments, imaging of the labeled compound, among other things, provides the distribution of the co-administered therapeutic compound in cardiac tissues. In some embodiments, the imaging measures the accessibility of cardiac Hsp90 to a therapeutic compound. In some embodiments, the imaging measures the concentrations of a therapeutic compound in the cardiac tissue. In some embodiments, the imaging measures the occupancy or saturation of cardiac Hsp90 achieved by a therapeutic compound. In some embodiments, the imaging measures the ability of the therapeutic compound to displace the labeled imaging agent.

The radioactive isotopes of radiolabeled compounds decay with time. As known by a person having ordinary skill in the art, for different purposes radiolabeled compounds with different half-life can be used. In some embodiments, a radioactive label or a radiolabeled compound has a half-life of at least about 0.1, 0.2, 0.5, 1, 2, 3, 4, 5, 6, 7, 8, 9, 10, 11, 12, 18, 24, 36, 48, 72, 96, or 100.3 hours. In some embodiments, a radioactive label or a radiolabeled compound has a half-life of at least about 1 hour. In some embodiments, a radioactive label or a radiolabeled compound has a half-life of at least about 2 hours. In some embodiments, a radioactive label or a radiolabeled compound has a half-life of at least about 3 hours. In some embodiments, a radioactive label or a radiolabeled compound has a half-life of at least about 4 hours. In some embodiments, a radioactive label or a radiolabeled compound has a half-life of at least about 5 hours. In some embodiments, a radioactive label or a radiolabeled compound has a half-life of at least about 6 hours. In some embodiments, a radioactive label or a radiolabeled compound has a half-life of at least about 7 hours. In some embodiments, a radioactive label or a radiolabeled compound has a half-life of at least about 8 hours. In some embodiments, a radioactive label or a radiolabeled compound has a half-life of at least about 9 hours. In some embodiments, a radioactive label or a radiolabeled compound has a half-life of at least about 10 hours. In some embodiments, a radioactive label or a radiolabeled compound has a half-life of at least about 11 hours. In some embodiments, a radioactive label or a radiolabeled compound has a half-life of at least about 12 hours. In some embodiments, a radioactive label or a radiolabeled compound has a half-life of at least about 18 hours. In some embodiments, a radioactive label or a radiolabeled compound has a half-life of at least about 24 hours. In some embodiments, a radioactive label or a radiolabeled compound has a half-life of at least about 36 hours. In some embodiments, a radioactive label or a radiolabeled compound has a half-life of at least about 48 hours. In some embodiments, a radioactive label or a radiolabeled compound has a half-life of at least about 72 hours. In some embodiments, a radioactive label or a radiolabeled compound has a half-life of at least about 96 hours. In some embodiments, a radioactive label or a radiolabeled compound has a half-life of about 59.4 days. In some embodiments, a radioactive label or a radiolabeled compound has a half-life of about 8.0 days. In some embodiments, a radiolabelled compound comprises radioactive labels having different half-lives.

Worldwide, nuclear 'stress tests' are the imaging modality used most commonly for detecting obstructions of blood flow to the heart due to coronary artery disease. For nuclear stress tests, single-photon imaging (SPECT) tracers are used most commonly, whereas PET tracers are used less often. As discussed above, PET imaging technology is inherently superior to SPECT imaging technology because PET demonstrates an intrinsically-superior spatial resolution and sensitivity for detecting tracer in vivo, compared to SPECT imaging systems. Yet SPECT cardiac imaging is often used because SPECT cardiac tracers can be injected while the patient performs physical exercise (e.g., on a treadmill) for placing 'stress' on the heart, whereas currently-available PET tracers can only be injected when the patient is immobile, on a PET scanner, while his/her heart is being 'stressed' by a pharmacologic agent that is infused intravenously. Physical exercise is the preferred method for stressing the heart (rather than pharmacological stress), because the information obtained about cardiopulmonary performance (e.g., as indicated by the duration of exercise time a patient can perform in a standardized treadmill protocol) and changes in electrocardiography (EKG) during physical exercise has well-validated prognostic significance. During pharmacologic stress, with the patient immobile, no cardiopulmonary performance information is obtained and EKG findings have been found to be less prognostically-valuable than an exercise EKG. Because of the rapid absorption of compounds of any of formula I to IX by the heart, their sustained retention by the heart, their long physical (radioactive half-life), and their rapid clearance from the bloodstream, PET imaging with compounds of any of formula I to IX has the characteristics for being a fit-for-purpose PET tracer of blood flow to the heart, with potential use during treadmill exercise. For example, a compound of any of formula I to IX can be injected as the patient exercises, with the ability to delay PET imaging until exercise is complete and after any desirable delay (e.g., cardiac imaging is feasible hours and days after tracer-injection).

In some embodiments, a provided method further comprises the step of performing a cardiac stress test on the subject, using standard methods known in the art. In some embodiments, the cardiac stress test is a nuclear stress test on the subject. In some embodiments, the cardiac stress test comprises physical exercise, such as on a treadmill. In some embodiments, the stress test comprises administering medication to stress the subject's heart (e.g., inotropic or vasodilator pharmacologic cardiac stress agents). In some embodiments, the stress test is performed prior to the administration of the labeled compound. In some embodiments, the stress test is performed concurrent with the administration of the labeled compound. In some embodiments, the stress test is performed subsequent to the administration of the labeled compound. In some embodiments, the stress test comprises collecting cardiopulmonary performance and ECG data. In some embodiments, there is a delay period between the stress test and the imaging. In some embodiments, the delay period is about 5 minutes. In some embodiments, the delay period is about 10 minutes. In some embodiments, the delay period is about 20 minutes. In some embodiments, the delay period is about 30 minutes. In some embodiments, the delay period is about 40 minutes. In some embodiments, the delay period is about 50 minutes. In some embodiments, the delay period is about 60 minutes. In some embodiments, the delay period is about 90 minutes. In some embodiments, the delay period is about 120 minutes. In some embodiments, the delay period is greater than about 120 minutes.

In some embodiments, the labeled compound is administered during the stress test. In some embodiments, the labeled compound is administered during the physical exercise. In some embodiments, the labeled compound is administered prior to the stress test. In some embodiments, the labeled compound is administered prior to the physical exercise. In some embodiments, the labeled compound is administered after the stress test. In some embodiments, the labeled compound is administered after the physical exercise.

In some embodiments, a provided method comprises a two-part nuclear stress test, wherein the first part includes scanning the heart while it is at rest, and the second part includes scanning the heart after or during stress, and then comparing the two images to detect a stress-induced change in blood flow to the heart (a sign of coronary artery disease) and/or a change in the function of the heart—i.e., the wall motions and contractions of the heart (which can be a sign of coronary artery disease, cancer chemotherapy toxicity, or other conditions). In some embodiments, the imaging technique used in each part is the same. In other embodiments, the imaging technique used in each part is different (e.g., SPECT followed by PET).

It will be appreciated that the comparison of images taken at different time points, including but not limited to before and after a stress test, are useful in the diagnosis or treatment of various cardiovascular conditions, diseases, or disorders. In some embodiments, an image before a stress test is used as a reference image, to which another image is compared. In some embodiments, a first image is collected before the stress test, and a second image is collect during or after the stress test. In some embodiments, a first image is used as a reference image. In some embodiments, a provided method comprises a step of comparing a second image to a first image. In some embodiments, a provided method comprises a step of comparing a second image to a first image, comprising normalizing the signal intensity of each region of the second image to the first image. In some embodiments, a provided method comprises a step of comparing a second image to a first image, comprising normalizing the signal intensity of each region of the second image relative to the first image, wherein weaker normalized signal intensity indicates less blood blow during or after stress. In some embodiments, weaker normalized signal indicates constrained blood flow. In some embodiments, weaker normalized signal indicates a constrained blood vessel in the cardiac tissue. In some embodiments, weaker normalized signal indicates stress ischemia. In some embodiments, weaker normalized signal indicates a wound in the cardiac tissue. In some embodiments, weaker normalized signal indicates a scar in the cardiac tissue. In some embodiments, a stronger-than-average normalized signal indicates diseased cardiac tissue. In some embodiments, an increased SUV indicates diseased cardiac tissue. Diseased cardiac tissue can be due to any cause, including but not limited to myocardial ischemia due to coronary artery disease.

In some embodiments, for myocardial dysfunction or low cardiac output, a cardiac ejection fraction of <50% is typically abnormal. Abnormal wall motions/contractions are detected visually/qualitatively through analyzing an image obtained in step of a provided method.

In some embodiments, the present invention provides a method for the diagnosis of cardiovascular diseases, disorders, or conditions, comprising administering a labeled compound of any of formula I to IX to a subject in need thereof. In some embodiments, the cardiovascular disease is atherosclerosis, cardiomyopathy, ischemic attack, or impaired cardiac blood flow. In some embodiments, the disease, disorder, or condition affects: myocardial blood flow, myocardial viability, myocardial function, ejection of blood from heart or from one of its anatomic chambers, cardiovascular expression of Hsp90, or combinations thereof. In certain embodiments, the cardiovascular disease, disorder, or condition is selected from the group consisting of coronary artery disease (including but not limited to atherosclerosis), prior myocardial infarction, cardiomyopathy, and poor cardiac output. In some embodiments, the cardiovascular disease, disorder, or condition is associated with abnormal Hsp90 expression or protein levels. In some embodiments, the cardiovascular disease, disorder, or condition is abnormal Hsp90 expression or protein levels. In some embodiments, an abnormal cardiac Hsp90 expression or protein level is higher than the normal healthy cardiac level. In some embodiments, an abnormal cardiac Hsp90 expression or protein level is lower than the normal healthy cardiac level. In some embodiments, an abnormal cardiac Hsp90 expression or protein level comprises Hsp90 isoforms in ratios different than a normal healthy cardiac condition.

In some embodiments, the present invention provides a method for the treatment or prevention of cardiovascular diseases, conditions, or disorders comprising administering a compound of any of formula I to IX to a subject in need thereof. In some embodiments, the cardiovascular disease is selected from the group consisting of atherosclerosis, cardiomyopathy, ischemic attack, or impaired cardiac blood flow. In some embodiments, the disease, disorder, or condition affects: myocardial blood flow, myocardial viability, myocardial function, ejection of blood from heart or from one of its anatomic chambers, cardiovascular expression of Hsp90, or combinations thereof. In certain embodiments, the cardiovascular disease, disorder, or condition is selected from the group consisting of coronary artery disease (including but not limited to atherosclerosis), prior myocardial infarction, cardiomyopathy, and poor cardiac output.

Cancer treatment can sometimes cause undesirable or even severe cardiac side effects. For example, anti-cancer drugs such as doxorubicin may cause cardiomyopathy (Lu, Monitoring Cardiac Function in Patients Receiving Doxorubicin, Semin. Nucl. Med. 2005, 35(3):197-201). In some embodiments, the present invention provides a method for monitoring the effect of cancer treatment on the heart comprising:

(a) administering a labeled compound of any of formula I to IX to a subject who is scheduled for cancer treatment, currently undergoing cancer treatment, or has completed or discontinued cancer treatment; and (b) imaging the cardiac tissue of the subject to detect the labeled compound; and (c) recommending to the subject an appropriate avoidance, continuation, modification, or termination in cancer treatment.

In some embodiments, the present invention provides a method for monitoring a cancer treatment regimen, comprising steps of:

(a) administering a labeled compound of any of formula I to IX to a subject under a cancer treatment regimen;

(b) imaging the cardiac tissue of the subject by detecting the labeled compound in the subject;

(c) analyzing the images from step (b); and (d) maintaining, modifying or discontinuing the cancer treatment regimen.

In some embodiments, a provided method detects cardiotoxicity. In some embodiments, a provided method detects myocardial dysfunction and problems with myocardial blood flow. Based on the presence or absence of cardiotoxicity, myocardial dysfunction and/or myocardial blood flow, a cancer treatment is avoided, continued, modified or terminated.

Patient stratification is important for clinical trials, medical prevention, and treatment. In some embodiments, the present invention provides methods for patient stratification based on cardiac imaging. In some embodiments, the present invention provides a method for selecting subjects for a test or treatment, comprising steps of:

(a) administering a labeled compound of any of formula I to IX to a subject;

(b) imaging the cardiac tissue of the subject by detecting the labeled compound in the subject;

(c) analyzing the images from step (b); and (d) including or excluding the subject for a test or a treatment.

In some embodiments, a test or treatment comprises the use of a compound that binds to Hsp90. In some embodiments, a test or treatment comprises the use of an Hsp90 inhibitor. In some embodiments, the method for selecting a subject is for a clinical trial. In some embodiments, the method for selecting a subject is for a clinical trial of a new therapy or diagnosis. In some embodiments, the method for selecting a subject is for a clinical trial of a new therapy or diagnosis for a cardiovascular disease, condition or disorder. In some embodiments, the method for selecting a subject is for a clinical trial of a new therapy or diagnosis for a non-cardiovascular disease, condition or disorder. In some embodiments, the test is coronary angiography. In some embodiments, the test is to confirm myocardial ischemia if detected by imaging as in step c. In some embodiments, the method for selecting is for a clinical trial of a new therapy or diagnosis for cancer. In some embodiments, the test is a cardiovascular test. In some embodiments, the treatment is a cardiovascular treatment. In some embodiments, the test is a cancer test. In some embodiments, the treatment is a cancer treatment. As understood by a person of ordinary skill in the art, medical treatment and/or diagnosis often has undesirable side effects on cardiac tissues. The provided methods enable one of skill in the art to analyze the cardiovascular condition of a subject and determine whether the subject should be included or excluded from said test or treatment. In some embodiments, a subject is excluded from a treatment comprising a potentially cardiotoxic drug. In some embodiments, a subject is included in a treatment comprising a potentially cardiotoxic drug.

In some embodiments, the present invention provides a method for detecting cardiotoxicity of a non-labeled compound. In some embodiments, the present invention provides a method for detecting cardiotoxicity of a non-labeled compound through cardiac imaging of its labeled counterpart. In some embodiments, the present invention provides a method for detecting cardiotoxicity of a labeled compound. In some embodiments, uptake, whether focal or diffuse or both, with a concentration greater than that observed in patient population is considered abnormal. In some embodiments, a standardized uptake value ("SUV") greater than about 0.5, 1, 1.5, 2, 2.5, 3, 3.5, 4, 4.5, 5, 5.5, 6, 7, 8, 9 or 10 indicates cardiotoxicity. In some embodiments, an SUV greater than about 0.5 indicates cardiotoxicity. In some embodiments, an SUV greater than about 1 indicates cardiotoxicity. In some embodiments, an SUV greater than about 1.5 indicates cardiotoxicity. In some embodiments, an SUV greater than about 2 indicates cardiotoxicity. In some embodiments, an SUV greater than about 2.5 indicates cardiotoxicity. In some embodiments, an SUV greater than about 3 indicates cardiotoxicity. In some embodiments, an SUV greater than about 3.5 indicates cardiotoxicity. In some embodiments, an SUV greater than about 4 indicates cardiotoxicity. In some embodiments, an SUV greater than about 4.5 indicates cardiotoxicity. In some embodiments, an SUV greater than about 5 indicates cardiotoxicity. In some embodiments, an SUV greater than about 4.5 indicates cardiotoxicity. In some embodiments, an SUV greater than about 5.5 indicates cardiotoxicity. In some embodiments, an SUV greater than about 6 indicates cardiotoxicity. In some embodiments, an SUV greater than about 7 indicates cardiotoxicity. In some embodiments, an SUV greater than about 8 indicates cardiotoxicity. In some embodiments, an SUV greater than about 9 indicates cardiotoxicity. In some embodiments, an SUV greater than about 10 indicates cardiotoxicity.

In some embodiments, a provided method provides an approach to patient screening, distinguishing patients likely to have either a favorable or unfavorable therapeutic response to a compound that binds to Hsp90 for cardiovascular treatment. In some embodiments, a provided method provides an approach to patient screening, distinguishing patients likely to have either a favorable or unfavorable therapeutic response to a compound for cardiovascular treatment, wherein the compound is an unlabeled counterpart of a compound of any of formula I to IX.

In some embodiments, the present invention provides a method for selecting subjects for a test or treatment, comprising steps of:
 (a) administering to a subject a labeled compound that binds to stress-specific Hsp90 to a subject;
 (b) imaging the cardiac tissue of the subject by detecting the labeled compound in the subject;
wherein increased uptake of the labeled compound indicates more likelihood for the subject to benefit from a test or treatment comprising the use of a compound that binds to Hsp90.

In some embodiments, a test or treatment comprises the use of a compound that binds to Hsp90. In some embodiments, a test or treatment comprises the use of a compound that binds to stress-specific Hsp90. In some embodiments, a test or treatment comprises the use of the non-labeled counterpart of the labeled compound in step (b).

Dosing is one of the key aspects of a treatment regimen. In some embodiments, the present invention provides a method for optimizing the dosage of a drug based on cardiac imaging, so that the desired therapeutic effects can be achieved with minimal side effects. In some embodiments, the present invention provides a method for determining the dosage of a drug, comprising steps of:
 (a) administering a labeled compound of any of formula I to IX to a subject;
 (b) imaging the cardiac tissue of the subject by detecting the labeled compound in the subject;
 (c) analyzing the images from step (b); and
 (d) administering to the subject a suitable amount of a drug.

In some embodiments, a provided method comprises determining the effective dosage of a drug. In some embodiments, a provided method comprises determining the toxicity of a drug in the subject. In some embodiments, a provided method comprising determining the minimum effective dosage of a drug. In some embodiments, a provided method comprises determining the highest toxicity dosage for a subject. In some embodiments, a provided method comprises determining the highest tolerable dosage for a subject. In some embodiments, a provided method comprises determining the balance between efficacy and toxicity and/or safety.

In some embodiments, the drug is a cardiovascular drug. In some embodiments, the drug is a non-radioactive amount of a compound that binds to Hsp90. Exemplary cardiovascular drugs are well known and prescribed in the art, including but not limited to 1) anti-anginals, 2) anti-arrhythmics, 3) anti-hypertensives, 4) anti-coagulants, 5) anti-hyperlipidemic agents, 6) hypo-glycemic agents, and 7) anti-thyroid drugs and thyroid hormones. Among many others, these can be organic nitrates, including but not limited to amyl nitrite and nitroglycerine; calcium channel antagonists, including but not limited to dihydropyridines, benzothiazepines, and aralkylamines; β-Adrenergic Antagonists, for example but not limited to propranolol; and angiotensin-converting enzyme (ACE) inhibitors. Examples include but are not limited to: amyl nitrite, glyceryl trinitrate, isosorbide dinitrate, erythritol tetranitrate, pentaerythritol tetranitrate, Nifedipine, Amlodipine, Nicardipine, diltiazem, Verapamil, Bepridil, Propranolol, Quinidine, Procainamide, Disopyramide, Lidocaine, Phenytoin, Mexiletine, Tocainide, Encainide, Flecainide, Lorcainide, Morcizine, Propafenone, Sotalol, Amiodarone, Bretylium tosylate, Captopril, Lisinopril, Enalapril, Benzapril, Quinapril, Ramipril, Fosinopril, Hydralazine, sodium nitroprusside, Diazoxide, Minoxidil, Coumarin and its derivatives, warfarin, bishydroxycoumarin, 1,3-Indandione and its derivatives, anisidione and heparin.

In some embodiments, the drug is a cancer drug. In some embodiments, the drug is for cancer chemotherapy. In some embodiments, the drug is for cancer radiotherapy. Exemplary chemotherapy drugs are widely known in the art, including but not limited to tubulin-binding drugs, kinase inhibitors, alkylating agents, DNA topoisomerase inhibitors, anti-folates, pyrimidine analogs, purine analogs, DNA antimetabolites, hormonal therapies, retinoids/deltoids, photodynamic therapies, cytokines, angiogenesis inhibitors, and antimitotic agents. Examples are extensively described in the art, including but not limited to those in PCT Application Publication No. WO2010/025272, the entirety of which is hereby incorporated by reference. In some embodiments, a "tubulin-binding drug" refers to a ligand of tubulin or to a compound capable of binding α or β-tubulin monomers or oligomers thereof, αβ-tubulin heterodimers or oligomers thereof, or polymerized microtubules. Exemplary tubulin-binding drugs include, but not limited to:

a) Combretastatins or other stilbene analogs (Pettit et al, Can. J. Chem., 1982; Pettit et al, J. Org. Chem., 1985; Pettit et al, J. Nat. Prod., 1987; Lin et al, Biochemistry, 1989; Singh et al, J. Org. Chem., 1989; Cushman et al, J. Med. Chem., 1991; Getahun et al, J. Med. Chem., 1992; Andres et al, Bioorg. Med. Chem. Lett., 1993; Mannila, Liebigs. Ann. Chem., 1993; Shirai et al, Bioorg. Med. Chem. Lett., 1994; Medarde et al., Bioorg. Med. Chem. Lett., 1995; Pettit et al, J. Med. Chem., 1995; Wood et al, Br. J. Cancer., 1995; Bedford et al, Bioorg. Med. Chem. Lett., 1996; Dorr et al, Invest. New Drugs, 1996; Jonnalagadda et al., Bioorg. Med. Chem. Lett., 1996; Shirai et al, Heterocycles, 1997; Aleksandrzak K, Anticancer Drugs, 1998; Chen et al, Biochem. Pharmacal., 1998; Ducki et al, Bioorg. Med. Chem. Lett., 1998; Hatanaka et al, Bioorg. Med. Chem. Lett., 1998; Medarde, Eur. J. Med. Chem., 1998; Medina et al, Bioorg. Med. Chem. Lett., 1998; Ohsumi et al, Bioorg. Med. Chem. Lett., 1998; Ohsumi et al., J. Med. Chem., 1998; Pettit G R et al., J. Med. Chem., 1998; Shirai et al, Bioorg. Med. Chem. Lett., 1998; Banwell et al, Aust. J. Chem., 1999; Medarde et al, Bioorg. Med. Chem. Lett., 1999; Shan et al, PNAS, 1999; Combeau et al, Mol. Pharmacal, 2000; Pettit et al, J. Med Chem, 2000; Pettit et al, Anticancer Drug Design, 2000; Pinney et al, Bioorg. Med. Chem. Lett., 2000; Flynn et al., Bioorg. Med. Chem. Lett., 2001; Gwaltney et al, Bioorg. Med. Chem. Lett., 2001; Lawrence et al, 2001; Nguyen-Hai et al, Bioorg. Med. Chem. Lett., 2001; Xia et al, J. Med. Chem., 2001; Tahir et al., Cancer Res., 2001; Wu-Wong et al., Cancer Res., 2001; Janik et al, Bioorg. Med. Chem. Lett., 2002; Kim et al., Bioorg Med Chem Lett., 2002; Li et al, Bioorg. Med. Chem. Lett., 2002; Nam et al, Bioorg. Med. Chem. Lett., 2002; Wang et al, J. Med. Chem. 2002; Hsieh et al, Bioorg. Med. Chem. Lett., 2003; Hadimani et al., Bioorg. Med. Chem. Lett., 2003; Mu et al, J. Med. Chem., 2003; Nam, Curr. Med. Chem., 2003; Pettit et al, J. Med. Chem., 2003; WO 02/50007, WO 02/22626, WO 02/14329, WO 01/81355, WO 01/12579, WO 01/09103, WO 01/81288, WO 01/84929, WO 00/48591, WO 00/48590, WO 00/73264, WO 00/06556, WO 00/35865, WO 00/48590, WO 99/51246, WO 99/34788, WO 99/35150, WO 99/48495, WO 92/16486, U.S. Pat. Nos. 6,433,012, 6,201,001, 6,150,407, 6,169,104, 5,731,353, 5,674,906, 5,569,786, 5,561,122, 5,430,062, 5,409,953, 5,525,632, 4,996,237 and 4,940,726 and U.S. patent application Ser. No. 10/281,528. The entirety of each of the references is hereby incorporated by reference);

b) 2,3-substituted Benzo[b]thiophenes (Pinney et al, Bioorg. Med. Chem. Lett., 1999; Chen et al, J. Org. Chem., 2000; U.S. Pat. Nos. 5,886,025; 6,162,930, and 6,350,777; WO 98/39323. The entirety of each of the references is hereby incorporated by reference);

c) 2,3-disubstituted Benzo[b]furans (WO 98/39323, WO 02/060872. The entirety of each of the references is hereby incorporated by reference);

d) Disubstituted Indoles (Gastpar R, J. Med. Chem., 1998; Bacher et al, Cancer Res., 2001; Flynn et al, Bioorg. Med. Chem. Lett, 2001; WO 99/51224, WO 01/19794, WO 01/92224, WO 01/22954; WO 02/060872, WO 02/12228, WO 02/22576, and U.S. Pat. No. 6,232,327. The entirety of each of the references is hereby incorporated by reference);

e) 2-Aroylindoles (Mahboobi et al, J. Med. Chem., 2001; Gastpar et al., J. Med. Chem., 1998; WO 01/82909. The entirety of each of the references is hereby incorporated by reference);

f) 2,3-disubstituted Dihydronaphthalenes (WO 01/68654, WO 02/060872. The entirety of each of the references is hereby incorporated by reference);

g) Benzamidazoles (WO 00/41669, the entirety of which is hereby incorporated by reference);

h) Chalcones (Lawrence et al, Anti-Cancer Drug Des, 2000; WO 02/47604. The entirety of each of the references is hereby incorporated by reference);

i) Colchicine, Allocolchicine, Thiocolcichine, Halichondrin B, and Colchicine derivatives (WO 99/02166, WO 00/40529, WO 02/04434, WO 02/08213, U.S. Pat. Nos. 5,423,753. 6,423,753. The entirety of each of the references is hereby incorporated by reference) in particular the N-acetyl colchinol prodrug, ZD-6126;

j) Curacin A and its derivatives (Gerwick et al, J. Org. Chem., 1994, Blokhin et al, Mol. Phamacol., 1995; Verdier-Pinard, Arch. Biochem. Biophys., 1999; WO 02/06267. The entirety of each of the references is hereby incorporated by reference);

k) Dolastatins such as Dolastatin-10, Dolastatin-15, and their analogs (Pettit et al, J. Am. Chem. Soc., 1987; Bai et al, Mol. Pharmacal, 1995; Pettit et al, Anti-Cancer Drug Des., 1998; Poncet, Curr. Pharm. Design, 1999; WO 99/35164; WO 01/40268; U.S. Pat. No. 5,985,837. The entirety of each of the references is hereby incorporated by reference);

l) Epothilones such as Epothilones A, B, C, D, and Desoxyepothilones A and B, Fludelone (Chou et al. Cancer Res. 65:9445-9454, 2005, the entirety of which is hereby incorporated by reference), 9,10-dehydro-desoxyepothilone B (dehydelone), iso-oxazole-dehydelone (17-isooxazole-dehydelone), fludelone, iso-oxazolefludelone (17-isooxazole-fludelone), (Danishefsky, et al., PNAS, v. 105, 35:13157-62, 2008; WO 99/02514, U.S. Pat. No. 6,262, 094, Nicolau et al., Nature, 1997, Pub. No. US2005/0 143429. The entirety of each of the references is hereby incorporated by reference);

m) Inadones (Leoni et al., J. Natl. Cancer Inst., 2000; U.S. Pat. No. 6,162,810. The entirety of each of the references is hereby incorporated by reference);
n) Lavendustin A and its derivatives (Mu F et al, J. Med. Chem., 2003, the entirety of which is hereby incorporated by reference);
o) 2-Methoxyestradiol and its derivatives (Fotsis et al, Nature, 1994; Schumacher et al, Clin. Cancer Res., 1999; Cushman et al, J. Med. Chem., 1997; Verdier-Pinard et al, Mol. Pharmacal, 2000; Wang et al, J. Med. Chem., 2000; WO 95/04535, WO 01/30803, WO 00/26229, WO 02/42319 and U.S. Pat. Nos. 6,528,676, 6,271,220, 5,892,069, 5,661,143, and 5,504,074. The entirety of each of the references is hereby incorporated by reference);
p) Monotetrahydrofurans ("COBRAs"; Uckun, Bioorg. Med. Chem. Lett., 2000; U.S. Pat. No. 6,329,420. The entirety of each of the references is hereby incorporated by reference);
q) Phenylhistin and its derivatives (Kanoh et al, J. Antibiot., 1999; Kano et al, Bioorg. Med. Chem., 1999; U.S. Pat. No. 6,358,957. The entirety of each of the references is hereby incorporated by reference);
r) Podophyllotoxins such as Epidophyllotoxin (Hammonds et al, J. Med. Microbial, 1996; Coretese et al, J. Biol. Chem., 1977. The entirety of each of the references is hereby incorporated by reference);
s) Rhizoxins (Nakada et al, Tetrahedron Lett., 1993; Boger et al, J. Org. Chem., 1992; Rao, et al, Tetrahedron Lett., 1992; Kobayashi et al, Pure Appl. Chem., 1992; Kobayashi et al, Indian J. Chem., 1993; Rao et al, Tetrahedron Lett., 1993. The entirety of each of the references is hereby incorporated by reference);
t) 2-strylquinazolin-4(3H)-ones ("SQOs", Jiang et al, J. Med. Chem., 1990, the entirety of which is hereby incorporated by reference);
u) Spongistatin and Synthetic spiroketal pyrans ("SPIKETs"; Pettit et al, J. Org. Chem., 1993; Uckun et al, Bioorgn. Med. Chem. Lett., 2000; U.S. Pat. No. 6,335,364, WO00/00514. The entirety of each of the references is hereby incorporated by reference);
v) Taxanes such as Paclitaxel (TAXOL®), Docetaxel (TAXOTERE®), and Paclitaxel derivatives (U.S. Pat. No. 5,646,176, WIPO Publication No. WO 94/14787, Kingston, J. Nat. Prod., 1990; Schiff et al, Nature, 1979; Swindell et al, J. Cell Biol., 1981. The entirety of each of the references is hereby incorporated by reference);
x) Vinca Alkaloids such as Vinblastine, Vincristine, Vindesine, Vinflunine, Vinorelbine (NAVELBINE®) (Owellen et al, Cancer Res., 1976; Lavielle et al, J. Med. Chem., 1991; Holwell et al, Br. J. Cancer., 2001. The entirety of each of the references is hereby incorporated by reference); and
y) Welwistatin (Zhang et al, Molecular Pharmacology, 1996, the entirety of which is hereby incorporated by reference).

Exemplary specific examples of tubulin-binding drugs include, but are not limited to, allocolchicine, amphethinile, chelidonine, colchicide, colchicine, combrestatin AI, combretastin A4, combretastain A4 phosphate, combrestatin 3, combrestatin 4, cryptophycin, curacin A, deo-dolastatin 10, desoxyepothilone A, desoxyepothilone B, dihydroxypentamethoxyflananone, docetaxel, dolastatin 10, dolastatin 15, epidophyllotoxin, epothilone A, epothilone B, epothilone C, epothilone D, etoposide, 9,10-dehydro-desoxyepothilone B (dehydelone), iso-oxazole-dehyedelone (17-isooxazole-dehydelone), fludelone, iso-oxazolefludelone (17-isooxazole-fludelone), griseofulvin, halichondrin B, isocolchicine, lavendustin A, methyl-3,5-diiodo-4-(4'-methoxyphenoxy) benzoate, N-acetylcolchinol, N-acetylcolchinol-0-phosphate, N-[2-[(4-hydroxyphenyl)amino]-3-pyridyl]-4-methoxybenzenesulfonamide, nocodazole, paclitaxel, phenstatin, phenylhistin, piceid, podophyllotoxin, resveratrol, rhizoxin, sanguinarine, spongistatin 1, steganacin, TAXOL, teniposide, thiocolchicine, vincristine, vinblastine, welwistatin, (Z)-2-methoxy-5-[2-(3,4,5-trimethoxyphenyl) vinyl]phenylamine, (Z)-3,5,4'-trimethoxystilbene (R3), 2-aryl-1,8-naphthyridin-4(1 H)-one, 2-(41-methoxyphenyl)-3-(3 1, 4 1, 5 1-rimethoxybenzoyl)-6-methoxybenzo[b]thiophene, 2-methoxy estradiol, 2-strylquinazolin-4(3H)-one, 5,6-dihydroindolo(2,1-a)isoquinoline, and 10-deacetylbaccatin III.

In some embodiments, a drug is a compound having the structure of formulae X wherein each variable is independently as described in classes and subclasses herein, both singly and in combination.

In some embodiments, the present disclosure provides methods of determining an effective dose and frequency of administration for therapy with a compound binding to Hsp90, which comprises administering to the patient a radiolabeled form of the compound binding to Hsp90, which optionally binds preferentially to a cardiac tissue-specific form of Hsp90 present in cardiac tissues, measuring uptake of the radiolabeled form of the compound binding to Hsp90 in cardiac tissues at one or more time points, and calculating the dose and frequency of administration needed to maintain in the cardiac tissue at each time point a concentration of the Hsp90 inhibitor effective to treat the cardiac tissue. The uptake of the radiolabeled form of the compound binding to Hsp90 can be determined using a PET assay, as discussed above. In some embodiments, the compound binding to Hsp90 has the structure of formula IX, or any of formula I to IX, wherein the radioactive iodide isotope is replaced with -I.

In one embodiment of the disclosure, the standardized uptake value ("SUV") of the radiolabeled compound derived from PET can be converted to molar concentrations of the compound in the cardiac tissue according to the following equation:

$$C_t = D \times ([A_c]_t / 100\%) \times (1/W) \times (1/MW)$$

In the above equation, $C_t$ is the molar concentration of the compound in the cardiac tissue at a time t following injection of the radiolabeled compound. D is the injected therapeutic dose. The term W is the cardiac tissue water space. The term MW is the molecular weight of the injected compound. The term $[A_c]_t$ is the %-injected radiolabeled dose in the cardiac tissue at time t, a value obtained from the SUV obtained from the PET image. Specifically, the term $[A_c]_t$ can be derived from the SUV in the cardiac tissue ($SUV_c$) by the following equation:

$$[A_c]_t / 100\% = SUV_c / [body\ weight(g)]$$

In the above equation, [body weight] refers to the body weight of the patient.

In one aspect, the present disclosure provides a method for determining the concentration of an Hsp90 inhibitor present in the cardiac tissue in a subject. A solution of the radiolabeled compound (also referred to herein as "hot" compound) can be injected into a subject without concomitant injection of the compound (i.e., non-radiolabeled form of the compound, also referred to herein as "cold" compound). In such cases, the concentration of the drug $C_t$ can be determined using the equation above. In one embodiment, the radiolabeled compound is the labeled form of the injected compound. For instance, the radiolabeled compound can be [$^{124}$I]-PUH71 and the administered compound can be PU-H71. In another embodiment, the radiolabeled compound can be different than the injected drug. The determination of the concentration of the drug in the cardiac tissue can be determined at a single time point or a plurality of time points following injection of the radiolabeled compound and the therapeutic compound. By comparing the concentration of the compound in the $C_t$ with known efficacious doses obtained from preclinical studies (e.g., half-inhibitory concentrations ($IC_{50}$)), one can determine if the administered dose will be efficacious. A physician can then adjust the therapeutic dose, D, accordingly to ensure that the known desired amount of the drug is in the cardiac tissue, $C_t$, is achieved; determining the unknown value, D, by rearranging the above formula as follows:

$$D=C_t \div [([A_c]/100\%) \times (1/W) \times (1/MW)]$$

In the embodiment where the radiolabeled compound is the radiolabeled form of the compound to be administered to the patient, the concentration of the compound in the cardiac tissue can be determined without actually administering the cold compound. In such cases, following determination of $[A]_t$ from the PET assay, different hypothetical injected dose values can be imputed into the equation above to determine the concentration of the compound in the cardiac tissue $C_t$. An effective dose can thereby be determined by comparing the concentration of the compound in the cardiac tissue with known efficacious doses obtained from preclinical studies, as discussed above.

The present disclosure also provides methods of determining the dose of a compound that is needed to saturate the Hsp90 in the cardiac tissue. As described above, the PET assay can be conducted by co-injecting a radiolabeled compound and a specific amount of non-radiolabelled compound. If the dose of the injected compound is sufficiently high to occupy most or all of the Hsp90 in the cardiac tissue, then the uptake of the radiolabeled inhibitor is suppressed. The point at which uptake of the radiolabeled inhibitor is suppressed can be used to determine the target-saturating dose of the non-radiolabeled compound, which would also be the 'maximum cardiac tissue dose' that a single dose of the non-radiolabelled compound can deliver or the maximally effective single dose of the non-radiolabeled compound. The number of cardiac tissue sites occupied by compound binding to Hsp90 can be calculated and converted to a percent occupancy. If the Hsp90-binding compound is delivered in an amount that approaches full occupancy of the Hsp90 sites, additional non-radiolabelled compound would not be expected to provide increased levels of efficacy. Hence, the methodology provides a means of determining a dose of the Hsp90-binding compound that can occupy most or all of the Hsp90 in the cardiac tissue. The methodology provides a more rational and effective dosing strategy that is based on PET-derived maximally effective cardiac tissue concentration rather than conventional maximum tolerated dose (MTD). The approach avoids dose escalation and limits the toxicological problems associated with the non-labeled compound. In some embodiments, the Hsp90 is cardiac-specific Hsp90.

In some embodiments, the present invention provides a method for determining the risk of a cardiovascular disease, comprising steps of:
  (a) administering a labeled compound of any one of formula I to IX to a subject;
  (b) imaging the cardiac tissue of the subject by detecting the labeled compound in the subject;
  (c) analyzing the images from step (b); and
  (d) recommending to the subject additional diagnostic testing, a suitable treatment or preventive regimen.

In some embodiments, the present invention provides a method for prediction of cardiovascular morbidity and mortality, comprising steps of:
  (a) administering a labeled compound of any one of formula I to IX to a subject;
  (b) imaging the cardiac tissue of the subject by detecting the labeled compound in the subject;
  (c) analyzing the images from step (b); and
  (d) recommending to the subject additional diagnostic testing, a suitable treatment, or preventive regimen.

In some embodiments, a provided method is used to determine the risk of heart attack, so appropriate prevention and/or medical intervention can be administered. In some embodiments, the present invention provides a method for determining the risk of heart attack, comprising steps of:
  (a) administering a labeled compound of any one of formula I to IX to a subject;
  (b) imaging the cardiac tissue of the subject by detecting the labeled compound in the subject;
  (c) analyzing the images from step (b); and
  (d) recommending to the subject additional diagnostic testing, a suitable treatment or preventive regimen.

It is well understood that analyzing the images produced in a disclosed method provides information, including but not limit to cardiac blood flow, to a person of ordinary skill in the art regarding the cardiovascular condition of a subject, and he or she can use such information to determine the risk of a subject and recommend suitable follow-ups, including but not limited to additional diagnostic testing, a suitable treatment or preventive regimen.

In some embodiments, the administration of a labeled compound and imaging of the cardiac tissue of the subject is performed before the subject is subjected to a cardiac stressor. In some embodiments, the labeled compound is administered to the subject during the subject being subjected to a cardiac stressor. As used herein, the term "cardiac stressor" refers to physical exercise or medication that stresses the heart.

In some embodiments, a labeled compound is a labeled compound of formula I, wherein the prior-labeling compound has the structure of formula I. In some embodiments, a labeled compound that binds to Hsp90 is a labeled compound of formula I. In some embodiments, the labeled compound that binds to Hsp90 has the structure of any one of formula III to IX. In some embodiments, the labeled compound that binds to Hsp90 is a labeled natural product or its derivative. In some embodiments, the labeled compound is labeled Geldanamycin or its derivative. In some embodiments, the labeled compound is labeled radicicol or its derivative. In some embodiments, the labeled compound is labeled Gamitrinib or its derivative. Exemplary prior-labeling compounds that bind to Hsp90 are widely known in the art, including but not limited to those described in Jhaveri and Modi, HSP90 inhibitors for cancer therapy and overcoming drug resistance, *Adv Pharmacol.* 2012; 65:471-517; and Taldone et al, Design, synthesis, and evaluation of small molecule Hsp90 probes, *Bioorg Med Chem.* 2011; 19(8):2603-14; U.S. Pat. Nos. 8,178,687 and 8,324,240; United States Patent Application Publication Nos. US2012/0277257, US2012/0264770, US2012/0237508, US2013/0045983, US2005/0107343, US2008/0234314, and US2012/0046266; and PCT patent application publication WO2008/115719, WO2008/118391, WO2004/097428, WO2006/098761, WO2006/123165, WO2007/134677, WO2008/093075, WO2007/104944, WO2009/097578, WO2008/118391, WO2007/134298 and WO2006/117669; the entirety of each of which is hereby incorporated by reference. All these compounds, among others, can be labeled using known chemistry in the art and be used in the provided methods described herewith.

In some embodiments, a labeled compound of formula I has the structure of formula II,

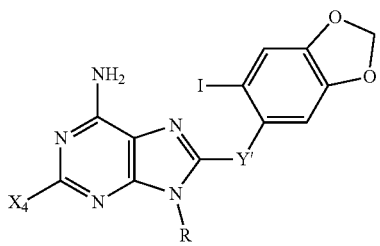

II wherein Y' is —CH$_2$— or S;

X$_4$ is hydrogen or halogen; and R is an amino alkyl moiety, optionally substituted on the amino nitrogen with one or two carbon-containing substituents selected independently from the group consisting of alkyl, alkenyl and alkynyl substituents, wherein the total number of carbons in the amino alkyl moiety is from 1 to 9.

In some embodiments, the labeled compound of formula I is an labeled analog of compound A (PUH71):

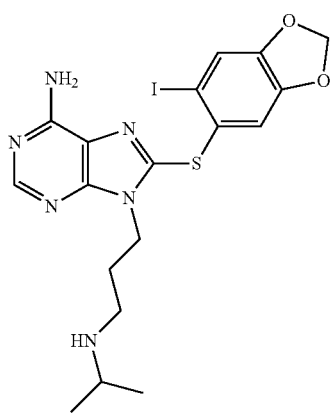

A wherein the labeled compound has at least one atom or substituent detectable by a medical imaging technique.

In some embodiments, a labeled compound A is labeled at 2'-iodo. In some embodiments, a labeled compound A has $^{123}$I at the 2'-iodo position. In some embodiments, a labeled compound A has $^{123}$I at the 2'-iodo position and is used for SPECT imaging. In some embodiments, a labeled compound A has $^{124}$I at the 2'-iodo position. In some embodiments, a labeled compound A has $^{124}$I at the 2'-iodo position and is used for PET imaging.

Compound A demonstrates rapid absorption and sustained retention in the human heart and rapid clearance from the bloodstream, which allows for its injection during physical exercise and a subsequent delay before cardiac imaging occurs. As a PET tracer, compound A offers the advantage of the intrinsically superior imaging quality of PET imaging over SPECT imaging—including a superior ability to detect smaller areas of blood flow obstruction and more accurate evaluation of cardiac pump function/cardiac output.

In some embodiments, the labeled compound of any of formula I to IX is labeled through substituting a hydrogen atom with a group that can be detected by a medical imaging technique. In some embodiments, a labeled compound of any of formula I to IX is labeled through substituting at least one hydrogen atom in the compound with at least one group that produces higher signal intensity than the at least one hydrogen atom. In some embodiments, the labeled compound of any of formula I to IX is radiolabeled. In some embodiments, the labeled compound comprises an isotope which decays by positron emission. In some embodiments, the labeled compound is labeled with one or more isotopes selected from $^{124}$I, $^{11}$C, $^{15}$O, $^{13}$N, and $^{18}$F. In some embodiments, the labeled compound is labeled with $^{124}$I. In some embodiments, a compound labeled with $^{124}$I is used in PET imaging. In some embodiments, a compound labeled with $^{123}$I is used in SPECT imaging. In some embodiments, the labeled compound comprises an isotope that decays by electron capture. In some embodiments, the labeled compound comprises an isotope selected from $^{123}$I and $^{131}$I. In some embodiments, the labeled compound comprises one or more labels suited for magnetic resonance imaging (MRI). In some embodiments, the labeled compound comprises one or more $^{19}$F. In some embodiments, a compound labeled with one or more $^{19}$F is used for MRI.

In some embodiments, a label is a fluorophore moiety. In some embodiments, a label is a nanometer-sized agent. In some embodiments, a label is a nanoparticle. In some embodiments, a label is a nanotube. In some embodiments, a label is liposome. In some embodiments, a nanotube or liposome comprises a moiety that produces an enhanced signal. In some embodiments, one or more MRI agents are linked or packaged in a nanotube, nanoparticle or liposome. In some embodiments, one nanometer-sized agent or nanoparticle or liposomal micelle is used to label more than one molecule a compound to be labeled; for example, more than one molecule of the compound to be labeled can be linked to a single nanoparticle. In some embodiments, a label is covalently linked to a compound. In some embodiments, a label is non-covalently linked to a compound.

In some embodiments, a labeled compound is selected from

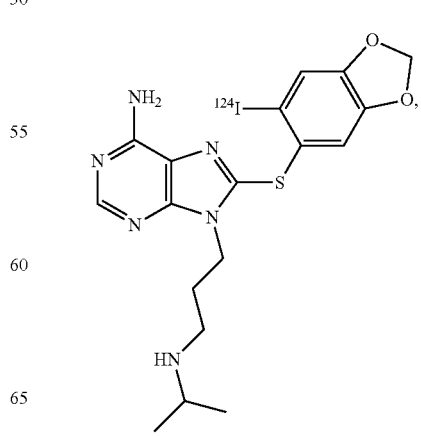

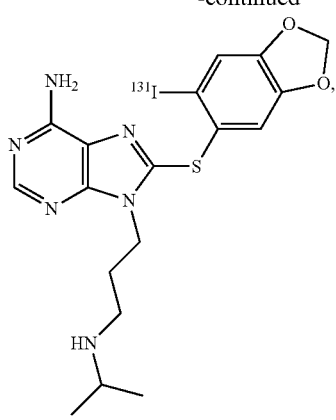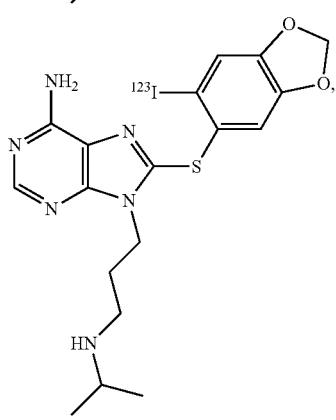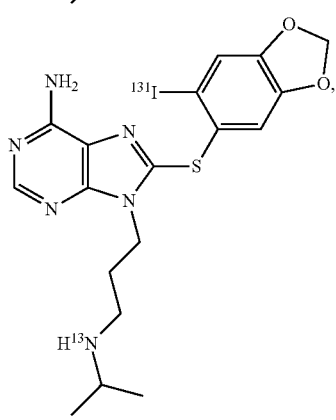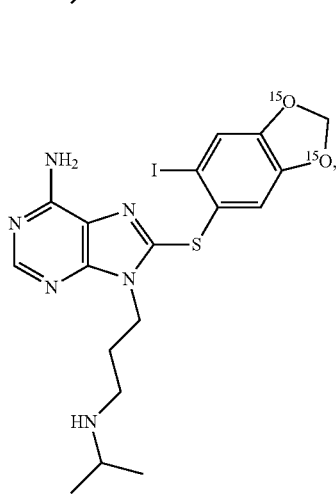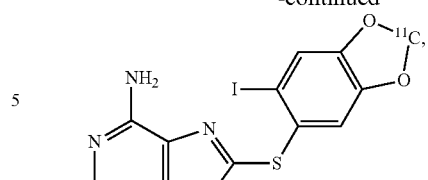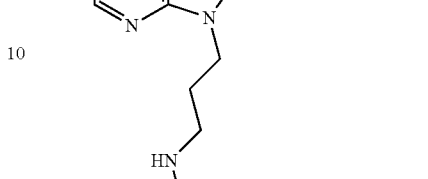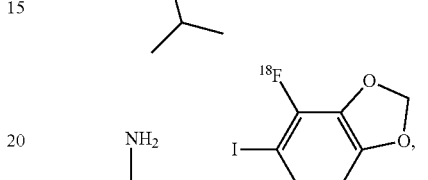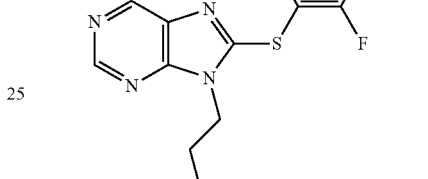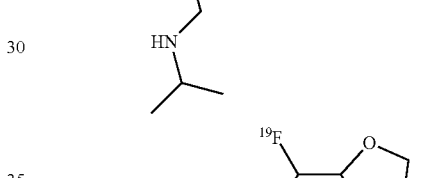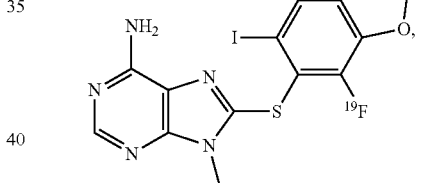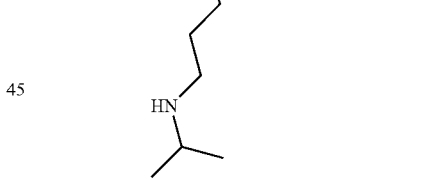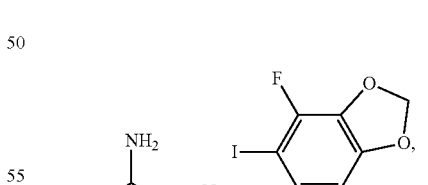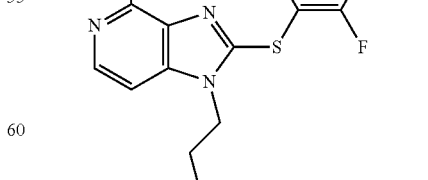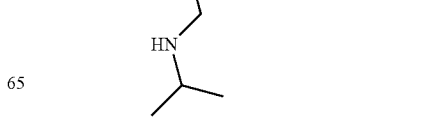

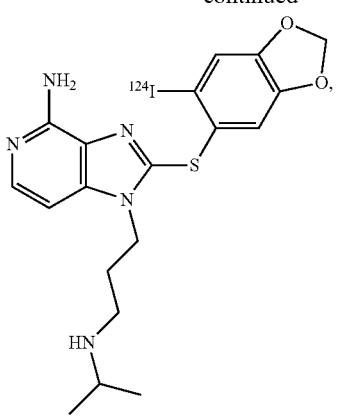

, and

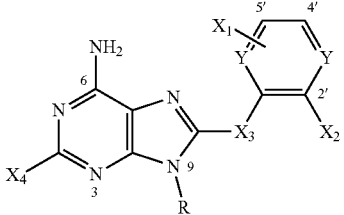

In some embodiments, the non-radioactive therapeutic compound used in a provided method binds to Hsp90. In some embodiments, the non-radioactive therapeutic compound is an Hsp90 inhibitor. In some embodiments, the non-radioactive compound is a natural product or its derivatives. In some embodiments, the non-radioactive compound is Geldanamycin or its derivative. In some embodiments, the non-radioactive compound is radicicol or its derivative. In some embodiments, the non-radioactive compound is Gamitrinib or its derivative. In some embodiments, the non-radioactive compound has the structure of formula X or its pharmaceutically acceptable salt thereof, wherein:
Y is CH, N or O;
R is hydrogen, a $C_1$ to $C_{10}$ alkyl, alkenyl, alkynyl, or an alkoxyalkyl group, optionally comprising one or more heteroatoms, or a targeting moiety connected to N9 via a linker;
$X_4$ is hydrogen or halogen;
$X_3$ is $CH_2$, $CF_2$, S, SO, $SO_2$, O, NH, or $NR^2$, wherein $R^2$ is alkyl;
$X_2$ is halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$alkyl, COO-alkyl, $NH_2$, OH, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl or O-alkyl; and
$X_1$ represents two substituents, which may be the same or different, disposed in the 4' and 5' positions on the aryl group, wherein $X_1$ is selected from halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$-alkyl, COO-alkyl, $NH_2OH$, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl, or O-alkyl, $C_1$ to $C_6$ alkyl or alkoxy, or wherein $X_1$ has the formula —O—$(CH_2)_n$—O—, wherein n is an integer from 0 to 2, and one of the oxygens is bonded at the 5'-position and the other at the 4'-position of the aryl ring.

In some embodiments, the non-radioactive therapeutic compound is compound A:

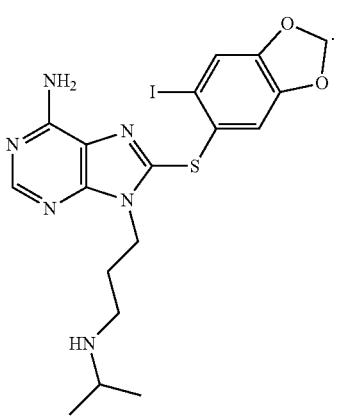 [SMILES: CC(C)NCCCn1c(Sc2cc3c(cc2I)OCO3)nc2c(N)ncnc21]

In some embodiments, a compound is labeled without changing the affinity, selectivity or biodistribution profile of the inhibitor are ideal probes for prognostic and/or diagnostic purposes. In one embodiment, a labeled compound is an iodine 124 radiolabeled versions of an HSP90 inhibitor or a compound having the structure of any of formula I to IX. In one embodiment, a labeled compound is an iodine 123 radiolabeled versions of an HSP90 inhibitor or a compound having the structure of any one of formula I to IX. In one embodiment, a labeled compound is an iodine 131 radiolabeled versions of an HSP90 inhibitor or a compound having the structure of any one of formula I to IX. In one embodiment, a labeled compound is an iodine 125 radiolabeled versions of an HSP90 inhibitor or a compound having the structure of any one of formula I to IX.

In another embodiment, a radiolabeled compound in a provided method is selected from a compound having the following formulae:

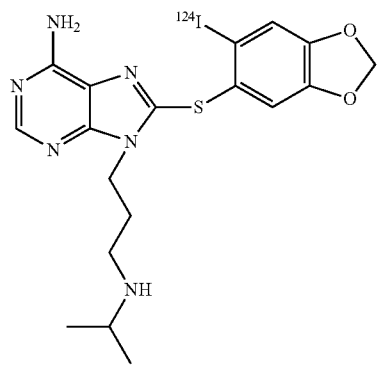

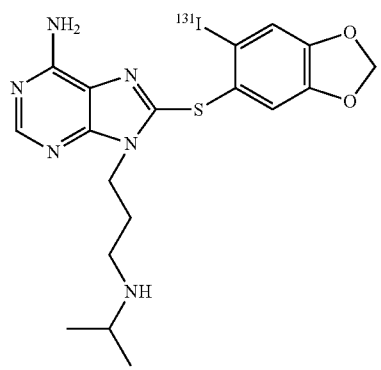

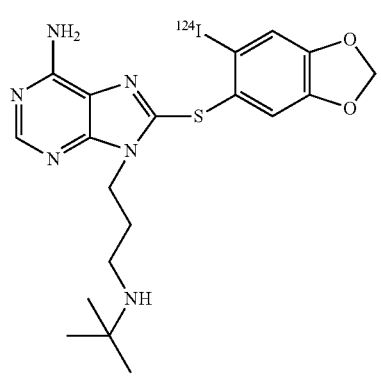

-continued

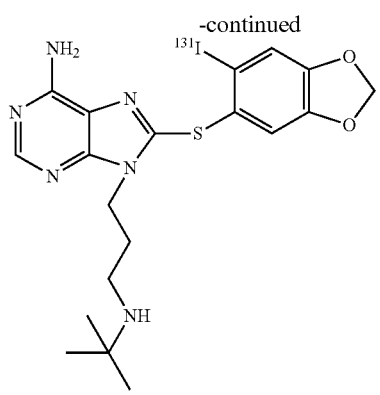

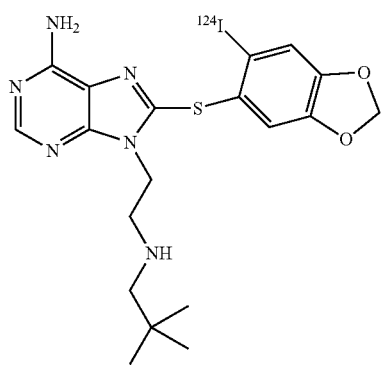

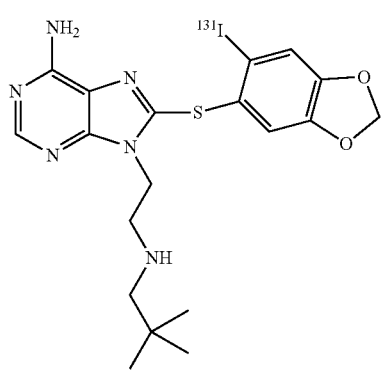

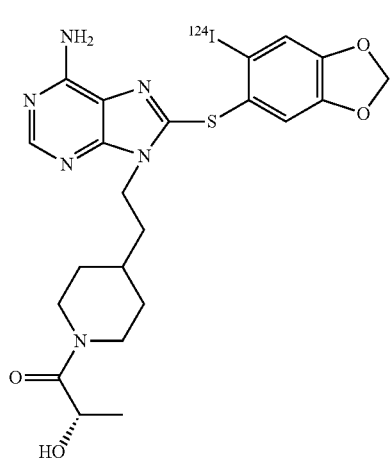

51
-continued
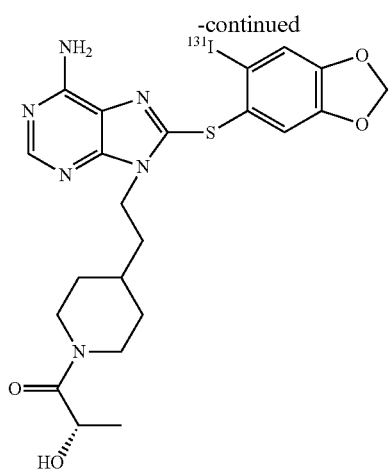
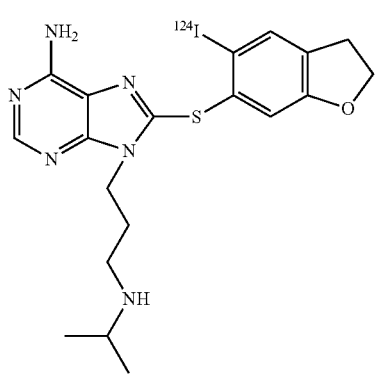
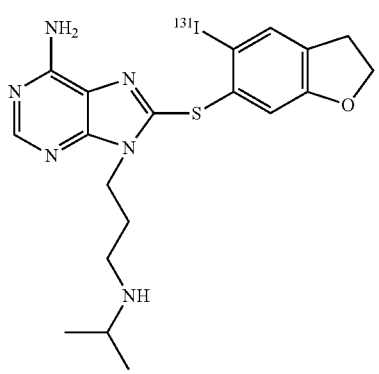
52
-continued
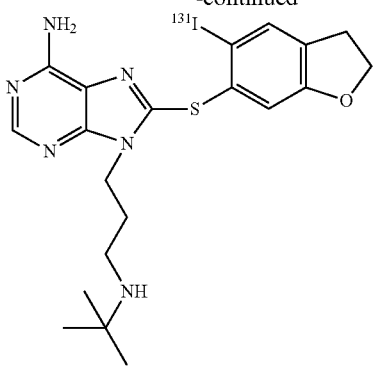
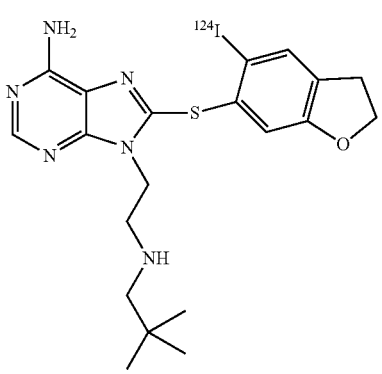
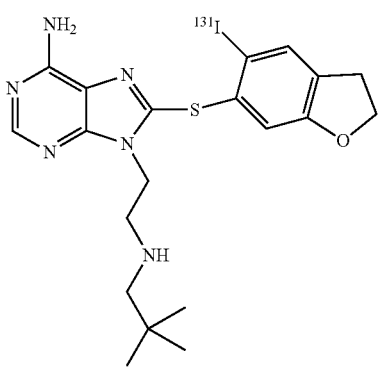
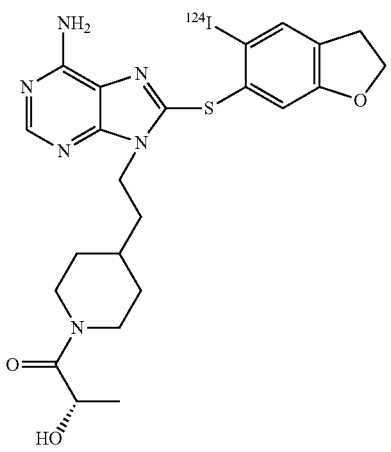

53
-continued
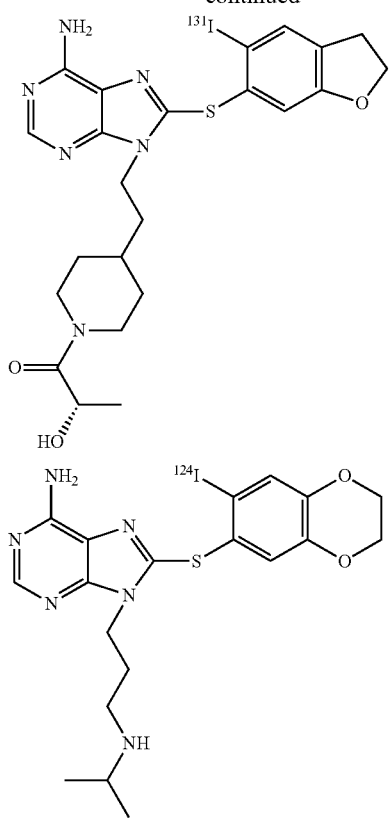
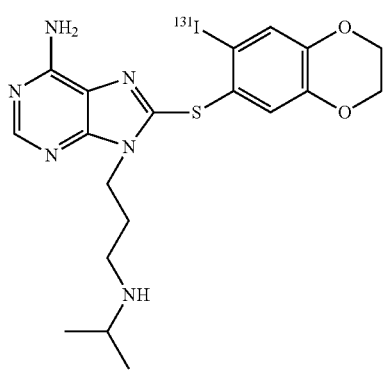
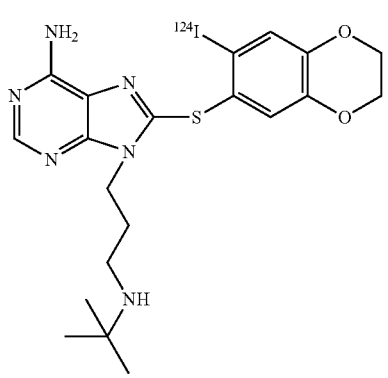
54
-continued
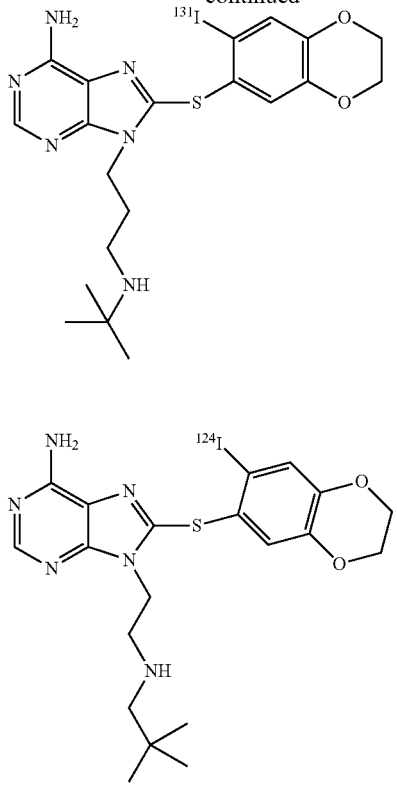
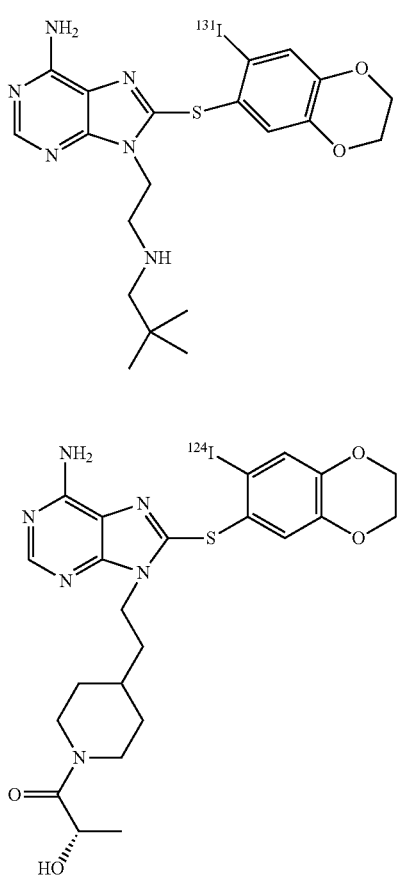

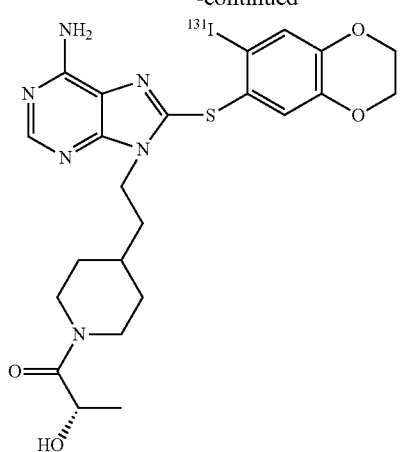
In another embodiment, a radiolabeled compound in a provided method is selected from a compound having the following formulae:
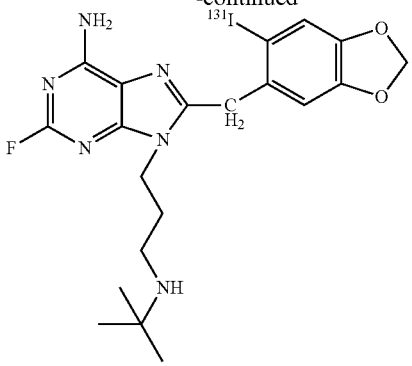
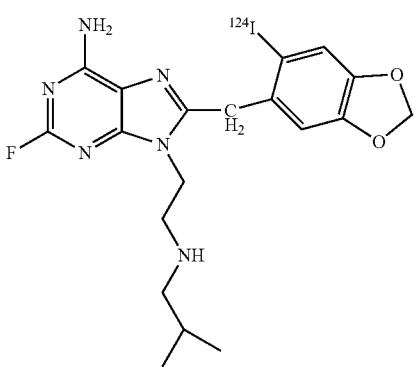
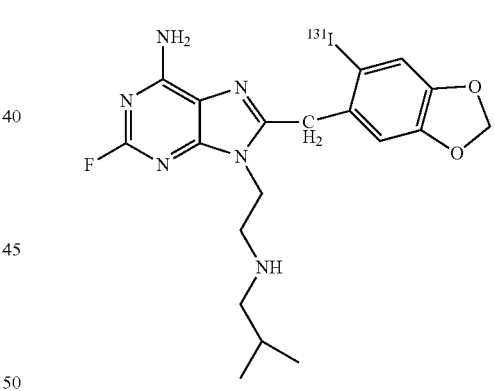
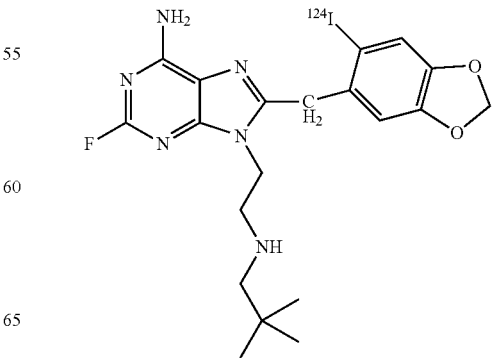

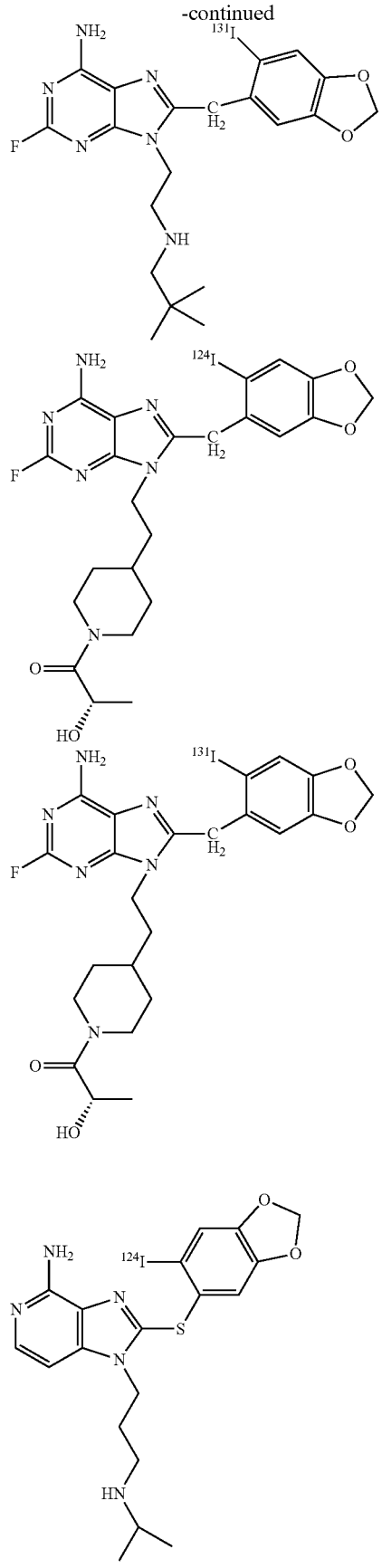
In still another embodiment, a radiolabeled compound in a provided method is selected from a compound having the following formulae:

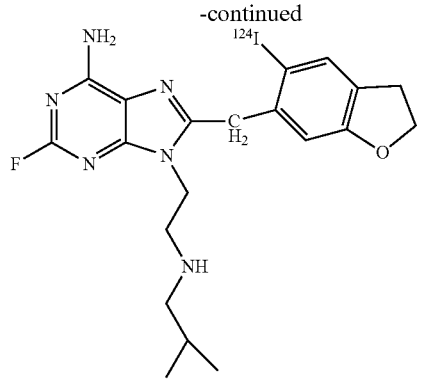
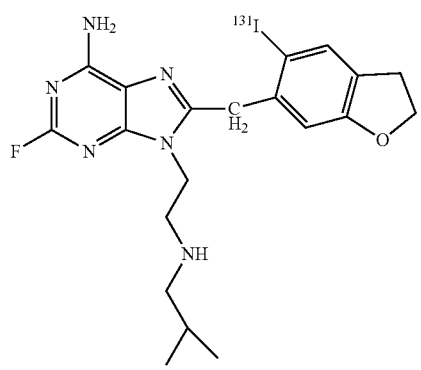
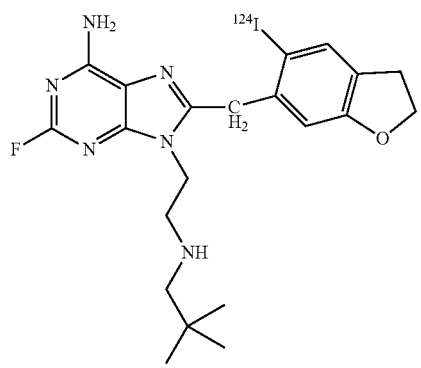
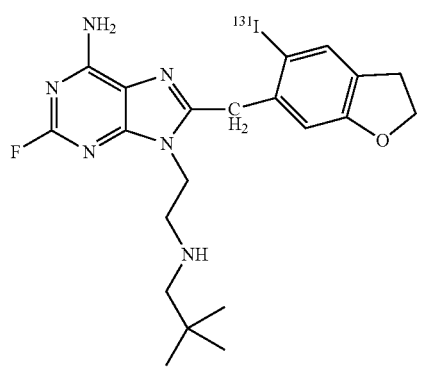
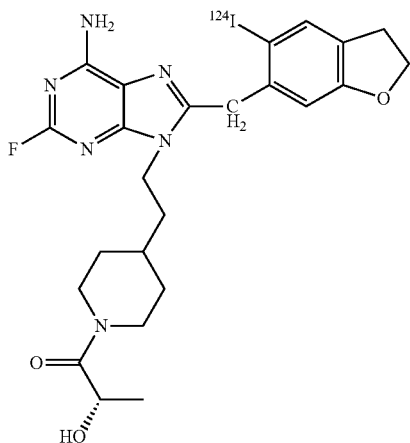
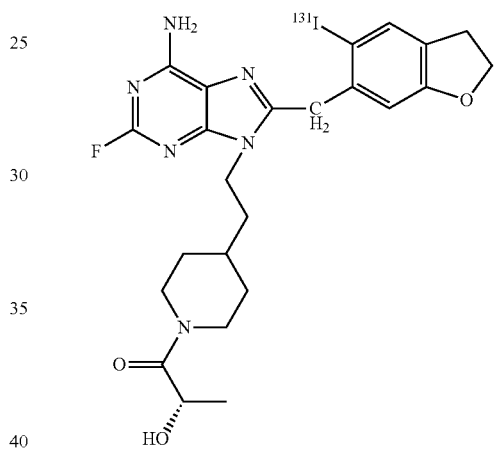
In still another embodiment, a radiolabeled compound in a provided method is selected from a compound having the following formulae:
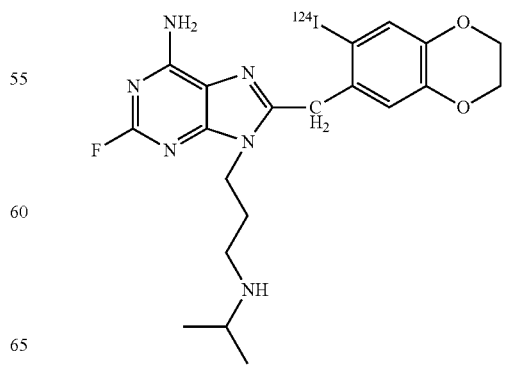

-continued
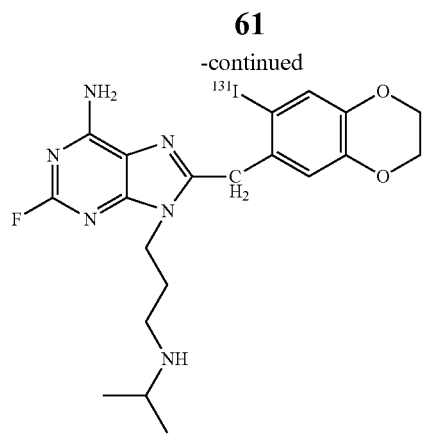
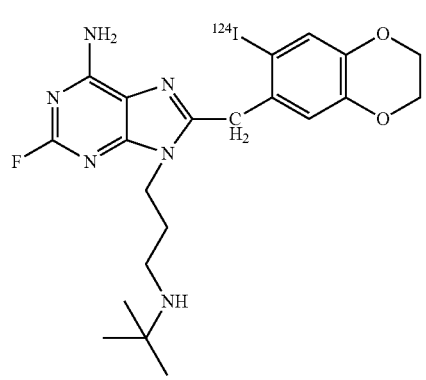
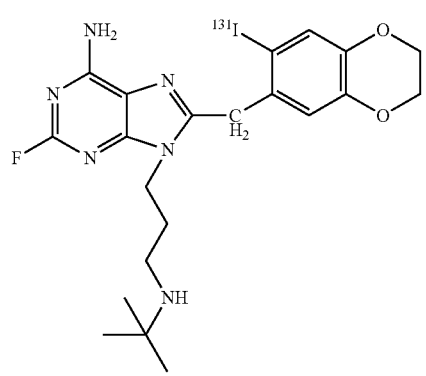
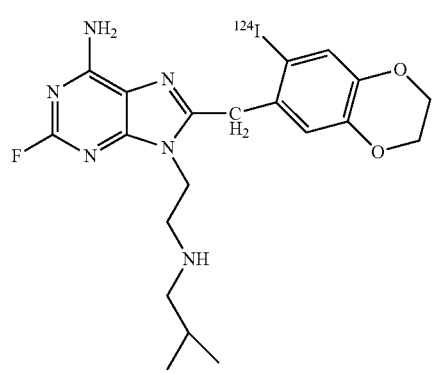
-continued
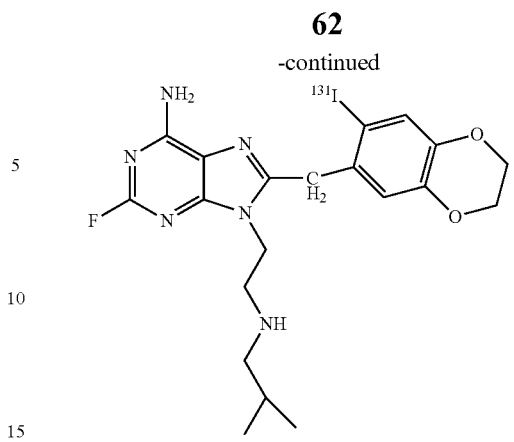
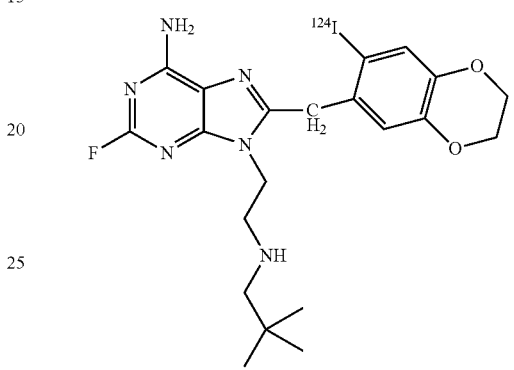
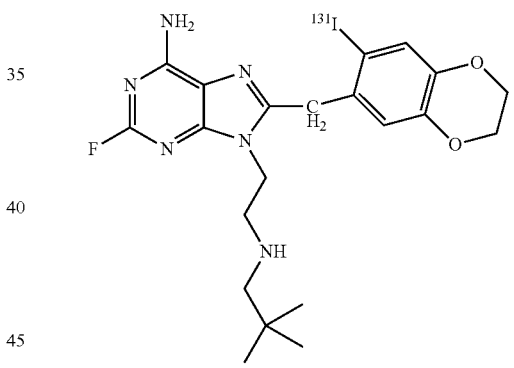
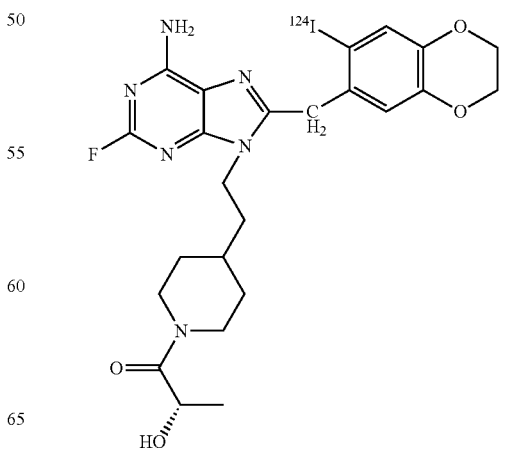

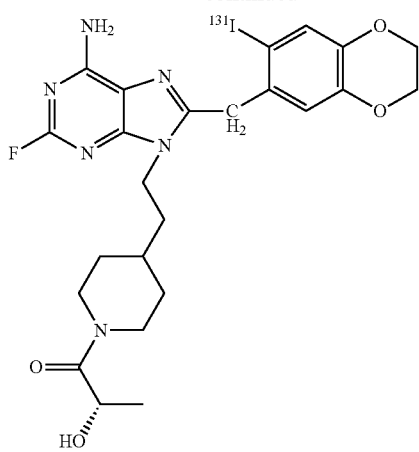
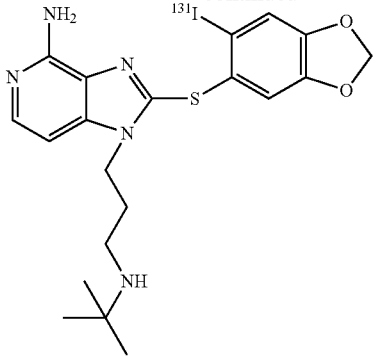
In still another embodiment, a radiolabeled compound in a provided method is selected from a compound having the following formulae:
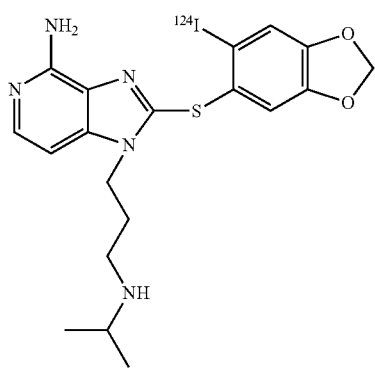
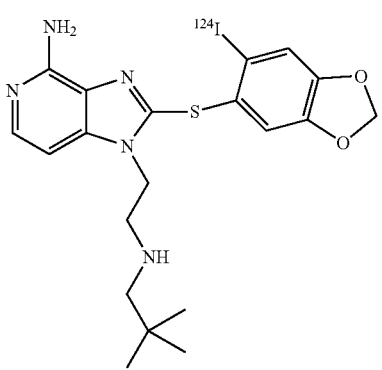
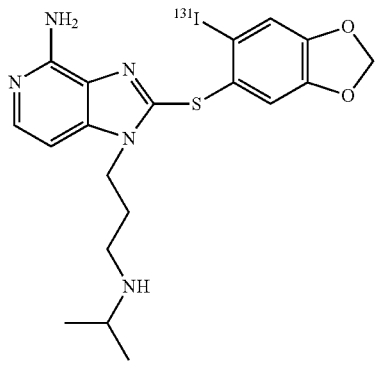
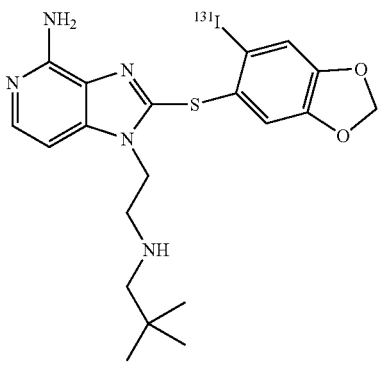
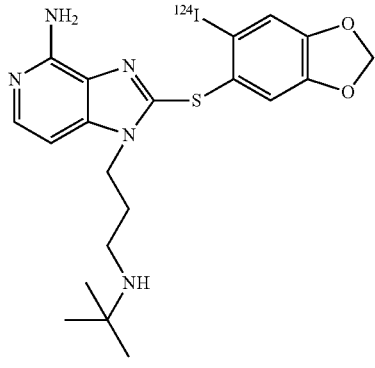
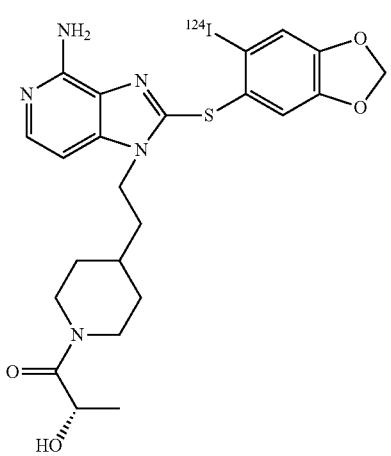

65
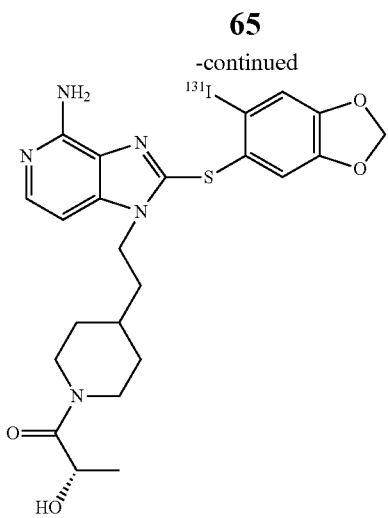
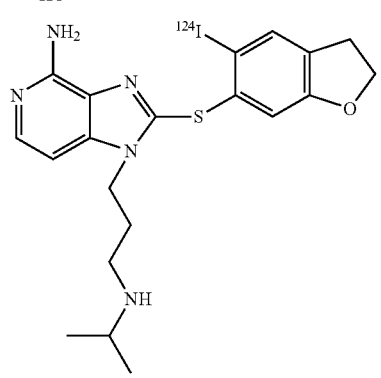
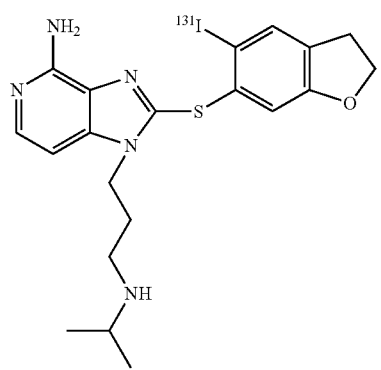
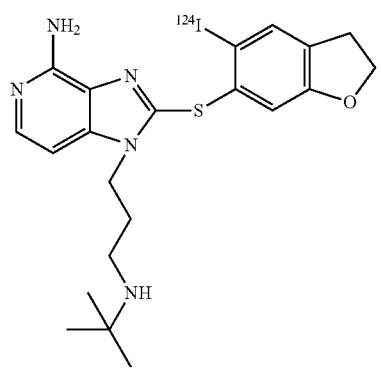
66
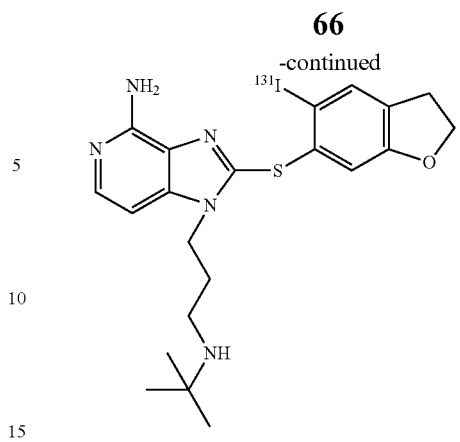
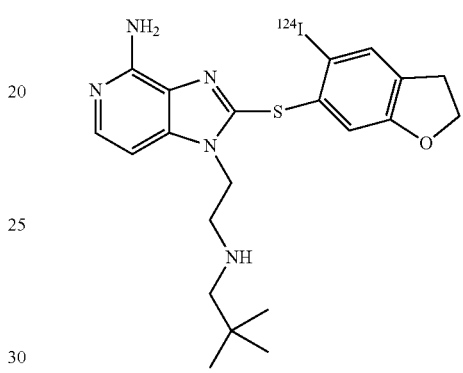
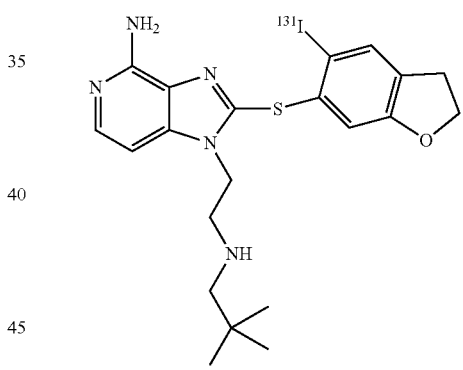
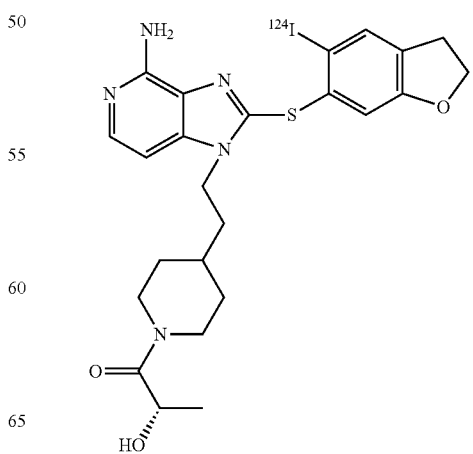

67
-continued
68
-continued
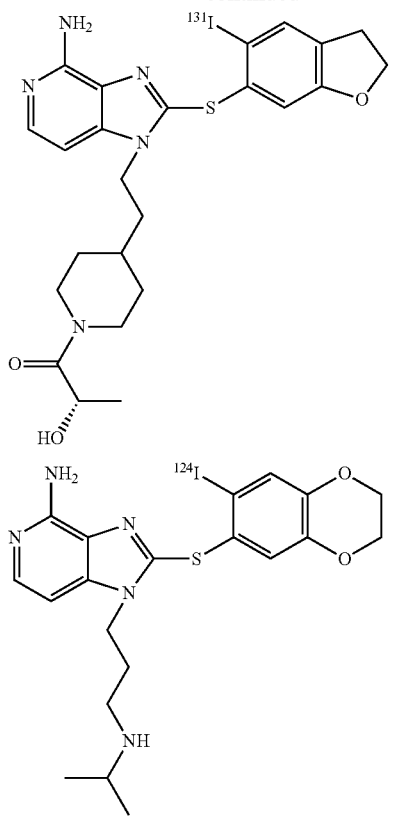
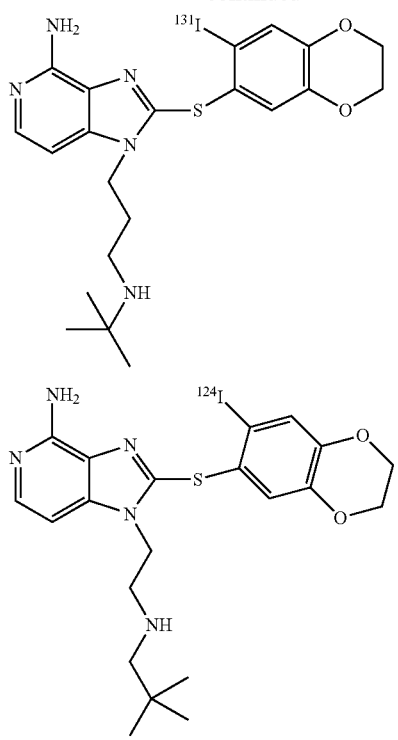
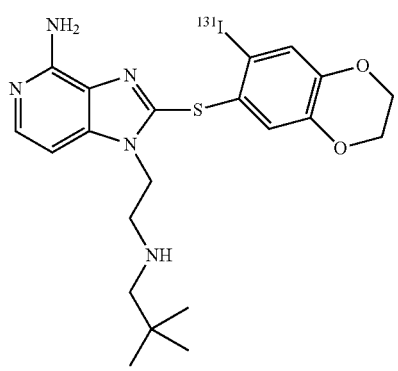
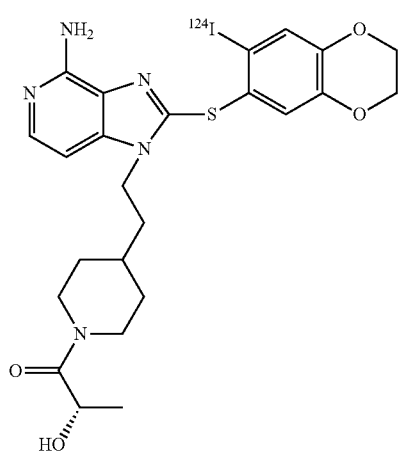

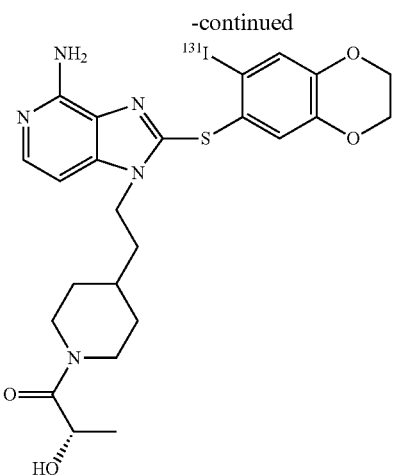

In still another embodiment, a radiolabeled compound in a provided method is selected from a compound having the following formulae:

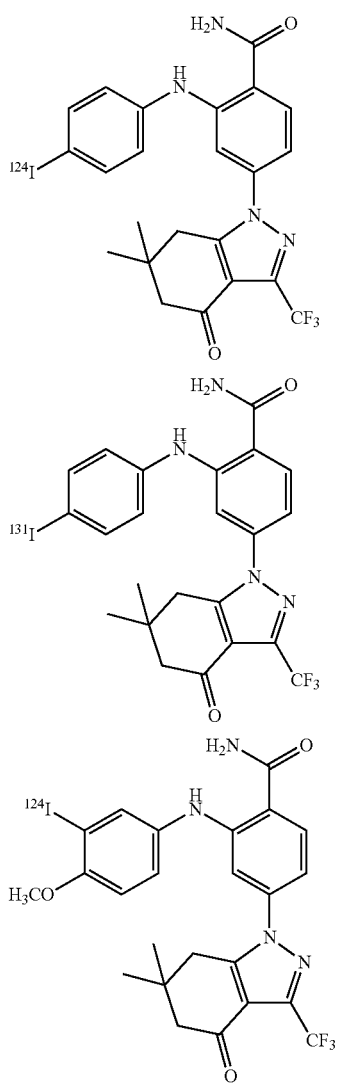

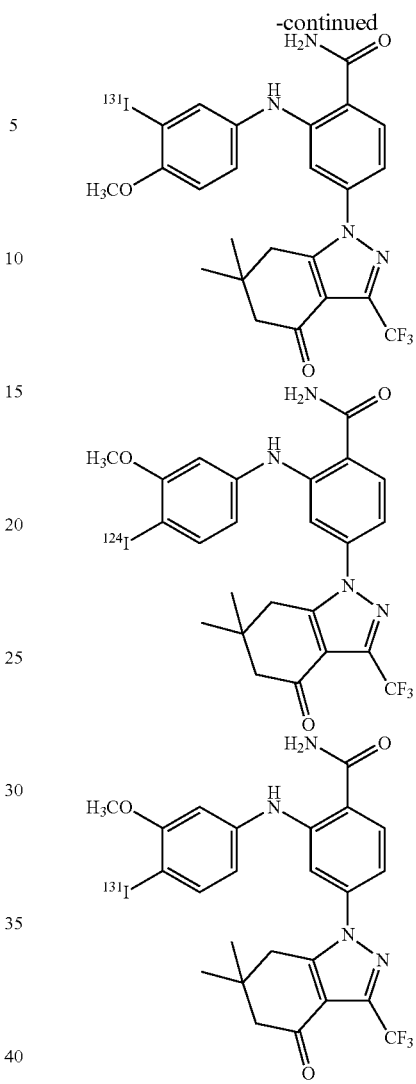

Methods of synthesizing the radiotracers in the above embodiments can be found for instance in U.S. Pat. No. 7,834,181, WO 2011/044394, WO 2008/005937 and PCT application PCT/US2012/032371, the contents of each of which are hereby incorporated by referene in their entirety.

In some embodiments, a provided method comprises using a complementary companion diagnostic to cancer therapy. In some embodiments, a provided method comprises using a complementary companion diagnostic to cardiovascular therapy. In some embodiments, a provided method comprises using a complementary companion diagnostic to Hsp90-targeted cardiovascular therapy. For example, compound A is clinical candidate for the treatment of cancer. In some embodiments, provided methods employ compound A along with a labeled analog of compound A.

In some embodiments, the imaging of a provided method is non-invasive.

EXEMPLIFICATION

Methods for preparing the labeled compounds are widely known in the art, for example but not limited to U.S. Pat. No. 7,834,181, the entirety of which is hereby incorporated by reference. Suitable imaging technologies, such as PET, SPECT and CT, and their combination with other imaging and/or diagnostic techniques, are widely known and practiced in the art as well.

Exemplary Procedure Using $^{124}$I-PUH71 (Compound A)

Within 2 weeks of the starting the imaging process, a subject was given:

1) Standard blood tests for blood counts and liver, thyroid, and kidney function; and 2) Pregnancy test (if applicable, for women of childbearing age (11-55 years) and/or childbearing potential).

The day before the administration of $^{124}$I-PUH71, potassium iodide was administered to the subject to be imaged to minimize the amount of radioactivity in the thyroid.

Potassium iodide drops were continuously administered once a day for two weeks.

A dose of KI was administered before $^{124}$I-PUH71 was injected in the vein of the arm of the subject through a catheter. A subject was typically administered one tracer-dose of $^{124}$I-PUH71 5% ethanol and 0.9% NaCl, which is <1/500th of the NOAEL limit derived from rodents using the cold PUH71. A dose of up to 5.5 mCi of $^{124}$I-PUH71 were administered intravenously.

$^{124}$I-PUH71: radiochemical purity >95% by radio thin-layer chromatography; radiochemical purity >95% by HPLC/UV/220 nm; radionuclide purity conforming to expected spectrum by gamma spectrum analyzer.

$^{124}$I-PUH71 was produced in formulation. The radioactive half-life is 4.2 days. The compound is stable, in formulation, for several days. $^{124}$I-PUH71 has a radiotracer specific activity of >65 mCi per μmole or <7.8 μg of PUH71 per mCi of $^{124}$I.

$^{124}$I-PUH71 scans were performed immediately, at 3-4 hours, 20-24 hours, and 48-72 hours after injection of the radiotracer. A 30-45 minute scanning time-period is typical for clinical PET studies. Image was acquired on a PET-CT scanner. A low-dose CT was obtained immediately prior to PET imaging; the 0-hour CT is applied to the three PET datasets rapidly-acquired during the first 30 minutes post-injection.

Figure 1B:
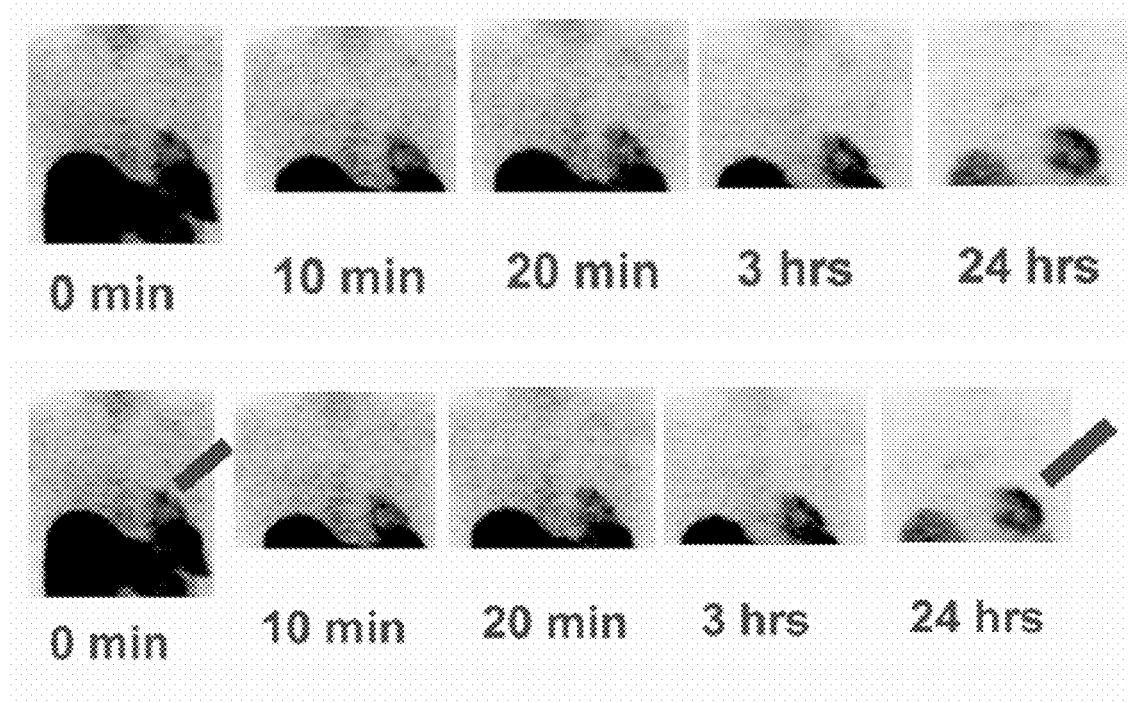

Exemplary images are shown in FIG. 1. Surprisingly, after PUH71 injection, uptake in the heart is maximized in less than 10 minutes and the signal intensity maintain for at least the first 3 hours. Visually-distinct cardiac uptake persists well-beyond 3-4 hours.

Figure 2:
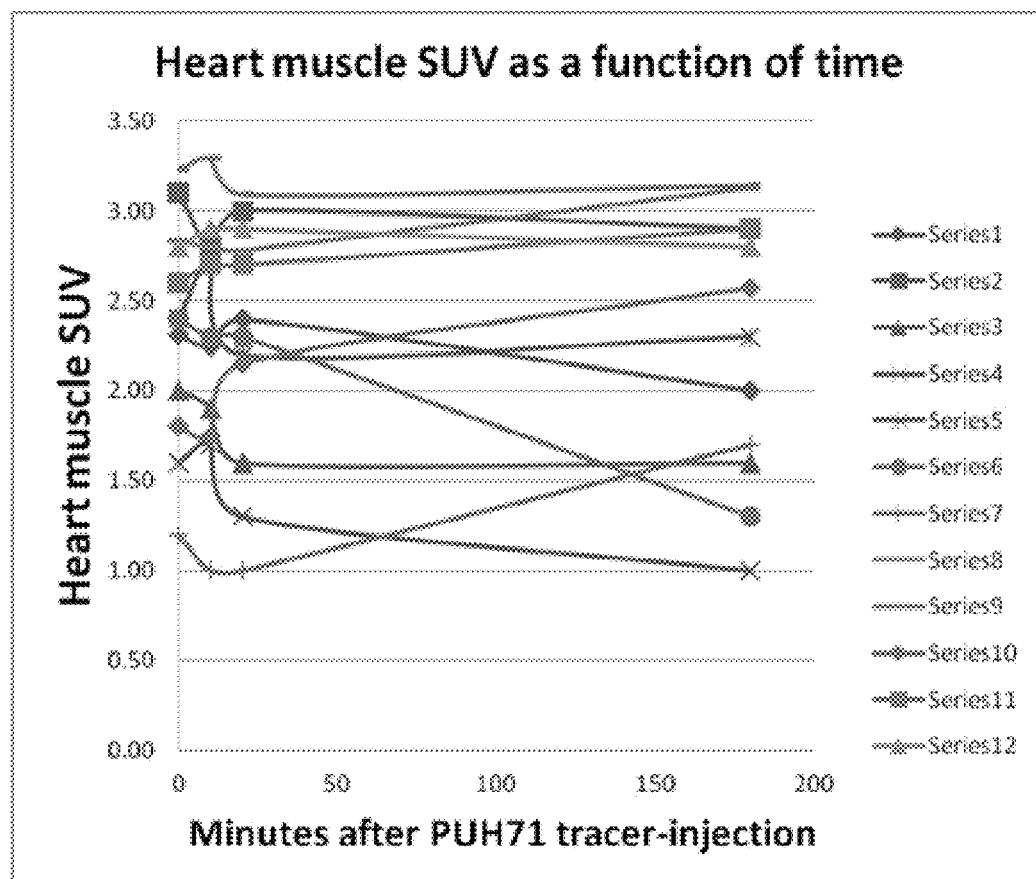
FIG. 2: Uptake of the PUH71 by heart muscle in 12 patients, at serial PET-CT time-points after a single PUH71 tracer injection.

Uptake of the PUH71 by heart muscle in 12 patients are illustrated in FIG. 2. The cardiac uptake is plotted on the y-axis, expressed in terms of the standardized uptake value (SUV), here using the SUV mean parameter. The time after injection is plotted on the x-axis, in minutes. Data shown here is from PET scans obtained 0, 10, 20 and ~180 minutes after tracer injection. In 11 out of 12 patients, the heart musculature demonstrated visually-distinct uptake. In 1 patient, the cardiac uptake was less distinct, but the PET imaging methodology was suboptimal compared to the other studies. While this study did not synchronize the PET imaging with an electrocardiogram (EKG). EKG-synchronization, or 'EKG-gating', is standard practice in cardiac imaging, for improving the quality of heart-imaging, and it is expected that results will further improve after EKG gating is added. Without intention to be limited by theory, the bits of variation in the SUV could be due to (1) the lack of EKG-gating and (2) the lack of proper attenuation correction. This variation would be expected to significantly decrease or disappear when EKG-gating and proper attenuation correction, either by "rod-source" or by CT, are performed. The EKG-gating and attenuation correction techniques are standard practice in cardiac nuclear imaging art.

Mouse Protocols and Results

Figure 4B:
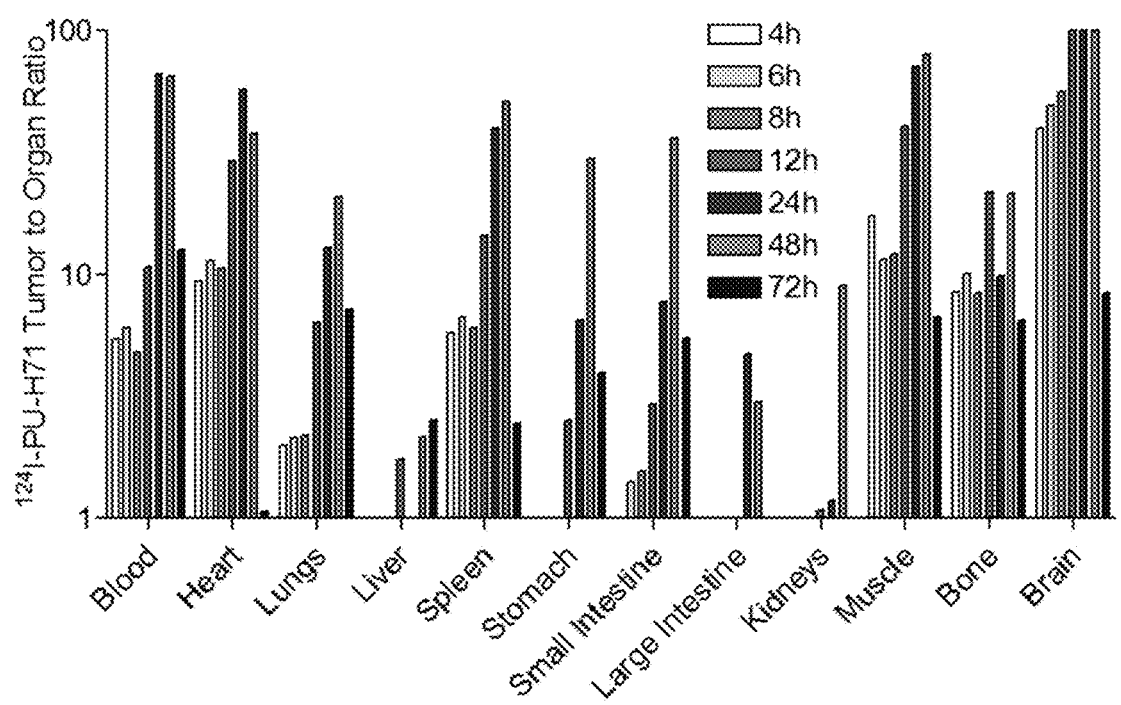
FIG. 4: [$^{124}$I]-PUH71 PET in mice bearing a xenografted tumor. a) Representative PET scan of [$^{124}$I]-PUH71 in MDA-MB-468 tumor-bearing mice. Location of the tumor is indicated by a red arrow. Note no distinct uptake in the heart (no cardiac disease expected in these mice at this age).
b) The [$^{124}$I]-PUH71 tumor-to-organ activity concentration ratios for the indicated times post-administration. Representative data is shown. Note that the heart and blood pool show similar profile indicative of a rapid clearance of [$^{124}$I]-PUH71 from the healthy heart.

We injected mice bearing MDA-MB-468 human breast cancer tumors with trace amounts of $^{124}$I-PUH71, and imaged with the micro PET at 1, 4 and 24 hours post injection. The drug was retained in tumors even at 24 h p.i. Excess radioligand was cleared via the liver and GI tract. The biodistribution of $^{131}$I-PUH71 in nude mice showed a rapid clearance of excess agent from the blood, heart, lung, spleen and muscle, with a similar kinetic of retention in tumor. $^{131}$I-PU-H71 bound, selectively, to Hsp90 in several prostate cancer cell lines; binding was saturable with a $B_{max}$ of 3 to 7 million sites, per cell, and $K_d$ values of 80 and 35 nM, respectively. The results are illustrated in FIG. 4.

Synthesis of [$^{124}$I]-PUH71

The general chemical scheme for the radiochemical synthesis of [$^{124}$I]-PU-H71 is illustrated below. [$^{124}$I]-NaI (~50 μL) was transferred to 1 mL reacti-vial and to it trimethyl tin precursor (Me$_3$Sn-PU-H71) (25 μg) dissolved in 20 μL of methanol was added. To the resulting solution 15 μL of freshly prepared chloramine-T (1.5 mg/mL in acetic acid) was added and the reaction mixture was heated at 50° C. for 5 minutes. The vial was allowed to cool for 2 min and 10 μL of methionine methyl ester (0.5 g/mL) in water was added. Finally, 10 μL of concentrated HCl was added and the solution was heated at 50° C. for 30 min with occasional shaking. The reaction mixture was cooled to room temperature and purified using HPLC. The product was collected and the solvent was removed under reduced pressure using a rotary evaporator. The final product was formulated in 5% ethanol in saline (0.9%). 5% ethanol was used to avoid adherence of the minute amounts of tracer to the walls of the flask. Next, the solution was passed through 0.22 μm filter into pyrogen free vial equipped with a sterile vent. A portion of final formulation was withdrawn and used for quality control analysis.

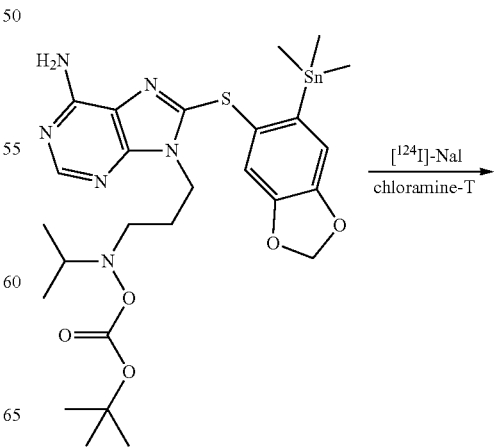

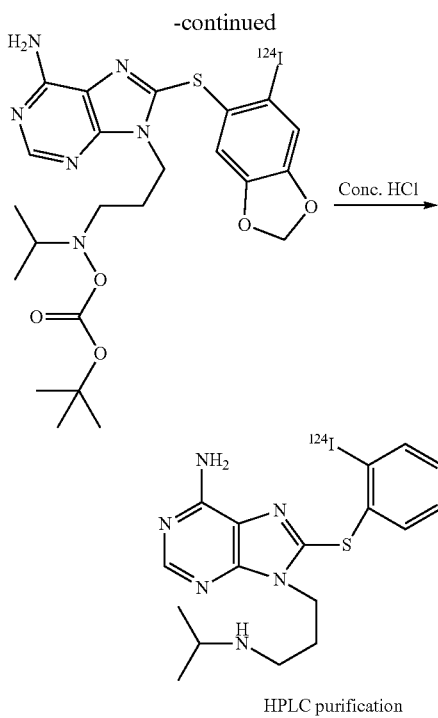

In some embodiments, a cardiac stress test is performed following standard procedures applicable to nuclear cardiac stress tests with conventional SPECT and PET agents prior to the present invention. In some embodiments, a nuclear stress test is preformed after the injection of $^{124}$I-PUH71, following established and widely practiced protocols.

What is claimed is:

1. A method for imaging cardiac tissue in a subject in need thereof, comprising steps of:
   (a) administering to the subject a labeled compound that preferentially binds to stress specific Hsp90 as compared to other forms of Hsp90; and
   (b) imaging the cardiac tissue of the subject by detecting the labeled compound in the subject;
   wherein a cardiac stress test is performed on the subject and wherein the labeled compound is a labeled compound of formula I:

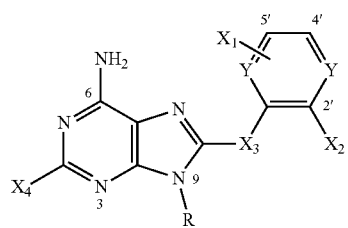

or its pharmaceutically acceptable salt thereof, wherein:
Y is CH, N or O;
R is hydrogen, a $CH_1$ to $C_{10}$ alkyl, alkenyl, alkynyl, or an alkoxyalkyl group, optionally comprising one or more heteroatoms, or a targeting moiety connected to N9 via a linker;
$X_4$ is hydrogen or halogen;

$X_3$ is $CH_2$, $CF_2$, S, SO, $SO_2$, O, NH, or $NR^2$, wherein $R^2$ is alkyl;

$X_2$ is halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$alkyl, COO-alkyl, $NH_2$, OH, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl or O-alkyl; and $X_1$ represents two substituents, which may be the same or different, disposed in the 4' and 5' positions on the aryl group, wherein $X_1$ is selected from halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$-alkyl, COO-alkyl, $NH_2OH$, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl, or O-alkyl, $C_1$ to $C_6$ alkyl or alkoxy, or wherein $X_1$ has the formula —O—$(CH_2)_n$—O—, wherein n is an integer from 0 to 2, and one of the oxygens is bonded at the 5'-position and the other at the 4'-position of the aryl ring;

wherein each hydrogen of the compound of formula I is optionally and independently substituted with a group that can be detected by a medical imaging technique, and/or at least one atom in the compound is optionally enriched in an isotope that can be detected by a medical imaging technique.

2. The method of claim 1, further comprising comparing the data of a first cardiac position of an image obtained in step (b) to those of a second cardiac position, wherein the second cardiac position is from another cardiac image or a different position of the same cardiac image.

3. The method of claim 2, wherein the comparison or analysis of images comprises identifying abnormal signal compared to a reference, wherein the abnormal signal indicates an increased risk of a cardiovascular condition, disorder, or disease.

4. The method of claim 3, wherein the abnormal signal indicates increased risk of coronary artery disease, myocardial dysfunction, and/or abnormal myocardial blood flow.

5. The method of claim 3, wherein the cardiovascular disease, disorder, or condition is associated with stress-specific Hsp90.

6. The method of claim 2, further comprising performing a nuclear stress test on the subject.

7. The method of claim 1, further comprising performing a nuclear stress test on the subject.

8. The method of claim 1, wherein at least one atom in the compound is optionally enriched in an isotope that can be detected by a medical imaging technique.

9. The method of claim 1, wherein the labeled compound inhibits Hsp90.

10. The method of claim 1, wherein the labeled compound is administered before, during, or after administration of a non-radioactive therapeutic compound.

11. The method of claim 10, wherein the non-radioactive therapeutic compound has the structure of formula X:

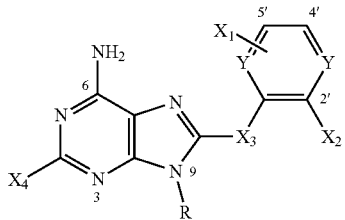

or its pharmaceutically acceptable salt thereof, wherein:
Y is CH, N or O;
R is hydrogen, a $C_1$ to $C_{10}$ alkyl, alkenyl, alkynyl, or an alkoxyalkyl group, optionally comprising one or more heteroatoms, or a targeting moiety connected to N9 via a linker;
$X_4$ is hydrogen or halogen;
$X_3$ is $CH_2$, $CF_2$, S, SO, $SO_2$, O, NH, or $NR^2$, wherein $R^2$ is alkyl;
$X_2$ is halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$alkyl, COO-alkyl, $NH_2$, OH, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl or O-alkyl; and
$X_1$ represents two substituents, which may be the same or different, disposed in the 4' and 5' positions on the aryl group, wherein $X_1$ is selected from halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, $SO_2$-alkyl, COO-alkyl, $NH_2$OH, CN, $SO_2X_5$, $NO_2$, NO, C=$SR_2$, $NSO_2X_5$, C=$OR_2$, where $X_5$ is F, $NH_2$, alkyl or H, and $R_2$ is alkyl, $NH_2$, NH-alkyl, or O-alkyl, $C_1$ to $C_6$ alkyl or alkoxy, or wherein $X_1$ has the formula —O—$(CH_2)_n$—O—, wherein n is an integer from 0 to 2, and one of the oxygens is bonded at the 5'-position and the other at the 4'-position of the aryl ring;
or the non-radioactive therapeutic compound has a structure depicted in any of groups (i) to (vi):

(i)

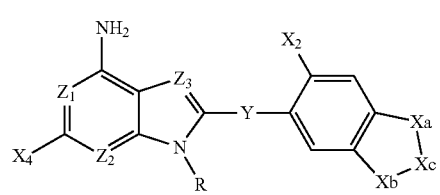
(III)

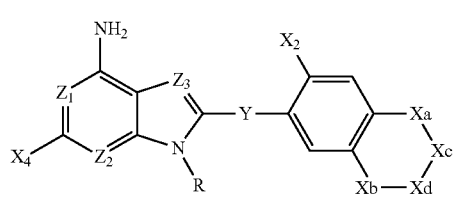
(IV)

or a pharmaceutically acceptable salt thereof, wherein:
(a) each of $Z_1$ $Z_2$ and $Z_3$ is independently CH or N;
(b) Y is $CH_2$, O, or S;
(c) Xa, Xb, Xc and Xd are independently selected from CH, $CH_2$, O, N, NH, S, carbonyl, fluoromethylene, and difluoromethylene selected so as to satisfy valence, wherein each bond to an X group is either a single bond or a double bond;
(d) $X_2$ is I
(e) $X_4$ is hydrogen or halogen; and
(f) R is straight-chain- or branched- substituted or unsubstituted alkyl, straight-chain- or branched- substituted or unsubstituted alkenyl, straight-chain- or branched- substituted or unsubstituted alkynyl, or substituted or unsubstituted cycloalkyl, wherein the R group is optionally interrupted by
—S(O)N($R_A$)—, —$NR_A$S(O)—, —$SO_2$N($R_A$)—, —$NR_A$$SO_2$—, —C(O)N($R_A$)—, or —$NR_A$C(O)—, and/or the R group is optionally terminated —S(O)$NR_AR_B$, —$NR_A$S(O)$R_B$, —$SO_2NR_AR_B$, —$NR_ASO_2R_B$, —C(O)$NR_AR_B$, or —$NR_A$C(O)$R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl;

(ii)

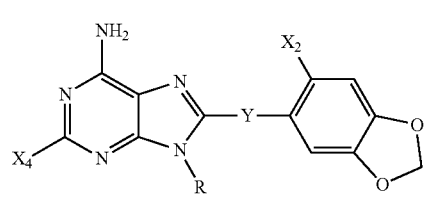
(V)

or a pharmaceutically acceptable salt thereof, wherein:
Y is $CH_2$ or S;
$X_4$ is H or halogen
$X_2$ is I; and
R is —$(CH_2)_m$—N—$R_{10}R_{11}R_{12}$ or —$(CH_2)_m$—N—$R_{10}R_{11}$, where m is 2 or 3 and where $R_{10}$-$R_{12}$ are independently selected from hydrogen, methyl, ethyl, ethenyl, ethynyl, propyl, hydroxyalkyl, isopropyl, t-butyl, isobutyl, cyclopentyl, a 3-membered ring including the nitrogen or a 6-membered ring including the N and optionally an additional heteroatom with substituents to satisfy valence, with the proviso that when all of $R_{10}$-$R_{12}$ are present the compound further comprises a pharmaceutically acceptable counter ion;

(iii)

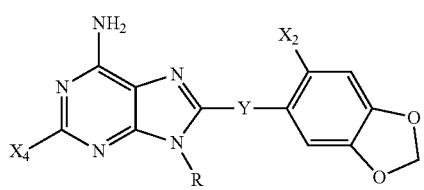
(VI)

or a pharmaceutically acceptable salt thereof, wherein:
Y is CH₂ or S;
X₄ is H or halogen;
X₂ is I; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide;

(iv)

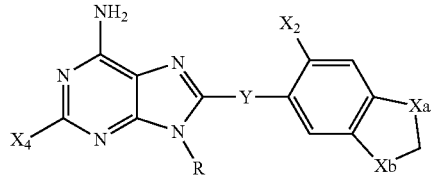

(VII)

or a pharmaceutically acceptable salt thereof, wherein:
one of Xa and Xb is O and the other is CH₂;
Y is CH₂ or S;
X₄ is hydrogen or halogen; and
X₂ is I; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide;

(v)

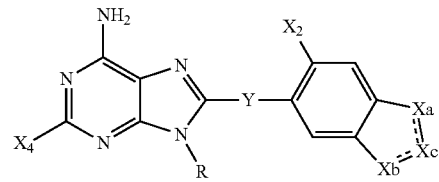

(VIII)

or a pharmaceutically acceptable salt thereof, wherein:
Xa-Xc-Xb is CH₂—CH₂—CH₂, CH=CH—CH₂, or CH₂—CH=CH;
Y is CH₂ or S;
X₂ is I; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide;

(vi)

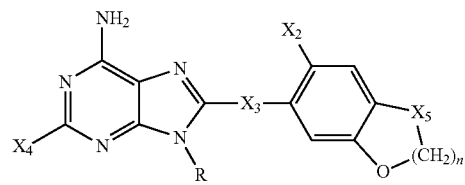

(IX)

or a pharmaceutically acceptable salt thereof, wherein:
X₃ is CH₂, CF₂, S, SO, SO₂, O, NH, or NR², wherein R² is alkyl;
X₂ is I;
X₄ is hydrogen or halogen;
X₅ is O or CH₂;
R is 3-isopropylaminopropyl, 3-(isopropyl(methyl)amino)propyl, 3-(isopropyl(ethyl)amino)propyl, 3-((2-hydroxyethyl)(isopropyl)amino)propyl, 3-(methyl(prop-2-ynyl)amino)propyl, 3-(allyl(methyl)amino)propyl, 3-(ethyl(methyl)amino)propyl, 3-(cyclopropyl(propyl)amino)propyl, 3-(cyclohexyl(2hydroxyethyl)amino)propyl, 3-(2-methylaziridin-1-yl)propyl, 3-(piperidin-1-yl)propyl, 3-(4-(2-hydroxyethyl)piperazin-1-yl)propyl, 3-morpholinopropyl, 3-(trimethylammonio)propyl, 2-(isopropylamino)ethyl, 2-(isobutylamino)ethyl, 2-(neopentylamino)ethyl, 2-(cyclopropylmethylamino)ethyl, 2-(ethyl(methyl)amino)ethyl, 2-(isobutyl(methyl)amino)ethyl, or 2-(methyl(prop-2-ynyl)amino)ethyl, and
n is 1 or 2.

12. The method of claim 11, wherein the non-radioactive therapeutic compound is

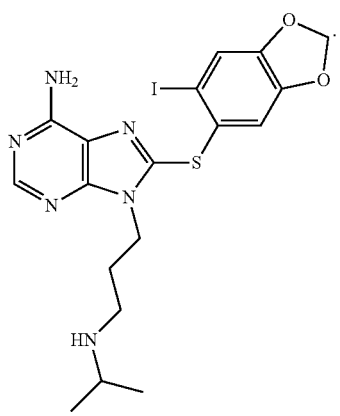

13. The method of claim 1, wherein the imaging measures the accessibility of cardiac Hsp90 to a therapeutic compound.

14. The method of claim 1, wherein the imaging measures the concentrations of a therapeutic compound in the cardiac tissue.

15. The method of claim 10, wherein the imaging measures the occupancy or saturation of cardiac Hsp90 achieved by a therapeutic compound or the ability of a therapeutic compound to displace the labeled compound.

16. The method of claim 1, wherein the labeled compound is a labeled compound having the structure of:

II

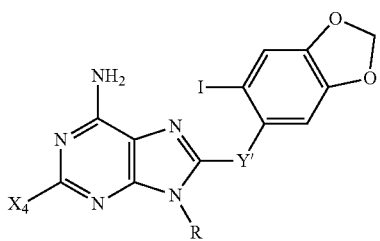

wherein Y' is —CH₂— or S;
X₄ is a hydrogen or halogen; and R is an alkyl moiety, optionally substituted on the amino nitrogen with one or two carbon-containing substituents selected independently from the group consisting of alkyl, alkenyl and alkynyl substituents, wherein the total number of carbons in the amino alkyl moiety is from 1 to 9.

17. The method of claim 16, wherein the compound is labeled at 2'-iodo.

18. The method of claim 17, wherein the label at 2'-iodo is $^{123}$I, $^{124}$I, $^{125}$I or $^{131}$I.

19. The method of claim 1, wherein the labeled compound is labeled compound A:

A

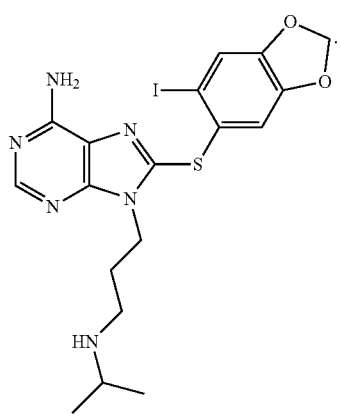

20. The method of claim 19, wherein compound A is labeled at 2'-iodo.

21. The method of claim 20, wherein the label at 2'-iodo is $^{123}$I, $^{124}$I, $^{125}$I or $^{131}$I.

22. The method of claim 19, wherein compound A is labeled through substituting a hydrogen atom with a group that can be detected by a medical imaging technique.

23. The method of claim 1, wherein the labeled compound comprises an isotope which decays by positron emission.

24. The method of claim 1, wherein the labeled compound comprises an isotope that decays by electron capture.

25. The method of claim 1, wherein the labeled compound is selected from:

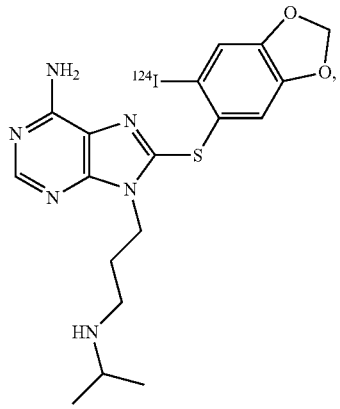 [SMILES: CC(C)NCCCn1c(Sc2cc3c(cc2I)OCO3)nc2c(N)ncnc21]

-continued
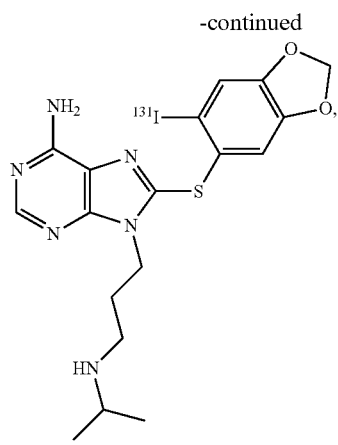
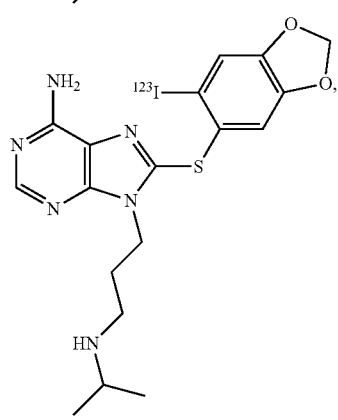
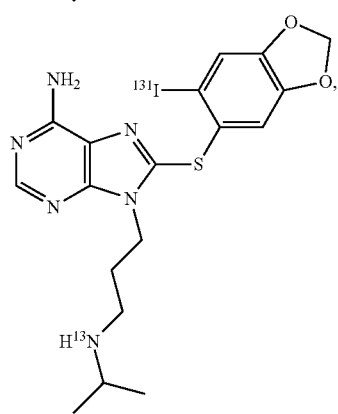
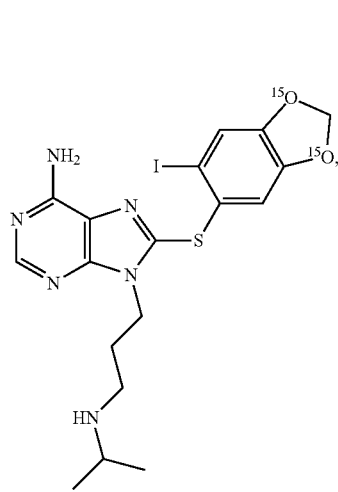
-continued
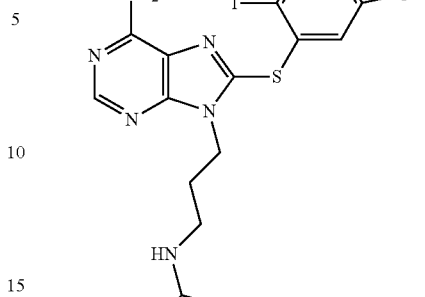
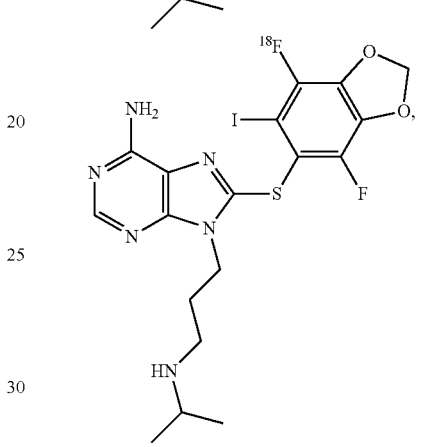
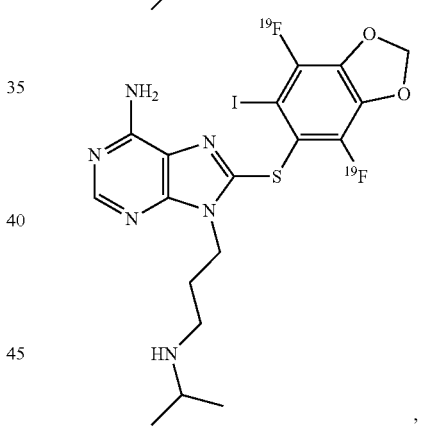
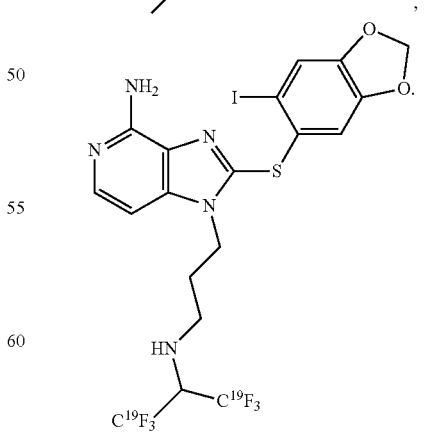
, and
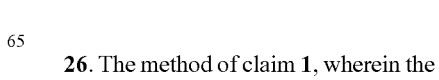
26. The method of claim 1, wherein the labeled compound is a labeled analog of geldanamycin, radicicol, or gamitrinib.

27. A method for the diagnosis, evaluation, or prediction of risk of patient morbidity or mortality associated with cardiovascular diseases, conditions, or disorders, comprising (a) administering a labeled compound of any of formula I to IX to a subject in need thereof, wherein formula I to IX have structures as depicted below:

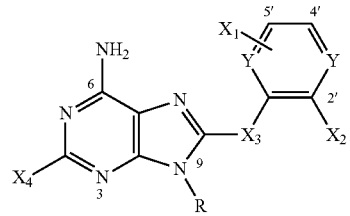
I

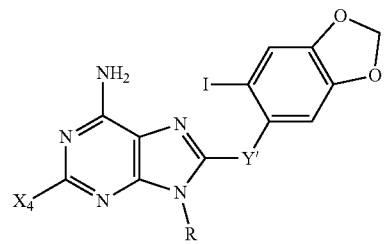
II wherein Y' is —CH$_2$— or S;
wherein I is $^{123}$I, $^{124}$I, $^{125}$I or $^{131}$I: and,
X$_4$ is hydrogen or halogen; and R is an amino alkyl moiety, optionally substituted on the amino nitrogen with one or two carbon-containing substituents selected independently from the group consisting of alkyl, alkenyl and alkynyl substituents, wherein the total number of carbons in the amino alkyl moiety is from 1 to 9;

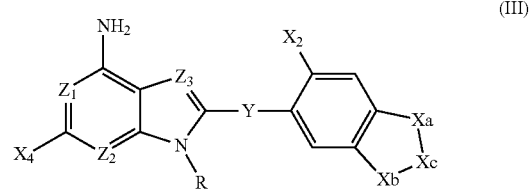
(III)

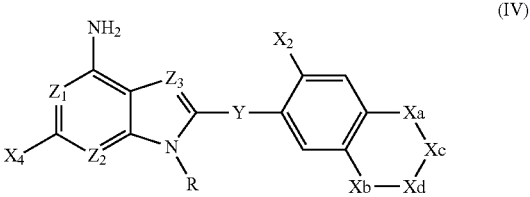
(IV)

or its pharmaceutically acceptable salt thereof, wherein:
Y is CH, N or O;
R is hydrogen, a C$_1$ to C$_{10}$ alkyl, alkenyl, alkynyl, or an alkoxyalkyl group, optionally comprising one or more heteroatoms, or a targeting moiety connected to N9 via a linker;
X$_4$ is hydrogen or halogen;
X$_3$ is CH$_2$, CF$_2$, S, SO, SO$_2$, O, NH, or NR$^2$, wherein R$^2$ is alkyl;
X$_2$ is halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, SO$_2$alkyl, COO-alkyl, NH$_2$, OH, CN, SO$_2$X$_5$, NO$_2$, NO, C=SR$_2$, NSO$_2$X$_5$, C=OR$_2$, where X$_5$ is F, NH$_2$, alkyl or H, and R$_2$ is alkyl, NH$_2$, NH-alkyl or O-alkyl; and X$_1$ represents two substituents, which may be the same or different, disposed in the 4' and 5' positions on the aryl group, wherein X$_1$ is selected from halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, SO$_2$-alkyl, COO-alkyl, NH$_2$OH, CN, SO$_2$X$_5$, NO$_2$, NO, C=SR$_2$, NSO$_2$X$_5$, C=OR$_2$, where X$_5$ is F, NH$_2$, alkyl or H, and R$_2$ is alkyl, NH$_2$, NH-alkyl, or O-alkyl, C$_1$ to C$_6$ alkyl or alkoxy, or wherein X$_1$ has the formula —O—(CH$_2$)$_n$—O—, wherein n is an integer from 0 to 2, and one of the oxygens is bonded at the 5'-position and the other at the 4'-position of the aryl ring;

wherein each hydrogen of the compound of formula I is optionally and independently substituted with a group that can be detected by a medical imaging technique, and/or at least one atom in the compound is optionally enriched in an isotope that can be detected by a medical imaging technique, or a pharmaceutically acceptable salt thereof, wherein:
(a) each of Z$_1$, Z$_2$ and Z$_3$ is independently CH or N;
(b) Y is CH$_2$, O, or S;
(c) Xa, Xb, Xc and Xd are independently selected from CH, CH$_2$, O, N, NH, S, carbonyl, fluoromethylene, and difluoromethylene selected so as to satisfy valence, wherein each bond to an X group is either a single bond or a double bond;
(d) X$_2$ is $^{123}$I, $^{124}$I, $^{125}$I or $^{131}$I;
(e) X$_4$ is hydrogen or halogen; and
(f) R is straight-chain- or branched- substituted or unsubstituted alkyl, straight-chain- or branched- substituted or unsubstituted alkenyl, straight-chain- or branched- substituted or unsubstituted alkynyl, or substituted or unsubstituted cycloalkyl, wherein the R group is optionally interrupted by
—S(O)N(R$_A$)—, —NR$_A$S(O)—, —SO$_2$N(R$_A$)—, —NR$_A$SO$_2$—, —C(O)N(R$_A$)—, or —NR$_A$C(O)—, and/or the R group is optionally terminated by —S(O)NR$_A$R$_B$, —NR$_A$S(O)R$_B$, —SO$_2$NR$_A$R$_B$, —NR$_A$SO$_2$R$_B$, —C(O)NR$_A$R$_B$, or —NR$_A$C(O)R$_B$, wherein each R$_A$ and R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl;

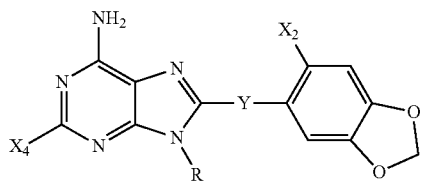

(V)

or a pharmaceutically acceptable salt thereof, wherein:
Y is $CH_2$ or S;
$X_4$ is H or halogen
$X_2$ is $_{123}I$, $_{124}I$, $_{125}I$ or $_{131}I$; and
R is —$(CH_2)_m$—N—$R_{10}R_{11}R_{12}$ or —$(CH_2)_m$—N—$R_{10}R_{11}$, where m is 2 or 3 and where $R_{10}$-$R_{12}$ are independently selected from hydrogen, methyl, ethyl, ethenyl, ethynyl, propyl, hydroxyalkyl, isopropyl, t-butyl, isobutyl, cyclopentyl, a 3-membered ring including the nitrogen or a 6-membered ring including the N and optionally an additional heteroatom with substituents to satisfy valence, with the proviso that when all of $R_{10}$-$R_{12}$ are present the compound further comprises a pharmaceutically acceptable counter ion;

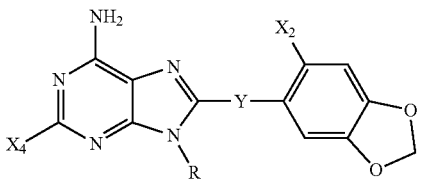

(VI)

or a pharmaceutically acceptable salt thereof, wherein:
Y is $CH_2$ or S;
$X_4$ is H or halogen;
$X_2$ is $_{123}I$, $_{124}I$, $_{125}I$ or $_{131}I$; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane -1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide;

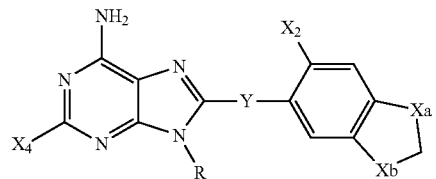

(VII)

or a pharmaceutically acceptable salt thereof, wherein:
one of Xa and Xb is O and the other is $CH_2$;
Y is $CH_2$ or S;
$X_4$ is hydrogen or halogen; and
$X_2$ is $_{123}I$, $_{124}I$, $_{125}I$ or $_{131}I$; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide;

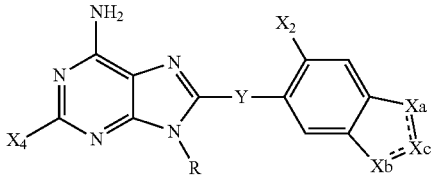

(VIII)

or a pharmaceutically acceptable salt thereof, wherein:
Xa-Xc-Xb is $CH_2$—$CH_2$—$CH_2$, CH=CH—$CH_2$, or $CH_2$—CH=CH;
Y is $CH_2$ or S;
$X_2$ is $^{123}I$, $^{124}I$, $^{125}I$ or $^{131}I$; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclo-propanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide;

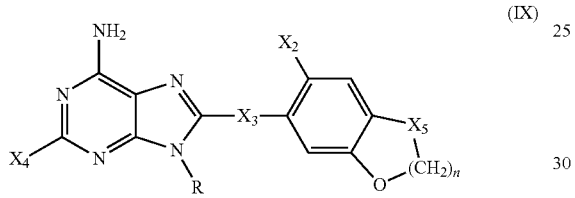

(IX)

or a pharmaceutically acceptable salt thereof, wherein:
X$_3$ is CH$_2$, CF$_2$, S, SO, SO$_2$, O, NH, or NR$^2$, wherein R$^2$ is alkyl;
X$_2$ is $^{123}$I, $^{124}$I, $^{125}$I or $^{131}$I;
X$_4$ is hydrogen or halogen;
X$_5$ is O or CH$_2$;
R is 3-isopropylaminopropyl, 3-(isopropyl(methyl)amino)propyl, 3-(isopropyl(ethyl)amino)propyl, 3-((2-hydroxyethyl)(isopropyl)amino)propyl, 3-(methyl(prop-2-ynyl)amino)propyl, 3-(allyl(methyl)amino)propyl, 3-(ethyl(methyl)amino)propyl, 3-(cyclopropyl(propyl)amino)propyl, 3-(cyclohexyl(2-hydroxyethyl)amino)propyl, 3-(2-methylaziridin-1-yl)propyl, 3-(piperidin-1-yl)propyl, 3-(4-(2-hydroxyethyl)piperazin-1-yl)propyl, 3-morpholinopropyl, 3-(trimethylammonio)propyl, 2-(isopropylamino)ethyl, 2-(isobutylamino)ethyl, 2-(neopentylamino)ethyl, 2-(cyclopropylmethylamino)ethyl, 2-(ethyl(methyl)amino)ethyl, 2-(isobutyl(methyl)amino)ethyl, or 2-(methyl(prop-2-ynyl)amino)ethyl; and n is 1 or 2; and
(b) imaging the cardiac tissue of the subject by detecting the labeled compound in the subject;
wherein a cardiac stress test is performed on the subject.
28. The method of claim 27, wherein the administered labeled compound is formula II.
29. The method of claim 27, wherein the administered labeled compound is

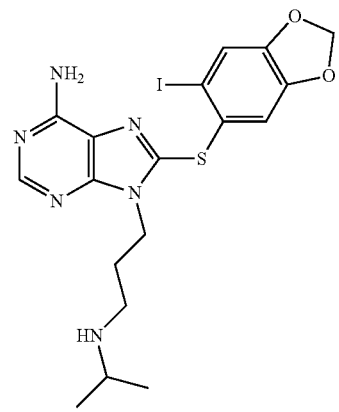 [SMILES: CC(C)NCCCn1c(Sc2cc3c(cc2I)OCO3)nc2c(N)ncnc21]

labeled at 2'-iodo; wherein the label at 2'-iodo is $^{123}$I, $^{124}$I, $^{125}$I or $^{131}$I.

30. A method for the treatment of cardiovascular diseases, conditions, or disorders comprising
(a) administering a compound of any of formula I to IX to a subject in need thereof, and
(b) imaging the cardiac tissue of the subject by detecting the labeled compound in the subject;
wherein a cardiac stress test is performed on the subject.
31. The method of claim 30, wherein the administered labeled compound is formula II.
32. The method of claim 30, wherein the administered labeled compound is

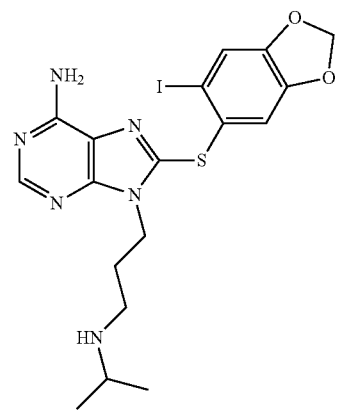 [SMILES: CC(C)NCCCn1c(Sc2cc3c(cc2I)OCO3)nc2c(N)ncnc21]

labeled at 2'-iodo; wherein the label at 2'-iodo is $^{123}$I, $^{124}$I, $^{125}$I or $^{131}$I.

33. A method for determining the dosage of a drug, comprising steps of:
(a) administering a labeled compound of any of formula I to IX to a subject;
(b) imaging the cardiac tissue of the subject by detecting the labeled compound in the subject;
(c) analyzing the images from step (b); and
(d) administering to the subject a suitable amount of a drug.

* * * * *